US006207455B1

(12) United States Patent
Chang

(10) Patent No.: US 6,207,455 B1
(45) Date of Patent: *Mar. 27, 2001

(54) LENTIVIRAL VECTORS

(76) Inventor: Lung-Ji Chang, 3102 NW. 57th Terr., Gainesville, FL (US) 32606-6939

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/935,312

(22) Filed: Sep. 22, 1997

Related U.S. Application Data

(63) Continuation-in-part of application No. 08/848,760, filed on May 1, 1997.

(51) Int. Cl.[7] .................. C12N 15/63; C12N 15/867; C12N 5/10
(52) U.S. Cl. .................. 435/457; 435/320.1; 435/325; 435/363; 435/366; 435/368; 435/369; 435/370; 435/371; 435/372; 435/455; 435/456
(58) Field of Search .................. 435/69.1, 172.1, 435/172.3, 235.1, 320.1, 325, 363, 366, 368, 369, 370, 371, 372, 457, 455, 456

(56) References Cited

U.S. PATENT DOCUMENTS 5,554,524 * 9/1996 Temin et al. .................. 435/235.1

OTHER PUBLICATIONS

Orkin et al., "Report and Recommendations of the Panel to Assess the NIH Investment in Research on Gene Therapy", Dec. 7, 1995.*

Ross et al., Human Gene Therapy, vol. 7, pp. 1781–1790, Sep. 10, 1996.*

Verma et al., Nature, vol. 389, pp. 239–242, Sep. 18, 1997.*

Miele et al., J. of Virol., vol. 70, No. 2, pp. 944–951, Feb. 1996.*

Elder et al., Adv. Virus Res., vol. 45, pp. 225–247, 1995.*

Becker et al., Virus Genes, vol. 8, No. 3, pp. 249–270, 1994.*

* cited by examiner

Primary Examiner—David Guzo
(74) Attorney, Agent, or Firm—Iver P. Cooper

(57) ABSTRACT

The present invention contemplates novel lentiviral vectors which exhibit strong promoter activity in human and other cells. Vectors are provided which are packaged efficiently in packaging cells and cell lines to generate high titer recombinant virus stocks. The present invention further relates to HIV vaccines and compositions for gene therapy. In particular, the present invention provides attenuated replication-competent HIV vaccines and replication-defective HIV vectors.

40 Claims, 18 Drawing Sheets

Replication-competent, LTR, tat, and nef HIV-1 mutants

HIV-1 LTR

Deletion constructs:

Heterologous Enhancer/Promoter Inserts:

1. Human CMV IE(a)

2. Human CMV IE(b)

3. Mo-MLV

HIV Packaging Construct 1-del. env (pHP-1dl.)

Deleted: LTRs, PBS, 5'leader, env, nef, PPT

HIV Transducing Vectors pTVs

A (pTV-ψ+)  Deleted: major splice donor site, gag AUG

B (pTV-Δ)  Deleted: major splice donor site, gag AUG

Possible cross-over to generate RCV from co-transfection

FIG 13A

```
       5801       5811       5821       5831       5841       5851       5861
WT:    AGGCGTTACTCGACAGAGAGAAGACAAGAAATGGAGCCAGTAGATCCTAGACTAGAGCCCTGGAAGCATCC
                                        └─tat starts
tat-B: ------------------------------------------------------------T--G-------

5871       5881       5891       5901       5911       5921       5931
WT:    AGGAAGTCAGCCTAAAACTGCTTGTACCAATTGCTATTGTAAAAGTGTTGCTTTCATTGCCAAGTTTGT
                                       vpr ends ─┘↑
tat-B: -------T-------------------------------------------------------------
```

FIG 13B

```
             ┌─nef starts
      8781   │ 8791      8801      8811      8821      8831      8841
WT:   TATAAGATGGGCTGGCAAGTGGTCAAAAAGTAGTGTGATTGGATGGCCTGCTGTAAGGGAAGAATGAGAC..
nef-A: ------C-T------------------------------------------------------------..
nef-B: ------C-T------------------------------------------------------------..
             └─env ends ...9001  9011      9021      9031      9041      9051      9061
WT:   CTCAGGTACCTTTAAGACCAATGACTTACAAGGCAGCTGTAGATCTTAGCCACTTTTAAAGAAAAGGG
nef-A: ----------------------------------------------------------------
nef-B: ---TCTA--TC--G---------------------------------------------------
```

FIG 17

```
       5801      5811      5821      5831      5841      5851      5861
WT:    AGGGCGTTACTCGACAGAGGAGAGCAAGAAATGGAGCCAGTAGATCCTAGAGACTAGAGCCCTGAAGCATCC
tat-A: ----------------------------------------------------------T--G----------
tat-B: ----------------------------------------------------------T--G----------
tat-C: ------------------------------------C---C---TCGC-TAG----///////CGGCCCCCG 5871      5881      5891      5901      5911      5921      5931
WT:    AGGAAGTCAGCCTAAAACTGCTTGTACCAATTGCTATTGTAAAAAGTGTGCTTTCATTGCCAAGTTTGT
tat-A: ---------------------------------------------------------------------
tat-B: --------T---T--------------------------------------------------------
tat-C: GGATCGATACGC////////-------------------------------------------------
```

LENTIVIRAL VECTORS

This application is a continuation-in-part of Chang, Ser. No. 08/848,760, filed May 1, 1997, now pending.

FIELD OF THE INVENTION

The present invention relates to improved viral vectors useful for the expression of genes at high levels in human cells. These vectors also find use in anti-viral, anti-tumor, and/or gene therapy. The improved vectors contain novel viral gene expression vectors and packaging vectors, that permit increased efficiency of packaging the recombinant viral genome and increased long-term gene expression. The improved vectors may also contain regulatory gene sequences derived from viral or human genomes, but lack viral gene expression coding genomes.

BACKGROUND OF THE INVENTION

Viral vectors have been used as vehicles for the transfer of genes into many different cell types including whole embryos, fertilized eggs, isolated tissue samples, and cultured cell lines. The ability to introduce and express a foreign gene in a cell is useful for the study of gene expression and the elucidation of cell lineages (J. D. Watson et al., Recombinant DNA, 2d Ed., W.H Freeman and Co., NY [1992], pp. 256–263). Retroviral vectors, capable of integration into the cellular chromosome, have also been used for the identification of developmentally important genes via insertional mutagenesis (J. D. Watson et al., supra, p. 261). Viral vectors, and retroviral vectors in particular, are also used in therapeutic applications (e.g., gene therapy), in which a gene (or genes) is added to a cell to replace a missing or defective gene or to inactivate a pathogen such as a virus.

1. Retroviruses

The members of the family Retroviridae are characterized by the presence of reverse transcriptase in their virions. There are several genera included within this family, including Cisternavirus A, Oncovirus A, Oncovirus B, Oncovirus C, Oncovirus D, Lentivirus, and Spumavirus. Some of the retroviruses are oncogenic (i.e., tumorigenic), while others are not. The oncoviruses induce sarcomas, leukemias, lymphomas, and mammary carcinomas in susceptible species. Retroviruses infect a wide variety of species, and may be transmitted both horizontally and vertically. They are integrated into the host DNA, and are capable of transmitting sequences of host DNA from cell to cell. This has led to the development of retroviruses as vectors for various purposes including gene therapy.

2. Gene Therapy

Gene therapy has been investigated as one method to cure disease. Viral vectors transduce genes into target cells with high efficiencies owing to specific virus envelope-host cell receptor interaction and viral mechanisms for gene expression. Factors affecting viral vector usage include tissue tropism, stability of virus preparations, genome packaging capacity, and construct-dependent vector stability. In addition, in vivo application of viral vectors is often limited by host immune responses against viral structural proteins and/or transduced gene products. This host immunity problem plus potential safety concerns about the possibility of generating replication-competent viruses have prompted much effort towards the development of non-viral vector systems, such as liposome-mediated gene transfer, naked DNA injections and gene gun technology. However, all of these non-viral gene transfer methods lack the ability to allow permanent integration of foreign genes into the host cell chromosomes. For long term expression of therapeutic genes in target cells, efficient means of transduction and genome integration are essential. Viral vectors such as retroviruses and adeno-associated viruses (AAV) transduce and integrate genes into different cell and tissue types. Thus, these viral vectors have been useful tools in current clinical gene therapy applications.

3. Retroviral Gene Therapy Strategies

Efficient and long term gene transfer is essential to clinical gene therapy application. Retroviral vectors derived from the amphotropic Moloney murine leukemia virus (MLV-A) use cell surface phosphate transporter receptors for entry and then permanently integrate into proliferating cell chromosomes. The amphotropic MLV vector system has been well established and is a popular tool for gene delivery (See e.g., E. M. Gordon and W. F. Anderson, Curr. Op. Biotechnol., 5:611–616 [1994]; and A. D. Miller et al., Meth. Enzymol., 217:581–599 [1993]).

Other retroviruses, including human foamy virus (HFV) and human immunodeficiency virus (HIV) have gained much recent attention, as their target cells are not limited to dividing cells and their restricted host cell tropism can be readily expanded via pseudotyping with vesicular stomatitis virus G (VSV-G) envelope glycoproteins (See e.g., J. C. Burns et al., Proc. Natl. Acad. Sci. USA 90:8033–8037 [1993]; A. M. L. Lever, Gene Therapy. 3:470–471 [1996]; and D. Russell and A. D. Miller, J. Virol., 70:217–222 [1996]). However, a useful lentiviral vector system has not been well established, mainly because of the lack of sufficient studies on lentiviral vectorology and safety concerns.

4. Gene Therapy Strategies For Inborn Errors Of Metabolism

In a few cases, gene therapy has been used to successfully correct inborn errors of metabolism using existing vector systems. For example, the adenosine deaminase gene has been introduced into peripheral blood lymphocytes and cord blood stem cells via retroviral vectors in order to treat patients with severe combined immunodeficiency due to a lack of functional adenosine deaminase (K. W. Culver et al., Human Gene Ther., 2:107 [1991]). Partial correction of familial hypercholesterolemia has been achieved using existing retroviral vectors to transfer the receptor for low density lipoproteins (LDL) into hepatocytes. However, it was estimated that only 5% of the liver cells exposed to the recombinant virus incorporated the LDL receptor gene with the vector utilized (M. Grossman et al., Nat. Genet., 6:335 [1994]).

A number of single-gene disorders have been targeted for correction using gene therapy. These disorders include hemophilia (lack of Factor VIII or Factor IX), cystic fibrosis (lack of cystic fibrosis transmembrane regulator), emphysema (defective α-1-antitrypsin), thalassemia and sickle cell anemia (defective synthesis of β-globin), phenylketonuria (deficient phenylalanine hydroxylase) and muscular dystrophy (defective dystrophin) (for review see A. D. Miller, Nature 357:455 [1992]). Human gene transfer trials have been approved for a number of these diseases.

5. Gene Therapy Strategies For Cancer

In addition to replacement of defective genes, it has been proposed that viral vectors could be used to deliver genes designed to stimulate immunity against or to otherwise destroy tumor cells. Retroviral vectors containing genes encoding tumor necrosis factor (TNF) or interleukin-2 (IL-2) have been transferred into tumor-infiltrating lymphocytes in patients (A. Kasid et al., Proc Natl Acad Sci USA.

87:473–477 [1990]; and S. A. Rosenberg, Human Gene Therapy 5: 140 [1994]). It is postulated that the secretion of TNF or IL-2 stimulates a tumor-specific immune response resulting in the destruction of the tumor or the recruitment of effective tumor infiltrating lymphocytes from nearby lymph nodes. Other proposed anti-tumor gene therapy strategies include the delivery of toxin genes to the tumor cell.

Applications of antisense genes or antisense oligonucleotides in inhibition of oncogenes and modulation of growth factors have the potential to reduce the mortality of cancer, in particular, human leukemia (For review see, A. M. Gewirtz, Stem Cells 3:96 [1993]; and L. Neckers and L. Whitesell, Amer. J. Physiol., 265:L1 [1993]).

6. Current Viral Vector Systems

In view of the wide variety of potential genes available for therapy, it is clear that an efficient means of delivering these genes is sorely needed in order to fulfill the promise of gene therapy as a means of treating infectious, as well as non-infectious diseases. Several viral systems including murine retrovirus, adenovirus, parvovirus (adeno-associated virus), vaccinia virus, and herpes virus have been developed as therapeutic gene transfer vectors (For review see, A. W. Nienhuis et al., *Hematology*, Vol. 16:*Viruses and Bone Marrow*, N. S. Young (ed.), pp. 353–414 [1993]). Viral vectors provide a more efficient means of transferring genes into cells as compared to other techniques such as calcium phosphate or DEAE-dextran-mediated transfection, electroporation or microinjection. It is believed that the efficiency of viral transfer is due to the fact that the transfer of DNA is a receptor-mediated process (i.e., the virus binds to a specific receptor protein on the surface of the cell to be infected).

While many viral vector systems are available, virtually all of the current human gene therapy trials use retroviral vectors derived from the amphotropic Moloney murine leukemia virus (M-MuLV) for gene transfer (A. D. Miller and C. Buttimore, Mol. Cell. Biol., 6:2895 [1986]). The M-MuLV system has several advantages: 1) this specific retrovirus can infect many different cell types; 2) established packaging cell lines are available for the production of recombinant M-MuLV viral particles; and 3) the transferred genes are permanently integrated into the target cell chromosome. The established M-MuLV vector systems comprise a DNA vector containing a small portion of the retroviral sequence (the viral long terminal repeat or "LTR" and the packaging or "psi" [ψ] signal) and a packaging cell line. The gene to be transferred is inserted into the DNA vector. The viral sequences present on the DNA vector provide the signals necessary for the insertion or packaging of the vector RNA into the viral particle and for the expression of the inserted gene. The packaging cell line provides the viral proteins required for particle assembly (D. Markowitz et al., J. Virol., 62:1120 [1988]).

The vector DNA is introduced into the packaging cell by any of a variety of techniques (e.g., calcium phosphate coprecipitation, electroporation, etc.). The viral proteins produced by the packaging cell mediate the insertion of the vector sequences in the form of RNA into viral particles which are shed into the culture supernatant. The M-MuLV system has been designed to prevent the production of replication-competent virus as a safety measure. The recombinant viral particles produced in these systems can infect and integrate into the target cell but cannot spread to other cells. These safeguards are necessary to prevent the spread of the recombinant virus from the treated patient and to avoid the possibility of helper virus-induced disease (A. D. Miller and C. Buttimore, supra; and D. Markowitz et al., supra).

Despite these advantages, existing retroviral vectors are limited by several intrinsic problems: 1) they do not infect non-dividing cells (D.G. Miller et al., Mol. Cell. Biol., 10:4239 [1990]); 2) they produce only low titers of the recombinant virus (A. D. Miller and G. J. Rosman, BioTechn., 7: 980 [1989]; and A. D. Miller, Nature 357: 455 [1992]); and 3) they express foreign proteins at low levels and often get "turned-off" or inactivated after integration (A. D. Miller, Nature 357: 455 [1992]). The low production of recombinant virus produced by the M-MuLV system (e.g., $10^6$/ml) compared to the adenoviral system (up to $10^{12}$/ml) means that human cells are infected at a very low efficiency. This low efficiency is particularly problematic when the target cell type is represented at very low numbers in the tissue to be infected. Although the hematopoietic stem cell is a preferred target for gene therapy in a large number of disorders, these cells are present at very low frequencies. For example, totipotent embryonic stem cells have been reported to occur at a frequency of $10^{-4}$ to $10^{-6}$ in bone marrow (B. R. Glick and J. J. Pasternak, *Molecular Biotechnology*, American Society for Microbiology, Washington, D.C., p. 412 [1994]). Thus, the low titer produced by existing M-MuLV vector systems is highly problematic for stem cell infection.

In addition, the promoter present in the M-MuLV LTR is quite weak compared with other viral promoters such as the human cytomegalovirus immediate early (CMV-IE) enhancer/promoter. In order to increase expression of the genes carried on the retroviral vector, internal promoters possessing stronger activities than the M-MuLV promoter have been utilized. However, the inclusion of an internal promoter to drive the expression of the inserted gene does not always lead to increased levels of expression (D. Robinson et al., Gene Therapy 2:269 [1995]). Apparently, the activity of the internal promoter is significantly decreased because of interference from the upstream M-MuLV promoter (i.e., transcriptional read-through interference). The dual transcription-unit construct is, however, a common feature in almost all M-MuLV vectors.

Given these limitations, it is clear that improved vector systems are urgently needed to provide a means of delivering and expressing genes efficiently in mammalian cells, particularly human cells. Improved vectors will aid the study of gene expression and development and are necessary if the promise of gene therapy is to be realized.

SUMMARY OF THE INVENTION

The present invention contemplates improved viral vectors useful for the expression of genes at high levels in human and other cells. These vectors also find use in anti-viral, anti-tumor and/or gene therapy. The improved vectors contain novel packaging signals, an internal promoter, and a recombinant Rous sarcoma virus splicing signal that function in a wide variety of human cell types. The improved recombinant vectors also contain sequences which result in increased efficiency of packaging the recombinant viral genome. The viral gene expression vectors (e.g., pHP series), were constructed to contain minimal amounts of HIV sequences, allowing efficient expression of viral structural proteins, but not genome packaging, thereby minimizing the possibilities of recombination. The transducing vectors (e.g., pTVs), were constructed to contain all of the required sequences to allow efficient genome packaging and an internal promoter, but contain no viral genes and minimize the possibility of recombination with pHP. The present invention further provides a recombinant tat-inducible LTR. These two series of vectors have demonstrated efficient gene transduction and high levels of long-term expression in many types of dividing and non-dividing cells, as well as animal tissues.

The present invention provides recombinant lentiviruses, wherein the genome of the recombinant lentivirus comprises at least one artificial nucleic acid sequence wherein the artificial nucleic acid sequence selected from the group comprising an artificial splice donor site, and an artificial gag AUG. In some embodiments, the recombinant lentiviral genome further comprises a deleted 5' non-coding leader region. In yet other embodiments, the recombinant lentiviral genome further comprises a mutated long terminal repeat. In further embodiments, the genome of the recombinant lentivirus further comprises an heterologous internal promoter and gene sequences capable of expressing at least one functional heterologous gene product. The present invention also provides recombinant lentivirus, wherein the genome of the recombinant lentivirus further comprises one or more mutated genes selected from the group consisting of a mutated tat, a mutated nef gene, a mutated env gene, a mutated rev gene, a mutated vif gene, a mutated vpu gene, and a mutated vpr gene. In preferred embodiments, the recombinant lentivirus genome is selected from the group consisting of human immunodeficiency virus type 1, human immunodeficiency virus type 2, feline immunodeficiency virus, simian immunodeficiency virus, visna-maedi, caprine arthritis-encephalitis virus, equine infectious anemia virus, and bovine immune deficiency virus.

The present invention also provides lentiviral vectors, wherein the vector comprises at least a portion of the recombinant lentivirus genome. In preferred embodiments, the recombinant lentiviral genome included within the vector comprises an at least one artificial nucleic acid sequence. In preferred embodiments, the artificial nucleic acid sequence is selected from the group comprising an artificial splice donor site, and an artificial gag AUG. In some embodiments, the recombinant lentiviral genome contained within the lentiviral vector, further comprises a deleted 5' non-coding leader region. In yet other embodiments, the recombinant lentiviral genome contained within the lentiviral vector further comprises a mutated long terminal repeat. In yet other embodiments, the genome of the recombinant lentivirus of the lentiviral vector further comprises an heterologous internal promoter and gene sequences capable of expressing at least one functional heterologous gene product. The present invention also provides lentiviral vectors, wherein the vector contains at least a portion of the genome of a recombinant lentivirus in which the recombinant lentivirus genome comprises one or more mutated genes selected from the group consisting of a mutated tat, a mutated nef gene, a mutated env gene, a mutated rev gene, a mutated vif gene, a mutated vpu gene, and a mutated vpr gene. In preferred embodiments, the recombinant lentivirus genome contained with the lentiviral vector is selected from the group consisting of human immunodeficiency virus type 1, human immunodeficiency virus type 2, feline immunodeficiency virus, simian immunodeficiency virus, visna-maedi, caprine arthritis-encephalitis virus, equine infectious anemia virus, and bovine immune deficiency virus. Thus, the recombinant lentivirus may be recombinant HIV-1, HIV-2, SIV, or a virus comprised of portions of more than one lentiviral species (e.g., a hybrid, comprised of portions of HIV-1 and HIV-2, or HIV-1 and SIV, etc.) In particularly preferred embodiments of the vector, the lentiviral vector comprises SEQ ID NO:13. In yet other embodiments, the lentiviral vector further comprises plasmid DNA selected from the group consisting of pHP-1, pHP-dl.2 and pHP-dl.28, pHP-VSVG, pHP-CMV, pHP-CMVdel.TAR/SD, pHP-CMV-EF1α intron, and pHP-EF.

In some embodiments, the lentiviral vector is contained within a host cell. In preferred embodiments, the lentiviral vector is contained within an eukaryotic host cell. In particularly preferred embodiments, the eukaryotic cell is a human cell. In yet other embodiments, the cell is selected from the group consisting of rodent cells, feline cells, equine cells, ovine cells, caprine cells, bovine cells, and primate cells. In yet other embodiments, the cells are selected from the group consisting of TE671, HepG2, HeLa, 293T, MT4, neuronal cells, and astrocytes. In yet other embodiments, the human cell is selected from the group consisting of muscle cells, white blood cells, spleen cells, liver cells, epithelial cells, and eye cells. However, it is also intended that the present invention encompass lentiviral vectors contained within non-living vessels, including but not limited to syringes, test tubes, centrifuge tubes, etc. It is also intended that the present invention encompass lentiviral vectors present within any type of suspension fluid or liquid, including but not limited to buffers, media (e.g., cell culture media), serum or plasma, serous fluid, etc.

In some embodiments, the lentiviral vectors of the present invention are capable of synthesizing lentiviral structural proteins selected from the group consisting of Gag and Pol. In other embodiments, the lentiviral vectors are further capable of assembling replication-defective lentiviral particles. In some embodiments, the lentiviral vector capable of assembling replication-defective lentiviral particles is a non-inducible vector, while in other embodiments, the lentiviral vector capable of synthesizing lentiviral structural proteins is an inducible vector.

In some embodiments, the lentiviral vectors of the present invention are contained within a packaging cell and/or packaging cell line. In alternative embodiments, the packaging cell and/or cell line produces lentiviral particles in response to at least one inducer. In preferred embodiments, the inducer is Tat. In yet other embodiments, the packaging cell and/or cell line, further contains a transducing vector containing at least one transducing gene. In preferred embodiments, the transducing gene is capable of integrating into the genome of said host cell. In particularly preferred embodiments, the packaging cell produces lentiviral vector progeny. In alternative preferred embodiments, the progeny comprise at least one transducing gene. In yet other preferred embodiments, the lentiviral vector progeny are capable of integrating into the genome of a target cell. In other embodiments, the lentiviral vector progeny are capable of expressing the transducing gene and/or gene product (e.g., the target cell is capable of producing proteins present in the transduced lentiviral vector genome or gene sequences). Thus, it is contemplated that the target cell will produce proteins encoded by the lentiviral vector used to produce the lentiviral progeny. In particularly preferred embodiments, the transducing gene of the lentiviral progeny is capable of long-term expression in a target cell. In some embodiments, the target cell is an eukaryotic cell. In preferred embodiments, the target cell is a human cell. In yet other embodiments, the target cell is selected from the group consisting of rodent cells, feline cells, equine cells, ovine cells, caprine cells, bovine cells, and primate cells. In additional embodiments, the target cells are selected from the group consisting of TE671, HepG2, HeLa, 293T, MT4, neuronal cells, and astrocytes. In yet other embodiments, the human cell is selected from the group consisting of muscle cells, white blood cells, spleen cells, liver cells, epithelial cells, and eye cells.

In some embodiments, the packaging cell and/or cell line contains a transducing vector is selected from the group consisting of pTVψ, pTVψ100, pTVψ140, pTV.ψ.nlacZ, and pTVψCMV-nlacZ-hyg-dl.SmaI, pTVΔ, pTVΔ-X, pTVΔCMV-X, pTVΔCMVnlacZ, pTVΔSVneo, pTVΔSVhyg, pTVΔCMV-GFP, pTVΔCMV-nlacZ, and pTVΔCMV-nlacZ-hyg. In yet other embodiments, the packaging cell produces replication-defective lentivirus particles. In another embodiment, the packaging cell and/or cell line further comprises an expression plasmid suitable for envelope pseudotyping. In preferred embodiments, the expression plasmid is selected from the group consisting of pHEF-VSVG, pHEF.A-env, Gibbon ape leukemia virus env, and MLV-Aenv.

The present invention also provides cells containing at least one lentiviral vector, wherein the lentiviral vector is capable of high efficiency transduction and/or long-term transduction. In some embodiments, the cells containing the high efficiency of transduction and/or long-term transducing lentiviral vectors are non-dividing cells. In yet other embodiments, the cell is selected from the group consisting of human cells, rodent cells, feline cells, equine cells, ovine cells, caprine cells, bovine cells, and primate cells. In yet other embodiments, the cells are selected from the group consisting of TE671, HepG2, HeLa, 293T, MT4, neuronal cells, and astrocytes. In yet other embodiments, the human cell is selected from the group consisting of muscle cells, white blood cells, spleen cells, liver cells, epithelial cells, and eye cells. In particularly preferred embodiments, the vector is capable of transducing a plurality of target cells at an efficiency level of at least $10^5$.

In preferred embodiments, the progeny of the long-term and/or high efficiency transducing lentiviral vector are capable of infecting a target cell. In some embodiments, the target cell is an eukaryotic cell. In preferred embodiments, the target cell is a human cell. In yet other embodiments, the cell is selected from the group consisting of rodent cells, feline cells, equine cells, ovine cells, caprine cells, bovine cells, and primate cells. In yet other embodiments, the cells are selected from the group consisting of TE671, HepG2, HeLa, 293T, MT4, neuronal cells, and astrocytes. In preferred embodiments, the vector progeny of the long-term and/or high efficiency transducing lentiviral vector are capable of transducing a plurality of target cells at an efficiency level of at least $10^5$.

The present invention also provides an attenuated lentivirus, wherein the genome of the attenuated lentivirus comprises a mutated tat gene and a mutated long terminal repeat. In yet other embodiments of the attenuated lentivirus, the viral genome further comprises a mutated nef gene. In some embodiments, the attenuated lentivirus is selected from the group consisting of human immunodeficiency virus type 1, human immunodeficiency virus type 2, feline immunodeficiency virus, simian immunodeficiency virus, visna-maedi, caprine arthritis-encephalitis virus, equine infectious anemia virus, and bovine immune deficiency virus. Thus, the attenuated virus may be an attenuated HIV-1, attenuated HIV-2, attenuated SIV, or a virus comprised of portions of more than one lentiviral species (e.g., a hybrid, comprised of portions of HIV-1 and HIV-2, or HIV-1 and SIV, etc.) The present invention also provides a vector, wherein the vector comprises at least a portion of the attenuated lentivirus. The present invention provides vectors that contain all or part of an attenuated lentivirus, either alone or in combination with other sequences (e.g., heterologous DNA). In some embodiments, the vector containing the attenuated lentivirus is contained within a host cell. In preferred embodiments, the host cell is an eukaryotic cell. In preferred embodiments, the eukaryotic cell is a human cell. In yet other embodiments, the human cell is a non-dividing cell. In further embodiments, the non-dividing cell is selected from the group consisting of neuronal cells and astrocytes. In yet other embodiments, the human cell is selected from the group consisting of muscle cells, white blood cells, spleen cells, liver cells, epithelial cells, and eye cells. In other embodiments, the cell is selected from the group consisting of rodent cells, feline cells, equine cells, ovine cells, caprine cells, bovine cells, and primate cells. In additional other embodiments, the cells are selected from the group consisting of TE671, HepG2, HeLa, 293T, and MT4 cells.

The vector pHP-1dl.2 differs from pHP-1 in that the bases corresponding to bases 6924–6925 of SEQ ID NO:13 are omitted. Similarly, in pHP-1dl.28 those corresponding to bases 6906–6933 are omitted.

Figure 7:
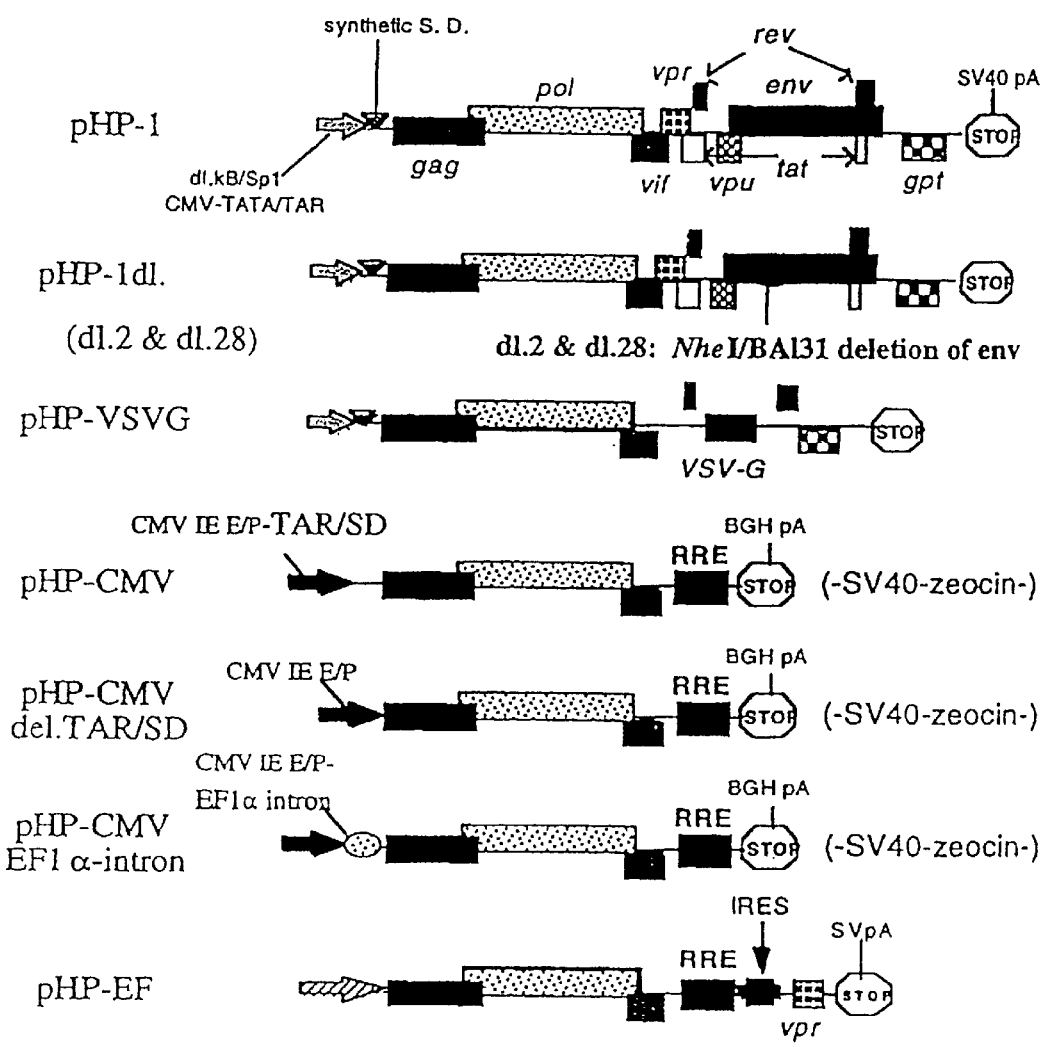

FIG. 7 shows seven pHP-1-derived packaging vector constructs.

Figure 8:
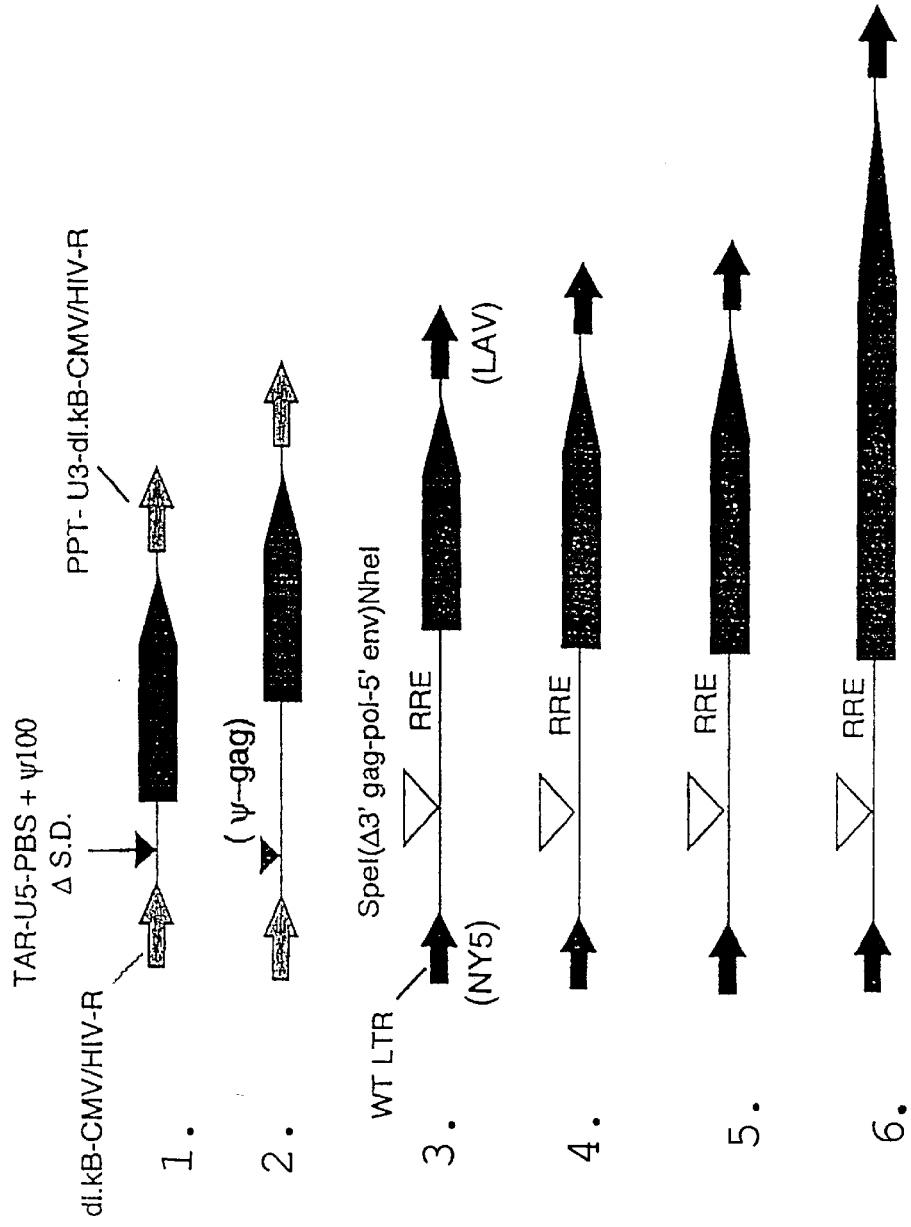

FIG. 8 shows six pTV-derived transducing vector constructs.

Figure 9:
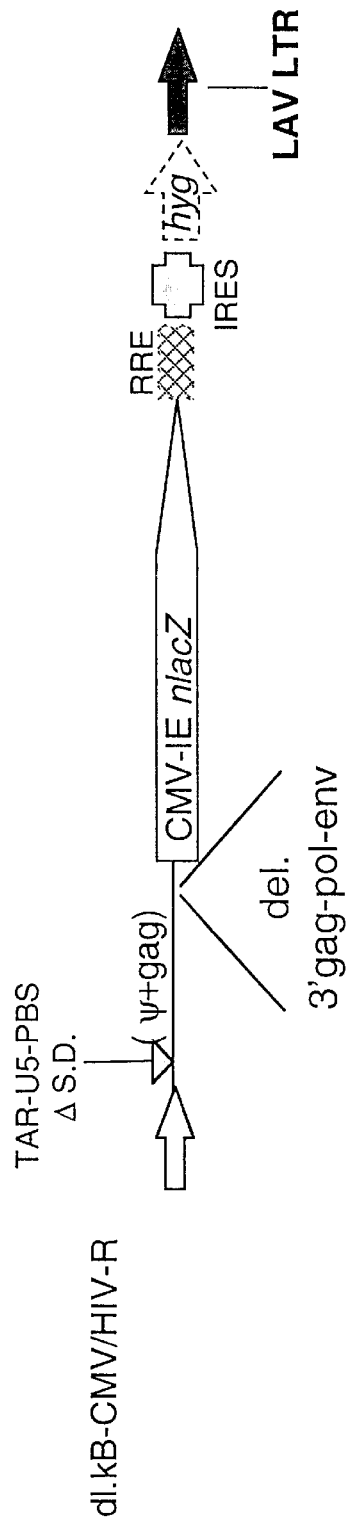
Figure 9:
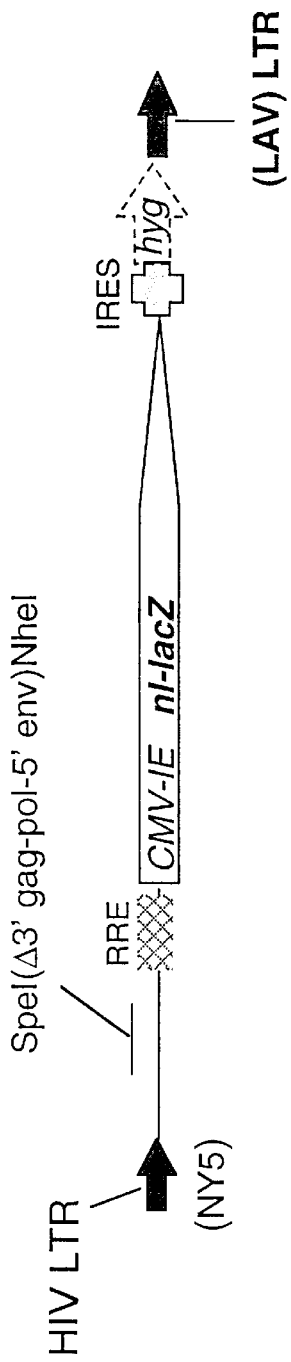

FIG. 9A shows a pTV-derived construct.

FIG. 9B shows a pTVΔ-derived construct.

Figure 10:
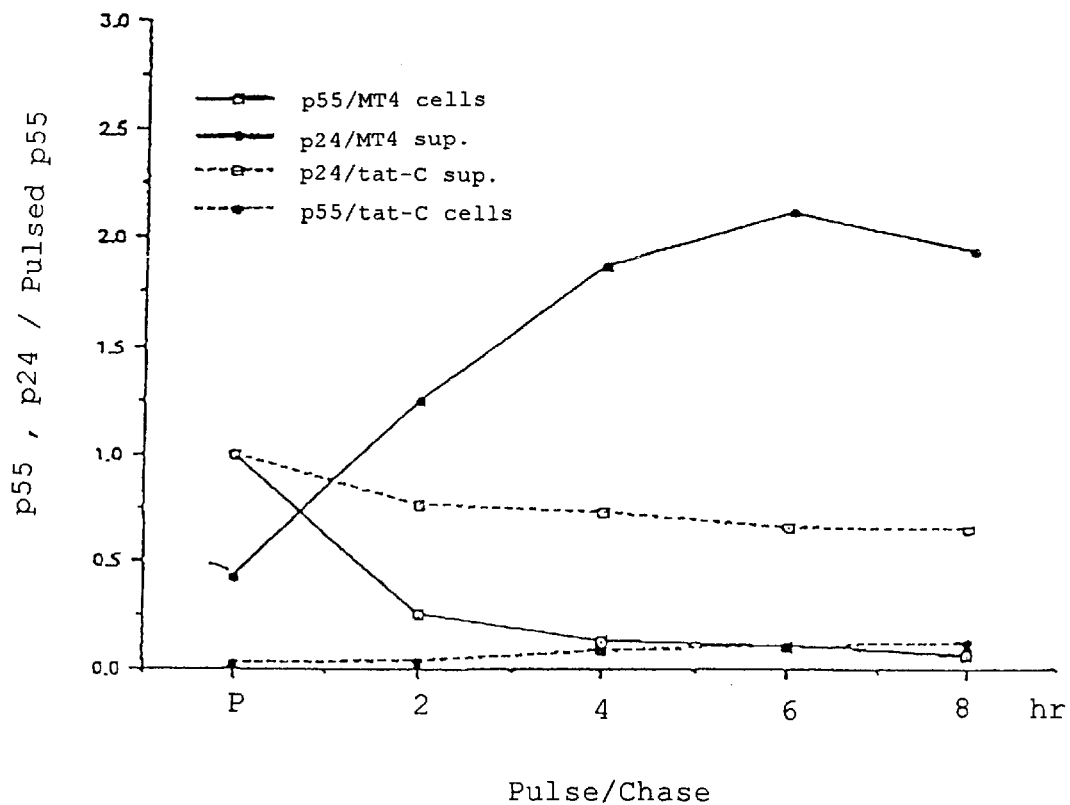

FIG. 10 shows the Gag processing rates of wild-type HIV-infected MT4 compared with tat-C HIV chronic high producing cells.

Figure 11:
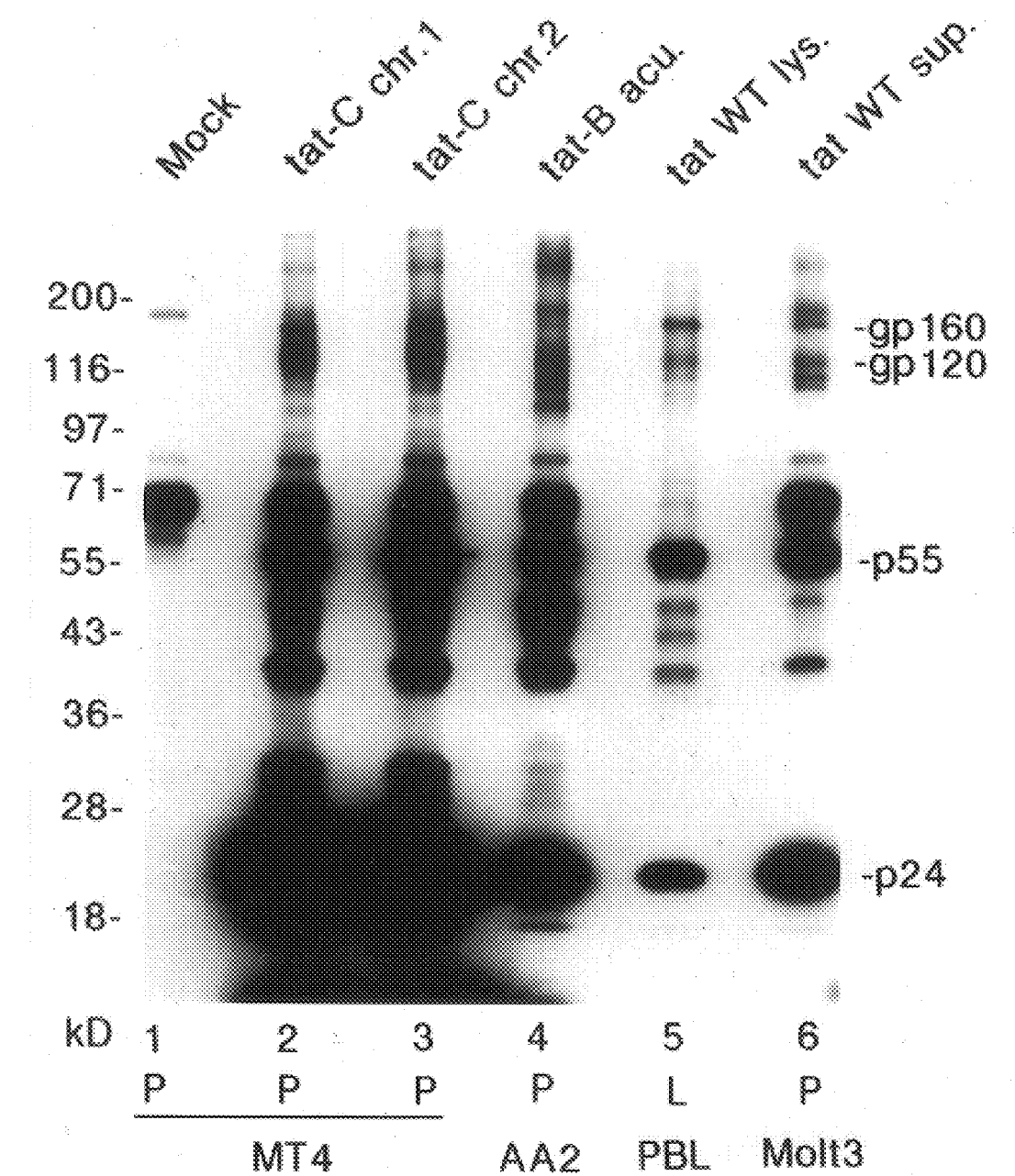

FIG. 11 shows a Western analysis of expression of Tat⁺ and Tat⁻ HIV particles and infected cells.

Figure 12:
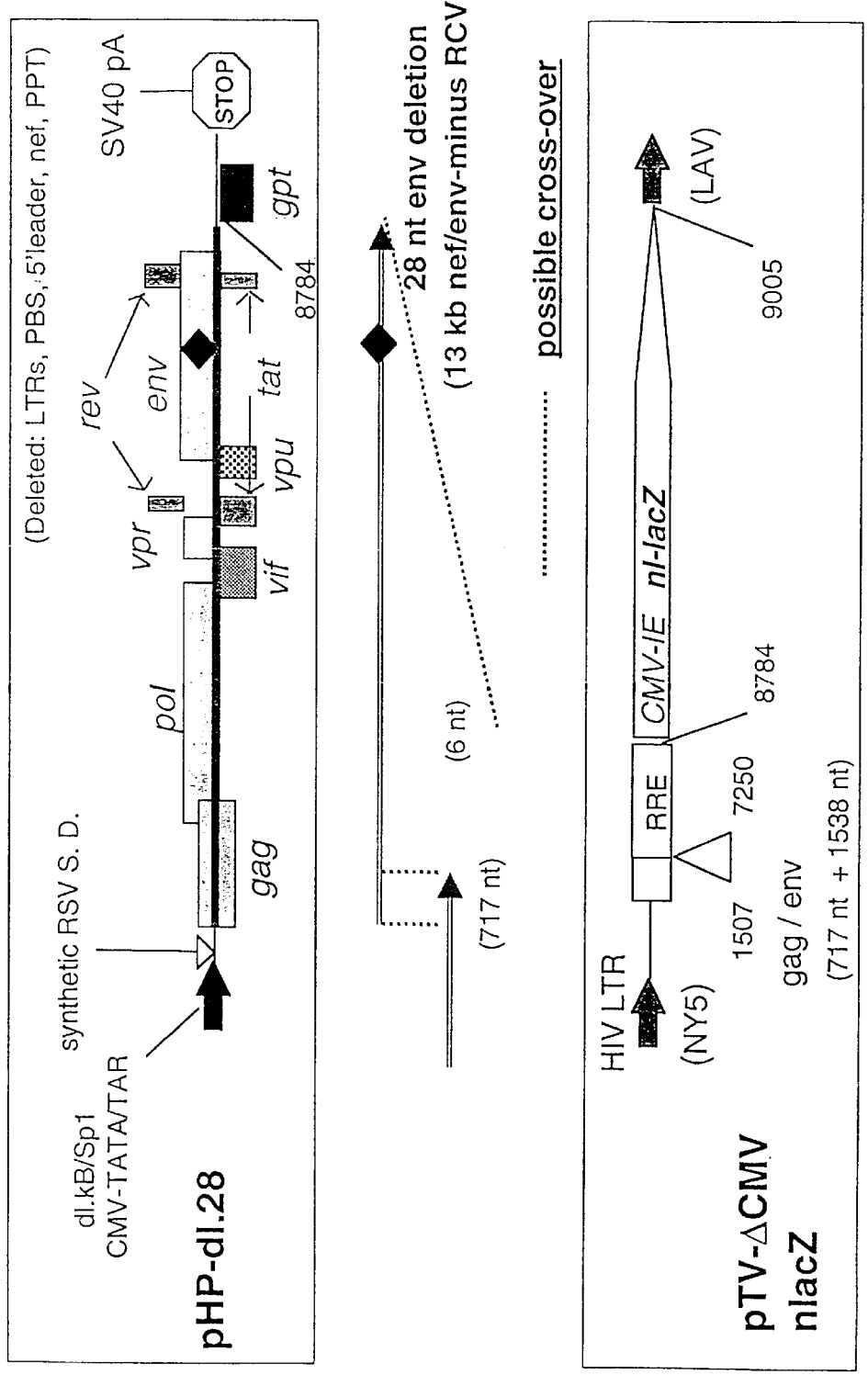

FIG. 12 illustrates the possible cross-over to generate RCV from co-transfection of pHP-dl.28 and pTV-dl.CMVnlacZ.

FIGS. 13A provides a schematic showing a portion of the wild-type HIV-1 sequence, as well as the tat-B (wild-type sequence provided in SEQ ID NO:4; the tat-B sequence is provided in SEQ ID NO:20).

FIG. 13B provides a schematic showing a portion of the wild-type HIV-1 sequence, as well as the nef-A mutations and nef-B mutations (wild-type sequence provided in SEQ ID NOS:5 and 6). The nef-B mutations are shown in SEQ ID NOS:18 and 19). The nef-A sequence is the same as the wildtype sequence for the sequence shown starting at base 9001 (i.e., SEQ ID NO:6 represents the sequences for both wild-type and nef-A). For the sequence shown starting at base 8781, the nef-A sequence is the same as the nef-B sequence shown in SEQ ID NO:5 (i.e., SEQ ID NO:5 represents the sequences for both nef-A and nef-B in the sequence shown starting at base 8781).

Figure 14:
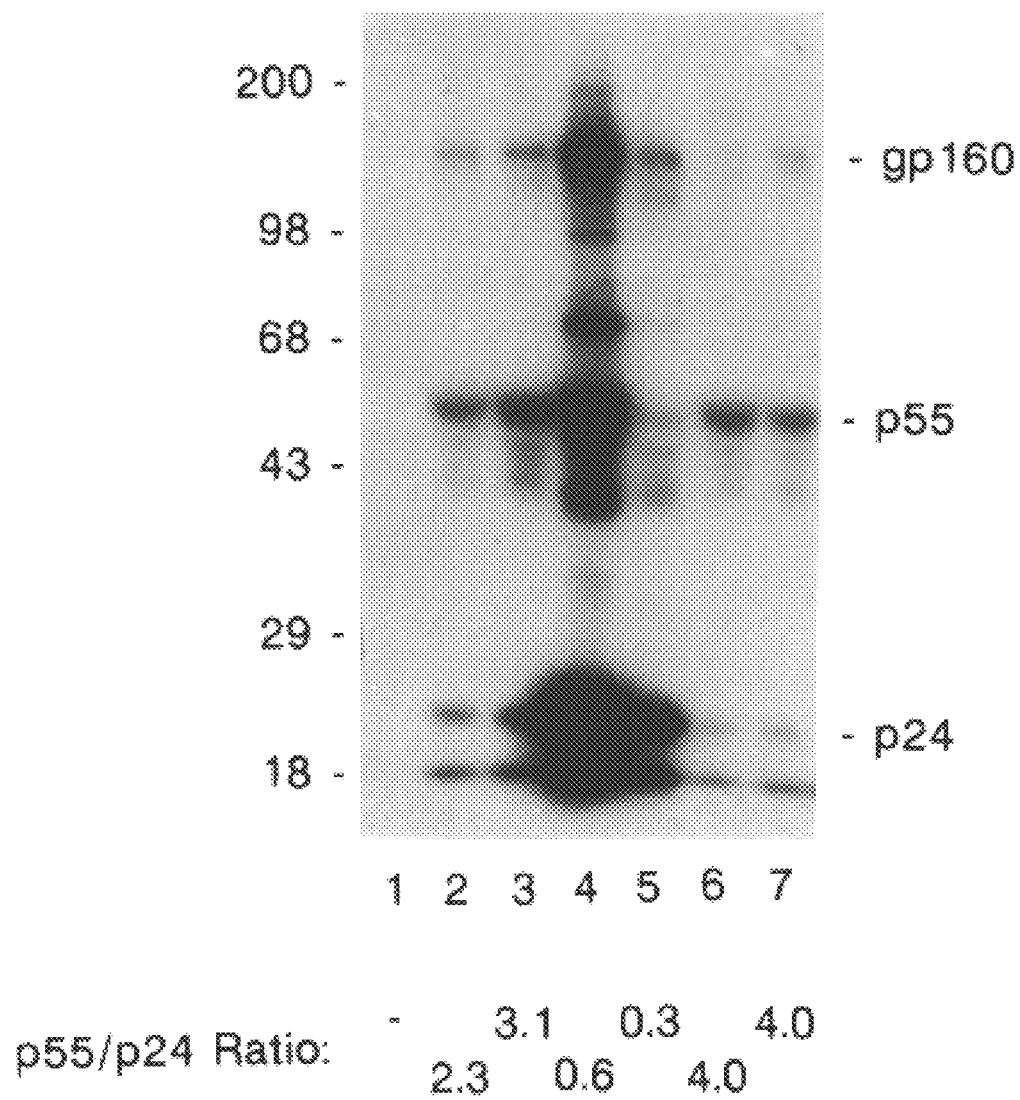

FIG. 14 shows a Western analysis of Gag processing in wild-type or tat⁻ HIV-1 infected cell cultures.

Figure 15:
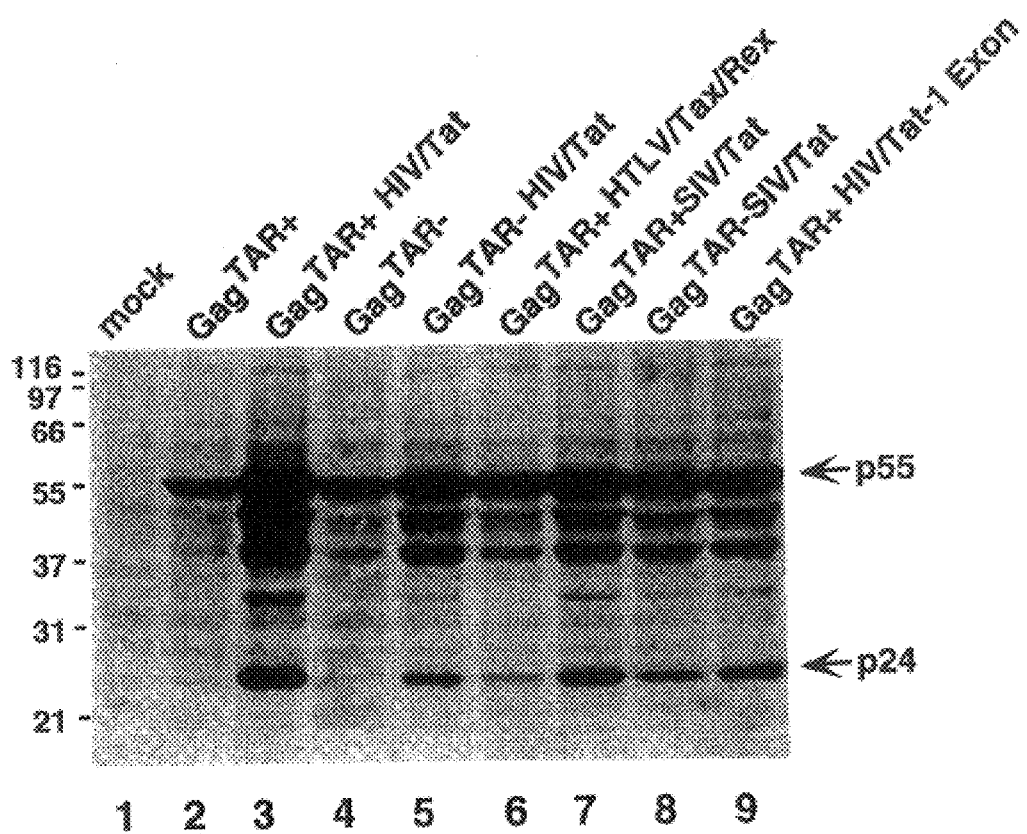

FIG. 15 shows a Western analysis indicating the effect of Tat on Gag processing in infected HeLa cells.

Figure 16:
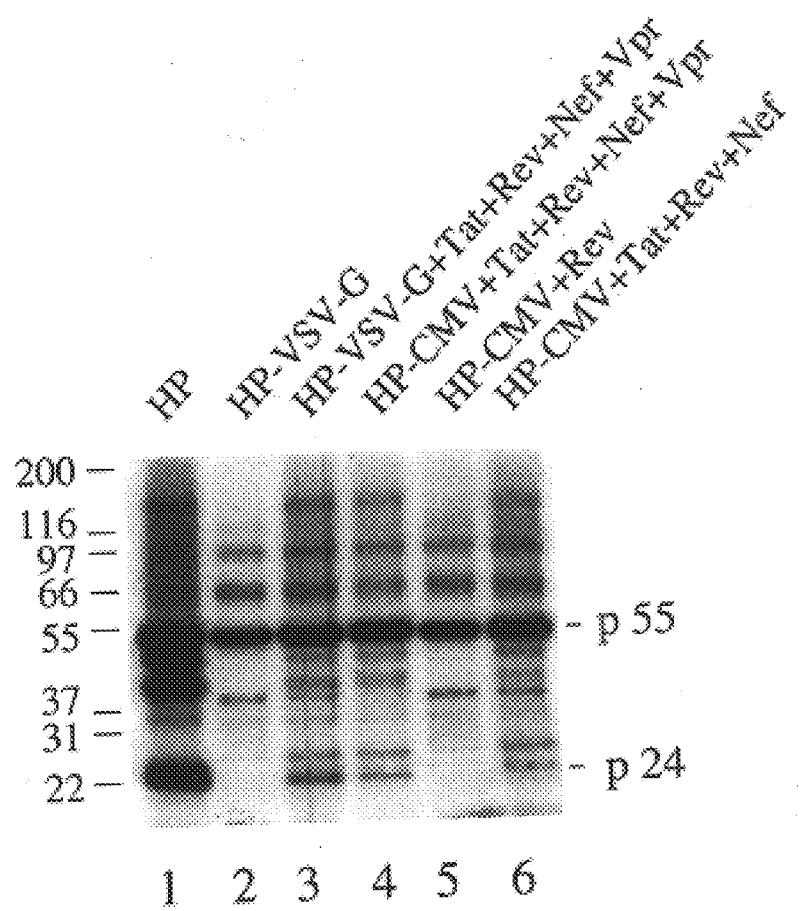

FIG. 16 shows a Western analysis of the effect of Tat on Gag processing in infected TE671 cells.

FIG. 17 provides the sequence of a portion of the wild-type HIV-1 sequence, as well as the tat-B (wild-type sequence provided in SEQ ID NO:4), and tat-A (SEQ ID NO:16), tat-B (SEQ ID NO:20), and tat-C (SEQ ID NO:17).

DEFINITIONS

To facilitate understanding of the invention, a number of terms are defined below.

As used herein, the term "polyA⁺ RNA" refers to RNA molecules having a stretch of adenine nucleotides at the 3' end. this polyadenine stretch is also referred to as a "poly-A tail". Eukaryotic mRNA molecules contain poly-A tails and are referred to as poly$^{A+}$ RNA.

As used herein, the term "trans" is used in reference to the positioning of genes of interest on the different strands of nucleic acid (e.g., alleles present on the two chromosomes of a chromosomal pair). The term "trans-acting" is used in reference to the controlling effect of a regulatory gene on a gene present on a different chromosome. In contrast to promoters, repressors are not limited in their binding to the DNA molecule that includes their genetic information. Therefore, repressors are sometimes referred to as trans-acting control elements.

The term "trans-activation" as used herein refers to the activation of gene sequences by factors encoded by a regulatory gene which is not necessarily contiguous with the gene sequences which it binds to and activates. For example, the HIV-1 regulatory protein Tat is encoded by the tat gene and binds to and activates (i.e., trans-activates) expression from the HIV LTR.

As used herein, the term "cis" is used in reference to the presence of genes on the same chromosome. The term "cis-acting" is used in reference to the controlling effect of a regulatory gene on a gene present on the same chromosome. For example, promoters, which affect the synthesis of downstream mRNA are cis-acting control elements.

As used herein, the term "retrovirus" is used in reference to RNA viruses that utilize reverse transcriptase during their replication cycle. The retroviral genomic RNA is converted into double-stranded DNA by reverse transcriptase. This double-stranded DNA form of the virus is capable of being integrated into the chromosome of the infected cell; once integrated, it is referred to as a "provirus." The provirus serves as a template for RNA polymerase II and directs the expression of RNA molecules which encode the structural proteins and enzymes needed to produce new viral particles. At each end of the provirus are structures called "long terminal repeats" or "LTRs." The LTR contains numerous regulatory signals including transcriptional control elements, polyadenylation signals and sequences needed for replication and integration of the viral genome. The viral LTR is divided into three regions called U3, R and U5.

The U3 region contains the enhancer and promoter elements. The U5 region contains the polyadenylation signals. The R (repeat) region separates the U3 and U5 regions and transcribed sequences of the R region appear at both the 5' and 3' ends of the viral RNA.

As used herein, the term "lentivirus" refers to a group (or genus) of retroviruses that give rise to slowly developing disease. Viruses included within this group include HIV (human immunodeficiency virus; including HIV type 1, and HIV type 2), the etiologic agent of the human acquired immunodeficiency syndrome (AIDS); visna-maedi, which causes encephalitis (visna) or pneumonia (maedi) in sheep, the caprine arthritis-encephalitis virus, which causes immune deficiency, arthritis, and encephalopathy in goats; equine infectious anemia virus, which causes autoimmune hemolytic anemia, and encephalopathy in horses; feline immunodeficiency virus (FIV), which causes immune deficiency in cats; bovine immune deficiency virus (BIV), which causes lymphadenopathy, lymphocytosis, and possibly central nervous system infection in cattle; and simian immunodeficiency virus (SIV), which cause immune deficiency and encephalopathy in sub-human primates. Diseases caused by these viruses are characterized by a long incubation period and protracted course. Usually, the viruses latently infect monocytes and macrophages, from which they spread to other cells. HIV, FIV, and SIV also readily infect T lymphocytes (i.e., T-cells).

Lentivirus virions have bar-shaped nucleoids and contain genomes that are larger than other retroviruses. Lentiviruses use tRNA$^{lys}$ as primer for negative-strand synthesis, rather than the tRNA$^{pro}$ commonly used by other infectious mammalian retroviruses. The lentiviral genomes exhibit homology with each other, but not with other retroviruses (See, Davis et al., *Microbiology*, 4th ed., J.B. Lippincott Co., Philadelphia, Pa. [1990], pp. 1123–1151). An important factor in the disease caused by these viruses is the high mutability of the viral genome, which results in the production of mutants capable of evading the host immune response.

As used herein, the term "attenuated virus" refers to any virus (e.g., an attenuated lentivirus) that has been modified so that it is incapable of causing disease or pathology in a host animal or cell (i.e., it encompasses viruses that are incapable of causing cytopathic effects (CPE) in viral cultures, or that are only able to produce reduced CPE). It is intended that the term encompass viral particles that are not as virulent as wild-type virus. Thus, the term encompasses viral particles that are capable of some degree of infection and gene expression, but are not able to produce disease or productive infection.

The term "gene" refers to a DNA sequence that comprises control and coding sequences necessary for the production of a polypeptide or precursor. The polypeptide can be encoded by a full length coding sequence or by any portion of the coding sequence so long as the desired enzymatic activity is retained.

The term "wild-type" refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product. It is intended that any mutation be encompassed within this definition; it is not intended that the term be limited to mutations that result in the production of genes or proteins that are non-functional.

As used herein, the term "replication-defective" refers to virus that is not capable of complete, effective replication such that infective virions are not produced (e.g. replication-defective lentiviral progeny). The term "replication-competent" refers to wild-type virus or mutant virus that is capable of replication, such that viral replication of the virus is capable of producing infective virions (e.g., replication-competent lentiviral progeny).

As used herein, the term "tat" is used in reference to the HIV gene which encodes "Tat," a protein which induces high-level expression of HIV genes.

As used herein, the term "long terminal repeat (LTR)" is used in reference to domains of base pairs located at the ends of retroviral DNAs. These LTRs may be several hundred base pairs in length. LTRs often provide functions fundamental to the expression of most eukaryotic genes (e.g., promotion, initiation and polyadenylation of transcripts).

As used herein, the term "TAR" is used in reference to the "trans-activation response" genetic element located in the U5 region of the HIV LTR. This element mediates the action of tat, by physically binding to the viral trans-activator tat.

As used herein, the term "adoptive transfer" is used in reference to the transfer of one function to another cell or organism. For example, in "adoptive immunity," transfer of an immune function is made from one organism to another through the transfer of immunologically competent cells.

As used herein, the term "endogenous virus" is used in reference to an inactive virus which is integrated into the chromosome of its host cell (often in multiple copies), and can thereby exhibit vertical transmission. Endogenous viruses can spontaneously express themselves and may result in malignancies.

As used herein, the terms "amphotrope" and "amphotropic" are used in reference to endogenous viruses that readily multiply in cells of the species in which they were induced, as well as cells of other species.

As used herein, the term "ecotrope" and "ecotropic" are used in reference to endogenous viruses that multiply readily in cells of the species in which they were induced, but cannot multiply in cells of other species.

As used herein, the term "xenotrope" and "xenotropic" are used in reference to endogenous viruses that cannot infect cells of the species in which they were induced, but can infect and multiply in cells of other species.

As used herein, the term "provirus" is used in reference to a virus that is integrated into a host cell chromosome (or genome), and is transmitted from one cell generation to the next, without causing lysis or destruction of the host cell. The term is also used in reference to a duplex DNA sequence present in an eukaryotic chromosome, which corresponds to the genome of an RNA retrovirus.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro.

The term "T25 flask" refers to a tissue culture flask having a growth surface area of 25 square centimeters.

As used herein, the term "packaging signal" or "packaging sequence" refers to sequences located within the retroviral genome which are required for insertion of the viral RNA into the viral capsid or particle. Several retroviral vectors use the minimal packaging signal (also referred to as the psi [ψ] sequence) needed for encapsidation of the viral genome. This minimal packaging signal encompasses bases 212 to 563 of the Mo-MuLV genome (Mann et al., Cell 33:153 [1983]). Thus, as used herein, the terms "packaging sequence," "packaging signal," "psi" and the symbol "ψ," are used in reference to the non-coding sequence required for encapsidation of retroviral RNA strands during viral particle formation.

As used herein, the term "extended packaging signal" or "extended packaging sequence" refers to the use of sequences around the psi sequence with further extension into the gag gene. In Mo-MuLV, this extended packaging sequence corresponds to the region encompassing base 1039 to base 1906 (T. Akagi et al., Gene 106:255 [1991]. The frequently used M-MuLV vector, pLNL6 (M. A. Bender et al., J. Virol. 61:1639[1987]), contains the entire 5' region of the genome including an extended packaging signal from bases 206 to 1039 of the Moloney murine sarcoma virus genome (numbering from Supplements and Appendices in RNA Tumor Viruses, 2nd ed. [1985] pp. 986–988). The inclusion of these additional packaging sequences increases the efficiency of insertion of vector RNA into viral particles As used herein, the term "packaging cell lines" is used in reference to cell lines that express viral structural proteins (e.g., gag, pot and env), but do not contain a packaging signal. For example, a cell line has been genetically engineered to carry at one chromosomal site within its genome, a 5'-LTR-gag-pol-3'-LTR fragment that lacks a functional psi+sequence (designated as Δpsi), and a 5'-LTR-env-3'-LTR fragment which is also Δpsi located at another chromosomal site. While both of these segments are transcribed constitutively, because the psi+region is missing and the viral RNA molecules produced are less than full-size, empty viral particles are formed.

It is contemplated that packaging may be inducible, as well as non-inducible. In inducible packaging cells and packaging cell lines, lentiviral particles are produced in response to at least one inducer. In preferred embodiments with inducible cell lines, the inducer is Tat. In non-inducible packaging cell lines and packaging cells, no inducer is required in order for lentiviral particle production to occur.

When retroviral vector DNA is transfected into the cells, it may or may not become integrated into the chromosomal DNA and is transcribed, thereby producing full-length retroviral vector RNA that has a psi$^+$ sequence. Under these conditions, only the vector RNA is packaged into the viral capsid structures These complete, yet replication-defective, virus particles can then be used to deliver the retroviral vector to target cells with relatively high efficiency.

As used herein, the term "remedial gene" refers to a gene whose expression is desired in a cell to correct an error in cellular metabolism, to inactivate a pathogen or to kill a cancerous cell. For example, the adenosine deaminase (ADA) gene is the remedial gene when carried on a retroviral vector used to correct ADA deficiency in a patient.

As used herein, the term "selectable marker" refers to the use of a gene which encodes an enzymatic activity that confers resistance to an antibiotic or drug upon the cell in which the selectable marker is expressed. Selectable markers may be "dominant"; a dominant selectable marker encodes an enzymatic activity which can be detected in any eukaryotic cell line. Examples of dominant selectable markers include the bacterial aminoglycoside 3' phosphotransferase gene (also referred to as the neo gene) which confers resistance to the drug G418 in mammalian cells, the bacterial hygromycin G phosphotransferase (hyg) gene which confers resistance to the antibiotic hygromycin and the bacterial xanthine-guanine phosphoribosyl transferase gene (also referred to as the gpt gene) which confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene which is used in conjunction with tk⁻ cell lines, the CAD gene which is used in conjunction with CAD-deficient cells and the mammalian hypoxanthine-guanine phosphoribosyl transferase (hprt) gene which is used in conjunction with hprt⁻ cell lines. A review of the use of selectable markers in mammalian cell lines is provided in Sambrook, J. et al., *Molecular Cloning: A Laboratory Manual*, 2nd ed., Cold Spring Harbor Laboratory Press, New York [1989] pp.16.9–16.15.

As used herein, the term "retroviral vector" is used in reference to modified retroviruses used as vectors for introduction of nucleic acid into cells.

As used herein, the term "vector" is used in reference to nucleic acid molecules that transfer nucleic acid (e.g., DNA) segment(s) from one cell to another. The term "vehicle" is sometimes used interchangeably with "vector." It is intended that any form of vehicle or vector be encompassed within this definition. For example, vectors include, but are not limited to viral particles, plasmids, transposons, etc.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals. In some embodiments, "expression vectors" are used in order to permit pseudotyping of the viral envelope proteins.

The terms "in operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "genetic cassette" as used herein refers to a fragment or segment of DNA containing a particular grouping of genetic elements. The cassette can be removed and inserted into a vector or plasmid as a single unit.

The term "transfection" as used herein refers to the introduction of foreign DNA into eukaryotic cells. Transfection may be accomplished by a variety of means known to the art including but not limited to calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

As used herein, the term "transduction" refers to the delivery of a gene(s) using a viral or retroviral vector by means of infection rather than by transfection. In preferred embodiments, retroviral vectors are transduced. For example, an anti-HIV gene carried by a retroviral vector can be transduced into a cell through infection and provirus integration. Thus, a "transduced gene" is a gene that has been introduced into the cell via lentiviral or vector infection and provirus integration. In preferred embodiments, viral vectors (e.g., "transducing vectors") transduce genes into "target cells" or host cells.

In the present invention, various transducing vectors may be used, including pTVψ, pTVψ100, pTVψ140, pTVψ.nlacZ, and pTVψCMV-nlacZ-hyg-dl.SmaI, pTVΔ, pTVΔ-X, pTVΔCMV-X, pTVΔCMVnlacZ, pTVΔSVneo, pTVΔSVhyg, pTVΔCMV-GFP, pTVΔCMV-nlacZ, and pTVΔCMV-nlacZ-hyg. However, it is not intended that the present invention be limited to these specific transducing vectors. For example, the "pTVΔ-X," indicates that the vector may be comprised of "pTVΔ" in combination with any gene ("X"). Thus, the present invention encompasses transducing vectors that are suitable for use in the present invention that are linked to any gene of interest (or a "marker gene" or "reporter gene," used to indicate infection or expression of a gene).

In preferred embodiments, the vectors of the present invention are capable of "high efficiency transduction." This is intended to encompass transducing vectors capable of transduction at a level of at least $10^5$/ml, although in particularly preferred embodiments, the vectors are capable of transduction levels of up to $10^9$/ml. As used herein, the term "low efficiency transduction" refers to transducing vectors capable of transduction at levels less than or equal to $10^3$/ml.

As used herein, the term "long-term transduction" refers to vectors that are capable of remaining transduced in host or target cells for time periods that are longer than those observed with other vectors. For example, the present invention provides lentiviral vectors that are capable of remaining transduced for 48 days. Long-term gene transduction and high efficiencies of transduction of human cells by the HIV vectors of the present invention were compared with the conventional MLV vector (See, Table 5).

The term "stable transduction" or "stably transduced" refers to the introduction and integration of foreign DNA into the genome of the transducted cell. The term "stable transductant" refers to a cell which has stably integrated foreign DNA into the genomic DNA.

The term "transient transduction" or "transiently transduced" refers to the introduction of foreign DNA into a cell where the foreign DNA fails to integrate into the genome of the transducted cell. The foreign DNA persists in the nucleus of the transducted cell for several days. During this time the foreign DNA is subject to the regulatory controls that govern the expression of endogenous genes in the chromosomes. The term "transient transductant" refers to cells which have taken up foreign DNA but have failed to integrate this DNA.

In some preferred embodiments, the target and/or host cells of the present invention are "non-dividing" cells. These cells include cells such as neuronal cells that do not normally divide. However, it is not intended that the present invention be limited to non-dividing cells (including, but not limited to muscle cells, white blood cells, spleen cells, liver cells, eye cells, epithelial cells, etc.).

As used herein, the term "TATA element" or "TATA box" is used in reference to a segment of DNA, located approximately 19–27 base pairs upstream from the start point of eukaryotic structural genes, to which RNA polymerase binds. The TATA box is approximately 7 base pairs in length, often comprising the sequence "TATAAAA."

The TATA box is also sometimes referred to as the "Hogness box." The term "CAAT box" or "CAAT element" refers to a conserved DNA sequence located approximately 75 bp upstream from the start point of eukaryotic structural genes, to which RNA polymerase binds.

As used herein, the terms "complementary" or "complementarity" are used in reference to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the Tm of nucleic acids is well known in the art. As indicated by standard references, a simple estimate of the Tm value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in *Nucleic Acid Hybridization* [1985]). Other references include more sophisticated computations which take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less.

As used herein, the term "amplifiable nucleic acid" is used in reference to nucleic acids which may be amplified by any amplification method. It is contemplated that "amplifiable nucleic acid" will usually comprise "sample template."

As used herein, the term "sample template" refers to nucleic acid originating from a sample which is analyzed for the presence of "target" (defined below). In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, which is capable of hybridizing to another oligonucleotide of interest. Probes are useful in the detection, identification and isolation of particular gene sequences. It is contemplated that any probe used in the present invention will be labelled with any "reporter molecule," so that is detectable in any detection system, including, but not limited to enzyme (e.g., ELISA, as well as enzyme-based histochemical assays), fluorescent, radioactive, calorimetric, and luminescent systems. It is further contemplated that the oligonucleotide of interest (i.e., the oligonucleotide to be detected) will be labelled with a reporter molecule. It is also contemplated that both the probe and oligonucleotide of interest will be labelled. It is not intended that the present invention be limited to any particular detection system or label.

The term "label" as used herein refers to any atom or molecule which can be used to provide a detectable (preferably quantifiable) signal, and which can be attached to a nucleic acid or protein. Labels may provide signals detectable by fluorescence, radioactivity, colorimetry, gravimetry, X-ray diffraction or absorption, magnetism, enzymatic activity, and the like.

As used herein, the term "target," when used in reference to amplificaiton methods such as PCR, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the method of U.S. Pat. Nos. 4,683,195 4,683,202, and 4,965,188 to K. B. Mullis and Mullis et al., all of which are hereby incorporated by reference, and describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (D. L. Kacian et al., Proc. Nat. Acad. Sci USA 69:3038[1972]). Other nucleic acid will not be replicated by this amplification enzyme. Similarly, in the case of T7 RNA polymerase, this amplification enzyme has a stringent specificity for its own promoters (M. Chamberlin et al., Nature 228:227[1970]). In the case of T4 DNA ligase, the enzyme will not ligate the two oligonucleotides where there is a mismatch between the oligonucleotide substrate and the template at the ligation junction (D. Y. Wu and R. B. Wallace, Genomics 4:560[1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press [1989]).

Some amplification techniques take the approach of amplifying and then detecting target; others detect target and then amplify probe. Regardless of the approach, nucleic acid must be free of inhibitors for amplification to occur at high efficiency.

As used herein, the terms "PCR product" and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "nested primers" refers to primers that anneal to the target sequence in an area that is inside the annealing boundaries used to start PCR (See e.g., K. B. Mullis, et al., Cold Spring Harbor Symposia, Vol. II, pp.263–273[1986]). Because the nested primers anneal to the target inside the annealing boundaries of the starting primers, the predominant PCR-amplified product of the starting primers is necessarily a longer sequence, than that defined by the annealing boundaries of the nested primers. The PCR-amplified product of the nested primers is an amplified segment of the target sequence that cannot, therefore, anneal with the starting primers. Advantages to the use of nested primers include the large degree of specificity, as well as the fact that a smaller sample portion may be used and yet obtain specific and efficient amplification.

As used herein, the term "amplification reagents" refers to those reagents (deoxyribonucleoside triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule which is comprised of segments of DNA joined together by means of molecular biological techniques. In some preferred embodiments of the present invention, the recombinant DNA molecule comprises attenuated lentiviral particles.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the term "an oligonucleotide having a nucleotide sequence encoding a gene" means a DNA sequence comprising the coding region of a gene or in other words the DNA sequence which encodes a gene product. The coding region may be present in either a cDNA or genomic DNA form. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "transcription unit" refers to the segment of DNA between the sites of initiation and termination of transcription and the regulatory elements necessary for the efficient initiation and termination. For example, a segment of DNA comprising an enhancer/promoter, a coding region and a termination and polyadenylation sequence comprises a transcription unit.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc. (defined infra).

Transcriptional control signals in eukaryotes comprise "promoter" and "enhancer" elements. Promoters and enhancers consist of short arrays of DNA sequences that interact specifically with cellular proteins involved in transcription (T. Maniatis et al., Science 236:1237 [1987]). Promoter and enhancer elements have been isolated from a variety of eukaryotic sources including genes in yeast, insect and mammalian cells and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (for review, see, S. D. Voss et al., Trends Biochem. Sci., 11:287 [1986]; and T. Maniatis et al., supra [1987]). For example, the SV40 early gene enhancer is very active in a wide variety of cell types from many mammalian species and has been widely used for the expression of proteins in mammalian cells (R. Dijkema et al., EMBO J. 4:761 [1985]). Two other examples of promoter/enhancer elements active in a broad range of mammalian cell types are those from the human elongation factor 1a gene (T. Uetsuki et al., J. Biol. Chem., 264:5791[1989]; D. W. Kim et al., Gene 91:217 [1990]; and S. Mizushima, and S. Nagata, Nuc. Acids. Res., 18:5322 [1990]) and the long terminal repeats of the Rous sarcoma virus (C. M. Gorman et al., Proc. Natl. Acad. Sci. USA 79:6777 [1982]) and the human cytomegalovirus (M. Boshart et al., Cell 41:521 [1985]).

As used herein, the term "promoter/enhancer" denotes a segment of DNA which contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) such that transcription of that gene is directed by the linked enhancer/promoter.

The term "factor" refers to a protein or group of proteins necessary for the transcription or replication of a DNA sequence. For example, SV40 T antigen is a replication factor which is necessary for the replication of DNA sequences containing the SV40 origin of replication. Transcription factors are proteins which bind to regulatory elements such as promoters and enhancers and facilitate the initiation of transcription of a gene.

Promoters and enhancers may bind to specific factors which increase the rate of activity from the promoter or enhancer. These factors may be present in all cell types or may be expressed in a tissue-specific manner or in virus infected cells. In the absence of such a factor the promoter may be inactive or may produce a low level of transcriptional activity. Such a low level of activity is referred to as a baseline or "basal" rate of activity. Additionally, viral promoter and enhancers may bind to factors encoded by the virus such that the viral promoter or enhancer is "activated" in the presence of the viral factor (in a virus infected cell or in a cell expressing the viral factor). The level of activity in the presence of the factor (ie., activity "induced" by the factor) will be higher than the basal rate.

Different promoters may have different levels of basal activity in the same or different cell types. When two different promoters are compared in a given cell type in the absence of any inducing factors, if one promoter expresses at a higher level than the other it is said to have a higher basal activity.

The activity of a promoter and/or enhancer is measured by detecting directly or indirectly the level of transcription from the element(s). Direct detection involves quantitating the level of the RNA transcripts produced from that promoter and/or enhancer. Indirect detection involves quantitation of the level of a protein, often an enzyme, produced from RNA transcribed from the promoter and/or enhancer. A commonly employed assay for promoter or enhancer activity utilizes the chloramphenicol acetyltransferase (CAT) gene. A promoter and/or enhancer is inserted upstream from the coding region for the CAT gene on a plasmid; the plasmid is introduced into a cell line. The levels of CAT enzyme are measured. The level of enzymatic activity is proportional to the amount of CAT RNA transcribed by the cell line. This CAT assay therefore allows a comparison to be made of the relative strength of different promoters or enhancers in a given cell line. When a promoter is said to express at "high" or "low" levels in a cell line this refers to the level of activity relative to another promoter which is used as a reference or standard of promoter activity.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is one which is isolated from one gene and placed 3' of another gene. A commonly used heterologous poly A signal is the SV40 poly A signal. The SV40 poly A signal is contained on a 237 bp Bam HI/Bcl I restriction fragment and directs both termination and polyadenylation (J. Sambrook et al., supra, at 16.6–16.7).

Eukaryotic expression vectors may also contain "viral replicons "or "viral origins of replication." Viral replicons are viral DNA sequences which allow for the extrachromosomal replication of a vector in a host cell expressing the appropriate replication factors. Vectors which contain either the SV40 or polyoma virus origin of replication replicate to high copy number (up to $10^4$ copies/cell) in cells that express the appropriate viral T antigen. Vectors containing the replicons from bovine papillomavirus or Epstein-Barr virus replicate extrachromosomally at low copy number (~100 copies/cell).

The term "stable transfection" or "stably transfected" refers to the introduction and integration of foreign DNA into the genome of the transfected cell. The term "stable transfectant" refers to a cell which has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells which have taken up foreign DNA but have failed to integrate this DNA.

As used herein, the term "gene of interest" refers to the gene inserted into the polylinker of an expression vector. When the gene of interest encodes a gene which provides a therapeutic function (such as an anti-HIV gene), the gene of interest may be alternatively called a remedial gene.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "lipofection" refers to a technique for the introduction of nucleic acids into a cell. Lipofection utilizes a liposome formulation of cationic lipids such as N-[1-(2, 3-dioleyloxy)propyl]-N,N,N-trimethylammonium chloride or the polycationic lipid 2,3-dioleyloxy-N-[2 (sperminecarboxamido)ethyl]-N,N-dimethyl-1-propanaminiumtrifluoroacetate and a neutral lipid such as dioleoyl phosphatidylethanolamine. The liposomes complex with nucleic acids and the liposome-nucleic acid complex is used to facilitate the introduction of the nucleic acids into cells. Lipofectin™ Reagent and LipofectAMINE™ Reagent are commercially available from Life Technologies, Inc., Gaithersburg, Md. Lipofection is carried using either of these reagents according to the manufacturer's protocols.

The term "calcium phosphate co-precipitation" refers to a technique for the introduction of nucleic acids into a cell. The uptake of nucleic acids by cells is enhanced when the nucleic acid is presented as a calcium phosphate-nucleic acid coprecipitate. The original technique of Graham and van der Eb (Graham and van der Eb, Virol. 52:456 [1973]) has been modified by several groups to optimize conditions for particular types of cells. The art is well aware of these numerous modifications.

The term "Northern Blot" as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook et al., *Molecular Cloning: A Laboratory Manual*, Cold Spring Harbor Press, Cold Spring Harbor, N.Y., pp 7.39–7.52) The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., *Molecular Cloning: A Laboratory Manual*, Cold Spring Harbor Press, N.Y., pp 9.31–9.58 [1989]).

The term "Western blot" refers to the analysis of protein (s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including enzyme-based detection methods, as well as the use of radiolabelled antibodies.

DESCRIPTION OF THE INVENTION

The invention provides novel lentiviral vectors having improved vector titer, expression from inserted genes, and increased packaging efficiency. These novel vectors are suitable for the introduction and expression of genes at high levels in human cells as well as for anti-viral therapy and general gene therapy applications.

The present invention provides methods and compositions for the use of lentiviral vector constructs derived from HIV type 1 (HIV-1), HIV type 2 (HIV-2), and SIV for long-term gene transfer into human cells and tissues, as well as high titer lentiviral vector production. In addition, the present invention facilitates elucidation of in vitro and in vivo transduction events in dividing and non-dividing human cells containing lentiviral vectors. Several sensitive assay systems for the detection of replication-competent recombinant HIV (RC-HIV) from vector DNA transfected packaging cells and vector transduced human cells were developed, and the replication potential of HIV-1/human endogenous retrovirus (HERV) recombinants evaluated.

A. Simple retroviral vector systems.

Retroviral vectors commonly used for gene transfer are derived from the amphotropic murine leukemia virus (MLV-A) which infects cells of different species. The elements essential to the retroviral vector system are viral structural proteins Gag, Pol and Env, the long terminal repeats (LTR), the reverse transcription templates including primer binding site (PBS) and polypurine tract (PPT), and the packaging signals (psi [ψ]). The MLV-A vector system is comprised of a packaging cell line expressing Gag, Pol and Env, and a vector construct containing LTRs, PBS, PPT and the packaging signal sequences. Up to 8 kbp of foreign sequences can be inserted into the MLV vector and packaged into virus particles. The commonly used amphotropic MLV packaging cell lines such as PA317, PG-13, ψ-CRIP, GP-AM12 and FLY-A13 produce $10^5$–$10^7$ transducing units per ml after vector DNA transfection (F.-L. Cosset et al., J. Virol., 69:7430–7436 [1995]; H. Kotani et al., Human Gene Ther., 5:19–28[1994]; J. S. Lam et al., Human Gene Ther., 7:1415–1422 [1996]; D. Markowitz et al., J. Virol., 62:1120–1124 [1988]; A. D. Miller and F. Chen, J. Virol., 70:5564–5571[1996]).

After selection, producer cell clones can be established to generate $10^4$–$10^6$ transducing units per ml. Increased transduction efficiencies may be achieved by modification of the transduction protocols through means such as repetitive infection steps, cocultivation with the producer cell line, centrifugation, and modification of the culture conditions using growth factors and fibronectin etc. (H. Kotani et al., Human Gene Ther., 5:19–28 [1994]; and T. Moritz et al., Blood 88:855–862 [1996]).

One significant limitation in the simple retroviral vector system is the instability of the enveloped virus particles, as it is both difficult to concentrate in vitro and difficult to manipulate in vivo (A. D. Miller, Nature 357:455–460 [1992]). The MLV LTR activity is also known to be suppressed in embryonal cells (P.M. Challita et al., J. Virol., 69:748–755 [1995]; and T. P. Loh et al., J. Virol., 62:4086–4095 [1988]). In addition, long term expression after viral integration is often restricted by transcription repression, likely due to DNA methylation (J. Boyes and A. Bird, Cell 64:1123–1134 [1991]; and M. Szyf et al., Mol. Cell. Biol., 10:4396–4400 [1990]).

The major limitation in the use of the simple retroviral vectors in gene transfer is that use of the MLV-based vector is restricted to dividing cells. This led to the development of the present invention, in which lentiviruses, capable of infecting non-dividing cells are provided.

B. Complex Retroviral Vector Systems (e.g., Lentiviral Vector Systems) Lentiviruses including HIV, SIV, feline immunodeficiency virus (FIV) and equine infectious anemia virus (EIAV) depend on several viral regulatory genes in addition to the simple structural gag-pol-env genes for efficient intracellular replication. Thus, lentiviruses use more complex strategies than classical retroviruses for gene regulation and viral replication, with the packaging signals apparently spreading across the entire viral genome. These additional genes display a web of regulatory functions during the lentiviral life cycle. For example, upon HIV-1 infection, transcription is up-regulated by the expression of Tat through interaction with an RNA target (TAR) in the LTR. Expression of the full-length and spliced mRNAs is then regulated by the function of Rev which interacts with RNA elements present in the gag region and in the env region (RRE) (S. Schwartz et al., J. Virol., 66:150–159 [1992]). Nuclear export of gag-pol and env mRNAs is dependent on the Rev function. In addition to these two essential regulatory genes, a list of accessory genes, including vif vpr, vpx, vpu, and nef are also present in the viral genome and their effects on efficient virus production and infectivity have been demonstrated, although they are not absolutely required for virus replication (K. and F. Wong-Staal, Microbiol. Rev., 55:193–205 [1991]; R. A. Subbramanian and E. A. Cohen, J. Virol. 68:6831–6835 [1994]; and D. Trono, Cell 82:189–192 [1995]).

HIV-1 infects activated and resting lymphocytes, terminally differentiated monocytes and neuronal cells through cellular receptors and co-receptors such as CD4, chemokine receptors and galactosyl ceramide (J. M. Harouse et al., Science 253:320–323 [1991]; and R. A. Weiss, Science 272:1885–1886 [1996]). The restricted lentiviral host cell tropism can be expanded by pseudotyping the virus particles with broadly tropic viral envelope proteins from human T cell leukemia virus type I (HTLV-I), amphotropic MLV envelope protein or the vesicular stomatitis virus G glycoprotein (J. C. Burns et al., Proc. Natl. Acad. Sci. USA. 90:8033–8037 [1993]; N. R. Landau et al., J. Virol., 65:162–169 [1991]; K. A. Page et al., J. Virol., 64:5270–5276 [1990]; and D. H. Spector et al., J. Virol., 64:2298–2308 [1990]). Alternatively, a CD4 receptor can be introduced into target cells by adenovirus transduction before HIV vector transduction in a two-step transduction protocol (K. Miyake et al., Human Gene Ther., 7:2281–2286 [1996]). Naldini et al. have demonstrated that HIV-1 vectors pseudotyped with MLV-A or VSV-G envelope could produce up to $5\times10^5$ transducing units/ml of vectors capable of infecting non-dividing cells such as macrophages and terminally differentiated neurons (L. Naldini et al., Science 272:263–267. [1996]).

One difficulty related to HIV vector development encountered during the development of the present invention is the cytotoxicity of many HIV gene products to human cells. In particular, it has been difficult to establish continuous cell lines expressing the essential structural proteins Gag, Pol and Env for particle assembly. Cell lines expressing Tat, Rev, Nef have been established. However, expression of Gag, Rev and Vpr has been shown to induce cytopathology, cell death and cell cycle arrest in human cells (See, M. Emerman, Curr. Biol., 6:1096–1103 [1996]; G. Miele and A. M. L. Lever, Gene Ther., 3:357–361 [1995]; and T. Nosaka et al., Exp. Cell. Res,. 209:89–102 [1993]). The development of a tight inducible system was required for the establishment of a lentiviral packaging cell line (H. Yu et al., J. Virol., 70:4530–4537 [1996]). HIV-1 Vpr also induces apoptosis in human cells. The expression of VSV-G protein induces syncytium formation which again is problematic for establishing a packaging cell line.

Infection of nondividing cells by lentiviruses such as HIV-1 is mediated by the nuclear localization signal (NLS) in the Gag MA protein (M.I. Bukrinsky et al., Nature 365:666–669 [1993]). Efficient viral entry and integration into non-dividing cells may also require some of the accessory gene products such as Vpr (T. M. Fletcher et al., EMBO J., 15:6155–6165 [1996]; and N. K. Heinzinger et al., Proc. Natl. Acad. Sci. USA. 91:7311–7315 [1994]). Further studies of the roles of these additional lentiviral genes in transduction of dividing and non-dividing cells were considered to be critical to the development of an efficient as well as safe lentiviral vector system, as provided by the present invention.

In addition, preliminary experiments during the development of the present invention demonstrated that the ψ sequence alone, is not sufficient for genome packaging, and the sequence upstream of the PPT near 3' of the viral genome is critical for vector production. To maximize both the efficiency and safety in the lentiviral vector design, it was considered to be important to determine what effects the different accessory genes or sequences have on vector production and gene transduction.

In these experiments, both the packaging and the transducing vectors (e.g. pHP and pTV series of HIV-1 constructs) were tested, to determine whether co-expression of regulatory or accessory gene functions could increase the transduction efficiency. Accessory gene function such as vpr or vpx may increase transduction efficiency of nondividing cells. The incorporation ability of SIV or HIV-2 Vpx into HIV-1 particles was also examined. Additional packaging signals including tat and rev splice junctions, env and RRE sequences, or sequences upstream of PPT were also cloned into the transducing vectors and tested.

In contrast to previously developed HIV vectors, the constructs provided in the present invention resemble the wild-type HIV-1 genome and retain most of the accessory gene functions. Because of the possible pathogenicity associated with HIV-1 proteins, the strict balance between retained and deleted viral genes in the packaging constructs was evaluated. In addition, the present invention also provides compositions and methods for the development of SIV or EIAV-based lentiviral vectors. These vectors avoid the potential risk of HIV infection with HIV-based vectors.

C. Host Immune Responses in Human Gene Therapy Applications

Gene therapy applications in humans have always met with problems associated with the host immune responses against the gene delivery vehicles or the therapeutic gene products. Viral vectors (e.g., adenovirus) which co-transduce several viral genes together with the therapeutic gene(s) are particularly problematic. For example, readministration is necessary for adenovirus vectors because of the transient nature of viral gene expression. As such, a host immune response to the vector or the therapeutic gene product may be detrimental (B. C. Trapnell and M. Gorziglia, Curr. Op. Biotechnol., 5:617–625 [1994]; and S. K. Tripathy et al., Nature Med., 2:545–550[1996]). Although retroviral vectors do not carry any viral genes in the transducing vector, lentiviruses such as HIV-1 are known to induce strong cell-mediated immune responses upon transient exposure (M. Clerici et al., J. Inf. Dis., 165:1012–1019[1992]; M. Clerici et al., J. Amer. Med. Assoc., 271:42–46 [1994]; L. A. Pinto et al., J. Clin. Invest., 96:867–876 [1995]; and S. Rowland-Jones et al., Nature Med., 1:59–64[1995]). This does not appear to be as critical for retroviral vectors, including the lentiviral vectors, as they do not encode any viral genes in the transducing vector. Another important issue related to the lentiviral vector usage is that of possible cytopathogenicity upon exposure to some cytotoxic viral proteins. Exposure to HIV-1 proteins may induce cell death or functional unresponsiveness in T cells (N. Chirmule et al., J. Virol., 69:492–498 [1995]; C. J. Li et al., Science 268:429–431 [1995]; J. D. Lifson et al., Science 232:1123–1127 [1986]; I. G. Macreadie et al., Mol. Microbiol., 19:1185–1192 [1996]; and T. Nosaka et al., Exp. Cell. Res., 209:89–102 [1993]). Experimental tissue culture systems and animal models (See e.g., U.S. patent application Ser. No. 08/848,760, herein incorporated by reference) to study these issues were used in the development of the safe lentiviral vector systems of the present invention.

D. The Safety Concerns with Lentiviral Vectors

A great concern with the use of lentiviral vectors, and HIV in particular, has been the generation of replication-competent HIV (RC-HIV). While the vector constructs are replication-defective, the risk of generating RC-HIV is increased with the DNA co-transfection procedure, when a high frequency of recombination events can occur at both DNA and RNA levels. Thus, the packaging constructs and the transducing vectors of lentiviruses could potentially recombine and generate replication-competent viruses (RCV) as do the MLV vectors during co-transfection. However, the chances of generating RCV are reduced if multiple recombination steps are necessary, and if the key envelope gene of HIV-1 is deleted.

Due to the restricted tissue tropism of the native lentiviral env gene, lentiviral vectors were developed that use a pan-tropic envelope gene such as amphotropic MLV env or VSV-Gs. This reduced the possibility of producing a wild-type lentiviral RCV (e.g., an HIV-1 Env-trophic virus). However, it is still possible that an RCV could be generated via recombination with these pan-tropic env genes or endogenous retrotransposon env genes. The fact that human genomes carry numerous human endogenous retroviral sequences (HERVS) further increases the probability of generating a fortuitous recombinant RCV (T. P. Loh et al., J. Virol., 62:4086–4095[1988]). For example, a recent study demonstrated that a member of the HERV family encodes a protein resembling the lentivirus rev gene product with a nucleolar localization signal, a putative RNA binding domain, and a sequence similar to the Rev effector domain consensus sequence (R. Lower et al., J. Virol., 69:141–149 [1995]).

Some human tissues and cell lines such as the placenta, syncytiotrophoblasts, brain, differentiated U-937 cells, teratocarcinomas, and the mammary carcinoma T47D cells have been shown to express complete human endogenous retrovirus env gene and release retrovirus-like particles. These endogenous retroviruses may form defective particles which lack infectivity. Although the possibility of generating a recombinant RC-HIV with an HERV env gene is low, it was considered reasonable to formally examine this possibility using an artificial construct with careful management. This was considered to be critical prior to the use of lentiviral vectors in clinical applications.

The generation of RC-HIV can be detected by several sensitive in vitro assays. RC-HIV can also be studied in an in vivo model by transduction of humanized SCID/beige mice. In the latter model, a long in vivo incubation time can be performed, mimicking the situation that exists in a human clinical trial. In addition, the possibility of generating HIV/HERV recombinants may be carefully tested using an artificially constructed HIV/HERV-env recombinant.

Thus, experiments conducted during the development of the present invention allowed examination of the possibility of generating RC-HIV from cultured human cells co-transfected with different pHP and pTV constructs and from humanized SCID/beige mice injected with lentiviral vectors. The replication potential of HIV/HERV-env recombinants were examined directly.

Once a feasible lentiviral vector system was established and tested in the in vitro and in vivo experimental models as described in the Examples, continued efforts were taken to evaluate the safety and immunogenicity of the vector in the host. One of the key issues in human gene therapy is the toxicity and safety to the treatment subjects. During the development of the present invention, it was observed that direct gene transfer into tissue culture cells by the calcium-phosphate DNA co-precipitation method could induce more than 80% cell death which is caused mainly by necrosis and a residual percentage, approximately 2–4%, by programmed cell death. The cytotoxicity associated with viral vector-mediated gene transfer in humans is often caused by a strong host immune response to viral antigens, as is often seen with the in vivo adenoviral gene transfer studies. Although MLV vectors have not been reported to induce cytotoxicity and do not elicit strong host immune responses, lentiviral vectors such as HIV-1 which carry several immunostimulatory gene products may cause cytotoxicity and induce strong immune responses in vivo.

First, the cytotoxicity associated with MLV-A (amphotrophic env MLV), MLV-G (VSV-G MLV), and lentiviral vectors in tissue culture was examined. This was followed by in vivo studies of cytotoxicity and cell-mediated immune (CMI) responses using the humanized SCID/beige mouse model. Thus, the cytotoxicity and immunogenicity of lentiviral vectors in tissue culture and in humanized-mice, respectively, were evaluated. These evaluations included studies of cell death effects in tissue culture and humoral and cellular immune responses to lentiviral vectors both in a peripheral blood lymphocyte culture system and in humanized SCID/beige mice.

The present invention provides modified, safe lentiviral vector systems based on attenuated HIV-1, HIV-2, and SIV. These vector systems were characterized using different in vivo and in vitro models.

E. Retroviral Vectors

Most of the currently approved gene therapy protocols utilize amphotropic M-MuLV-based vectors, such as pLNL6 (Genbank Accession #M63653); M. A. Bender et al., J. Virol. 61:1639 [1987]; SEQ ID NO:1). Accumulated experience with this vector has led to the realization that the activity of the M-MuLV LTR is not very strong. In addition, the activity of this LTR in different cell types is unpredictable.

To create an improved retroviral vector suitable for a wide variety of gene expression studies and gene therapy applications, the clinically approved gene therapy vector pLNL6 has been modified to allow synthesis of high basal levels of mRNA, and increased packaging efficiency (See e.g., co-pending U.S. patent application Ser. No. 08/336, 132, now U.S. Pat. No. 5,698,508, and PCT/US95/14576, to Chang, herein incorporated by reference). The present invention provides new HIV-based vectors with increased efficiency and stability, as shown in the Examples.

F. Attenuated Recombinant HIV-1 Constructs

Although lentiviral vectors have important features such as the ability to transduce non-dividing cells, lentiviruses like HIV-1 are known to be cytopathic and cause AIDS in humans. Nevertheless, through an understanding of the pathogenesis factors in HIV infection, it was possible to reduce the risk of developing a harmful HIV vector. In addition, HIV type 2 (HIV-2) is known to be less pathogenic than HIV-1 in humans, and HIV-2 infection is associated with natural protection against HIV-1 infection. Simian immunodeficiency virus (SIV) also infects human cells; however, it is unclear whether it can cause AIDS in humans. Thus, during early development of the present invention, both HIV-2 and SIV were considered to perhaps better candidates than HIV-1 for developing lentiviral vectors.

It was determined that a reasonable step in designing a safe HIV-1 vector was to distinguish the replication factors from the pathogenesis factors in the viral life cycle and then specifically delete the pathogenic genes from the vector system. For example, SIV and HIV attenuated mutants missing several accessory genes, such as nef; vif vpr, vpx or vpu, have been constructed and their effectiveness against AIDS have been studied in non-human primate models (R. C. Desrosiers, Res. Hum. Retroviruses 8:1457 [1992]; and M. Wyand et al., J. Virol., 70:3724–3733 [1996]). Besides deleting the non-essential viral accessory genes, further attenuation was accomplished by mutating the essential regulatory elements of HIV genome such as LTR, tat and rev. For example, LTR and tat mutants of HIV-1 have been shown to have diminished replication phenotypes (See e.g., L. -J. Chang et al., J Virol., 67:743–752 [1993]; L. -J. Chang and C. Zhang, Virol., 211:157–169 [1995]; and J. C. Leonard et al., J Virol. 63:4919–4924 [1989]).

As described below, several modified HIV-1 constructs which exhibit reduced cytopathic effects in tissue culture were chosen for use in the development of the present invention.

HIV-1 LTR Mutants.

Investigation of virus attenuation was essential to the understanding of viral pathogenesis, the development of preventive vaccines, and development of a safe lentiviral vector system. For production of a safe HIV vector, attenuated mutant molecular constructs of HIV-1 were viewed as better starting materials than wild-type constructs.

One approach to developing these attenuated constructs was establishing mutations in the LTRs of HIV-1. For example, the function of HIV-1 LTR enhancer/promoter elements has been studied using recombinant LTRs containing heterologous enhancer/promoters (See, FIG. 1). After deleting the regulatory elements including the NF-kB, Spl-binding sites, and/or the TATA box, and inserting a minimal cytomegalovirus enhancer element, delayed replication kinetics has been observed in some CD4+ human lymphoid cell lines (See e.g., L. -J. Chang et al., J Virol., 67:743–752 [1993]). However, these LTR mutations do not severely affect the replication of the full-length HIV-1 constructs in tissue culture. Although NF-KB and Sp1 binding sites in the HIV-1 LTR are not absolutely required for viral replication and pathogenicity in vivo, a correlation of LTR mutations with low viral load and prolonged asymptomatic state has been observed for isolates of long term survivors of HIV-1 infection.

It was also found that several LTR deletion mutants containing a cytomegalovirus enhancer element were capable of attenuating HIV-1 (i.e., the mutants were capable of infecting human lymphocytes with reduced cytopathic effects when the gene also was deleted). Instead of killing the entire culture, infection with these LTR and tat mutants led to rapid cell recovery and establishment of persistent infection. The replication efficiency was not markedly affected by these mutations. By mutating the tat gene, it was also found that the recombinant LTRs (CMV-IE-HIV-LTR) exhibited increased basal levels of promoter activity which could support virus replication without Tat (L. -J. Chang, and C. Zhang, Virol., 211:157–169[1995]; and D. Robinson et al., Gene Ther., 2:269–278 [1995]). These different HIV-1 mutant constructs were useful for the development of lentiviral vectors.

Replication-Competent tat-Minus Mutants.

LTR mutants with kB/Spl or Sp1 deletion and CMV-IE enhancer/promoter insertion have been shown to replicate with delayed kinetics in human lymphocyte culture, including primary PBLs (peripheral blood lymphocytes) and macrophages (L. -J. Chang et al., J Virol., 67:743–752 [1993]; and L. -J. Chang and C. Zhang, Virol., 211:157–169 [1995]). As they still exhibit cytopathic effects in culture and thus may be pathogenic in vivo, these constructs are not safe for vaccine use in the present form.

The tat gene was also a target, as it is a gene that is essential for efficient HIV-1 replication. HIV-1 Tat has been implicated in the induction of Kaposi's sarcoma, repression of MHC Class I gene promoter, induction of functional unresponsiveness of T cells, modulation of monocyte function, induction of IL-10 expression, potentiating TNF-induced NF-KB activation and cytotoxicity, and sensitizing T cells to Fas-mediated apoptosis (L. -J. Chang et al., J Virol., 67:743–752; N. Chirmule et al., J Virol. 69:492–498 [1995]; B. Ensoli et al., Nature. 371:674–680[1994]; T. K. Howcroft et al., Science. 260:1320–1322 [1993]; R. M. Lafrenie et al., J. Immunol., 156:1638–1645 [1996]; M. O. Westendorp et al., Nature 375:497–500[1995]; and M. O. Westendorp et al., EMBO J., 14:546–554 [1995]). To examine whether Tat could be dispensable during HIV-1 replication, a series of tat mutants (two stop-codon mutants, tat-A & B, and a deletion mutant tat-C) were investigated (See, FIG. 13A). In FIG. 13A, the dashes (i.e., ----) indicate bases that are shared with the wild-type sequence, while slashes, (i.e., ////) indicate bases that are deleted in the mutant sequence, but are present in the wild-type sequence.

Mutant constructs containing both LTR and tat mutations were established. These LTR/tat double mutants were generated using the LTR mutant constructs which exhibited enhanced transcriptional activity after inserting heterologous enhancer elements. The recombinant LTR (CMV-IE-HIV-LTR), which has been shown to exhibit increased basal level of promoter activity, can support HIV-1 replication without Tat (L. -J. Chang and C. Zhang, Virol., 211:157–169 [1995]; D. Robinson et al., Gene Therap., 2:269–278 [1995]).

During the development of the present invention, it was determined that the tat-C mutant is more defective than the tat-A and -B mutants, and the dl.Sp1/CMV tat-B double mutant is more defective than the dl.Sp1/CMV LTR mutant or the dl.Sp1/CMV tat-A double mutant reported previously (L. -J. Chang and C. Zhang, Virol., 211:157–169 [1995]). The dl.Sp1/CMV tat-B double mutant infects human lymphoid cell lines with delayed kinetics and exhibited reduced cytopathic effects.

In addition, this double mutant HIV-1 infected primary human PBLs poorly and replicated in primary macrophage culture with reduced kinetics. Based on these results, these already attenuated HIV-1 constructs, dl.Sp1/CMV tat-B and dl.Sp1/CMV tat-C, were chosen for HIV vector development.

Attenuated LTR/tat Double Mutants.

Figure 1A:
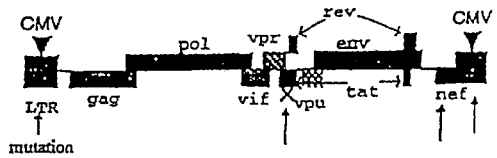
FIG. 1A is a simplified schematic illustration showing the HIV-1 genomic structure.
Figure 1B:
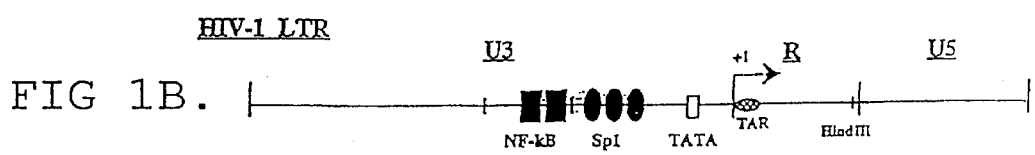
FIG. 1B is a simplified schematic illustration of the HIV-1 LTR.
Figure 1C:
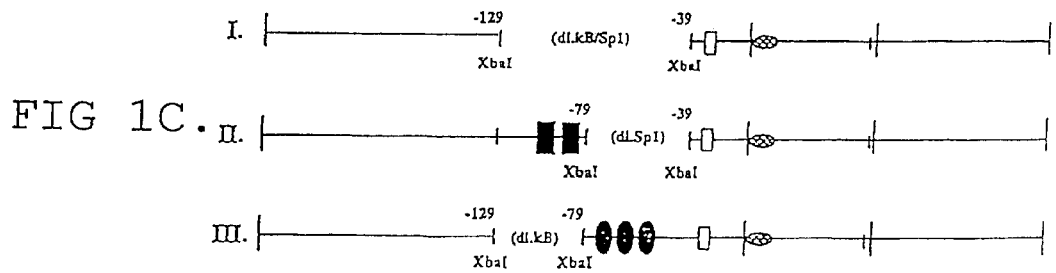
FIG. 1C provides simplified schematic illustrations of three HIV-1 LTR deletion constructs.
Figure 1C:
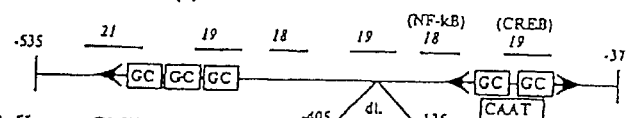
Figure 1D:
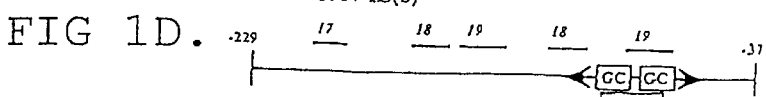
FIG. 1D provides simplified schematic illustrations of three heterologous enhancer/promoter inserts (human CMV IE(a), human CMV IE(b), and Mo-MLV).
Figure 1D:
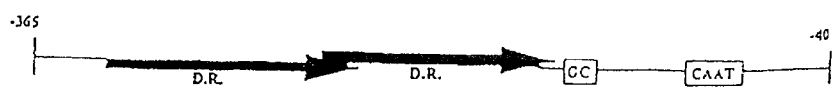
Figure 2:
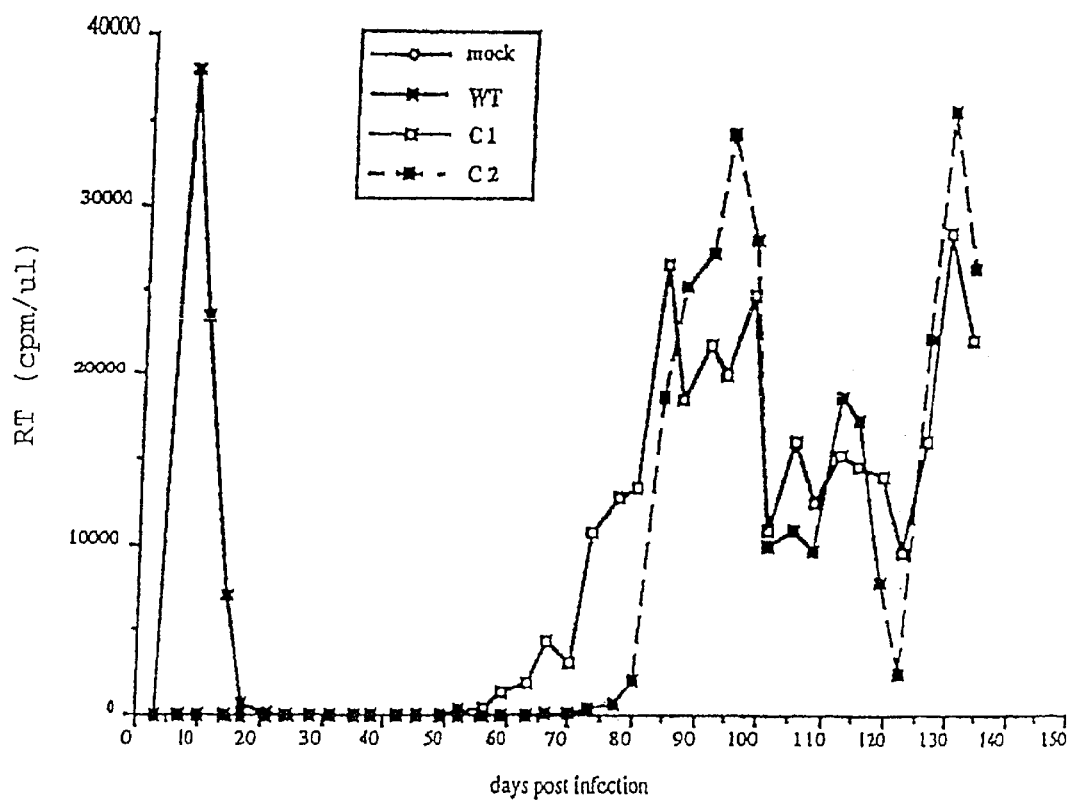
FIG. 2 is a graph showing the reverse transcriptase activity of a representative attenuated recombinant HIV-1 tat mutants over time (days post-infection).

The phenotypes of the LTR/tat mutants were further characterized in hunan lymphoid cell culture. The tat-A or tat-B LTR double mutants (Sp1 deleted and CMV-IE enhancer inserted) infected human MT4 cells with slightly reduced cytopathic effects. Further, these mutants exhibited delayed replication kinetics when compared with wild-type HIV-1. On the other hand, when cells were infected with the tat-C LTR mutant (Sp1/CMV mutant), the cytopathic effect was not so apparent and interestingly, the infected culture recovered rapidly and a persistent infection was established (See, "chr.1" and "chr. 2," in FIG. 2 and Table 1). In this table, as well as other Figures, descriptions, etc., "chr." indicates chronic infection, while the 1 and 2 indicate that the experiment was repeated twice (i.e., the "1" refers to the results of the first experiment, and the "2" refers to the results of the second experiment). In this table, the first column lists the cell line used and the virus used to infect the cells. For example, "MT4/mock" means that MT4 cells were tested without infection with HIV-1 virus (i.e., it was a control). "WT" refers to wild-type virus.

Immunofluorescent staining of cells in the persistent culture using an HIV-1 patient's sera showed that every cell was infected. Continuous output of attenuated infectious virus from these cultures was illustrated by a titration assay on CD4 HeLa cells, and the virus particles were visualized by electron microscopy (TEM and SEM). The persistently infected culture produced large quantities of fully assembled HIV particles. Virions produced from these high producer cells are tat-minus and exhibit greatly diminished infectivity. No cytopathic effect has been observed when they were further passed onto human lymphocyte cultures. Interestingly, some cultures recovered from wild-type HIV-1 infection after long term passage also became persistently infected (See, Table 1, AA2/WT [chr.] and Molt3/WT [chr.]). It is possible that the latter persistent cultures were survivors of mutant HIV-1 infection (e.g., vpr-minus).

TABLE 1

Viability and Doubling Time of Tat +/− HIV-1 Infected Cultures

| Cell Line/Virus | % Viability (±5%) | Doubling Time (±2 hrs) |
| --- | --- | --- |
| MT4/(mock) | 88 | 40 |
| MT4/WT (acute) | 0 | —[a] |
| MT4/tat-A (dl.Sp1/CMV) | 0 | — |
| MT4/tat-B (Dl.Sp1/CMV) | 0 | — |
| MT4/tat-C (chr.1) | 97 | 35 |
| MT4/tat-C (chr.2) | 86 | 32 |
| AA2/WT (chr.) | 73 | n.d.[b] |
| Molt3/WT (chr.) | 80 | n.d. |

[a]"—," No survivors;
[b]n.d., not determined.

HIV-1 LTR/tat/nef Triple mMutants. Prolonged asymptomatic survival of macaques infected with a nef-deleted SIV strain SIVmac239 suggested that the nef gene is a pathogenesis factor (H. W. Kestler et al., Cell 65:651–662 [1991]). Evidence to strongly support this suggestion came from studies of a cohort of long term survivors infected with HIV-1 through blood transfusion from a single donor in Australia. All the survivors were found to carry HIV-1 strains with multiple deletions in nef and in the U3 region of the 3' LTR (N. J. Deacon et al., Science 270:988–991 [19951].

The LTR/tat-minus HIV-1 constructs were further modified by mutating the nef gene. To generate nef mutations, site specific mutagenesis was performed in the nef ORF to destroy its initiation codon, and a HindIII restriction site was generated (-AAGCTT-, nef-A mutant). Also, an additional stop codon was inserted in the nef ORF upstream of the polypurine tract (PPT) in the nef-A mutant, to generate a more defective nef-minus mutant (nef-B mutant, see below). The nucleotide sequence of pNL4-3 (HIV-1) from 9001 to 9031 (WT) was 5'-CTCAGGTACCTTTAAGACCAATGACTTACAA-3' (SEQ ID NO:2), while the nef-B mutant sequence generated by site-specific mutagenesis was 5'-CTCAGGTACCTTTAAGACTCTAGATCTAGAA-3' (SEQ ID NO:3). FIG. 13B provides a schematic showing a portion of the wild-type HIV-1 sequence, as well as the nef-B mutations (FIG. 13B; wild-type sequence provided in SEQ ID NOS:5 and 6). The nef-A mutations are also shown in this FIG. 13B. As indicated in this Figure, the nef-A and nef-B mutations contain the same mutations in the sequence shown starting at base 8781 (i.e., SEQ ID NO:5 corresponds the the nef-A sequence and nef-B sequence for this stretch of bases). The nef-A sequence is the same as the wild-type sequence for the sequence shown starting at base 9001 (ie., SEQ ID NO:6 represents the sequences for both wild-type and nef-A).

Figure 3:
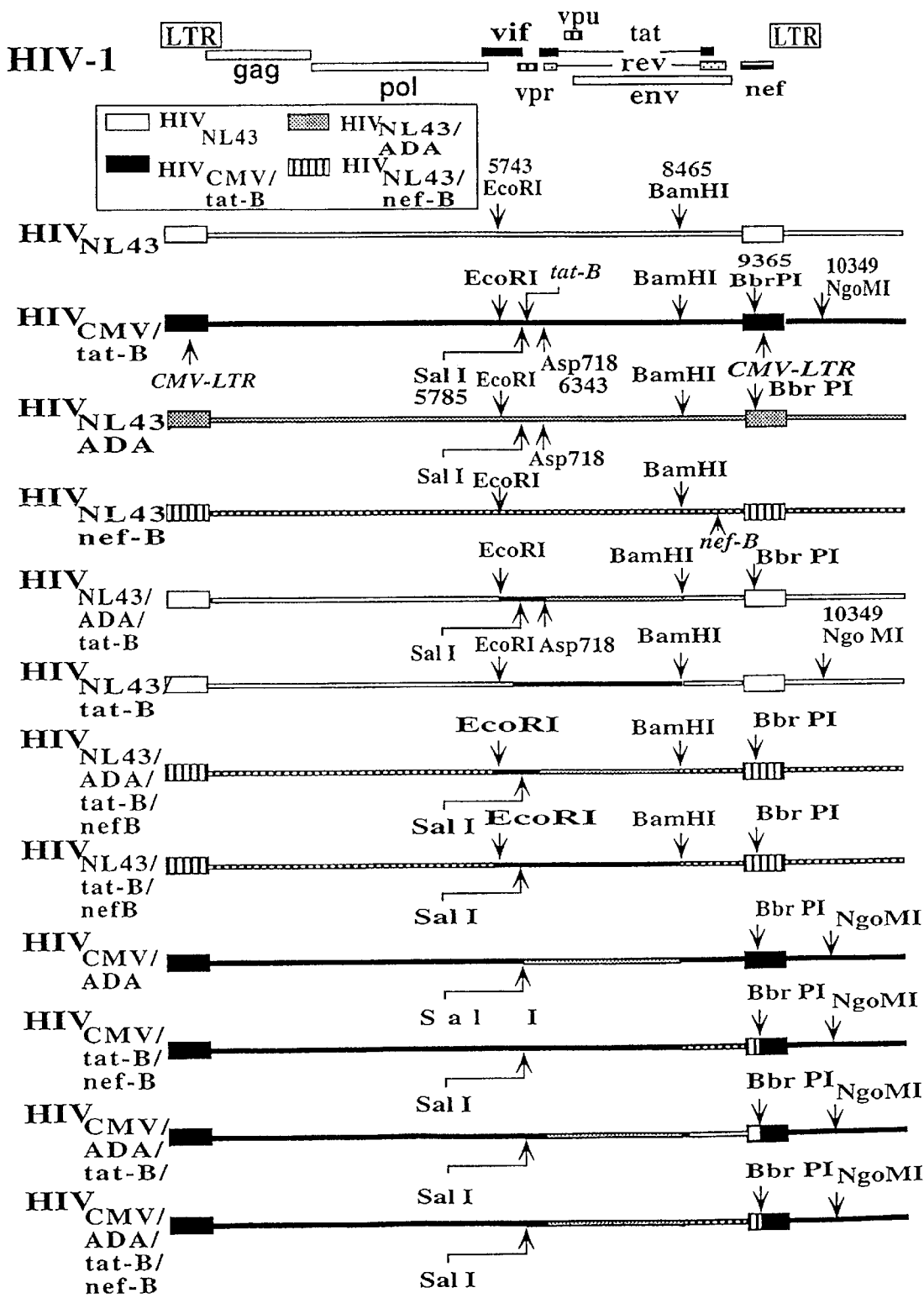
FIG. 3A shows the organization of the HIV-1 genome.
FIG. 3B shows a series of HIV-1 mutants containing LTR, tat, and nef mutations.

Since it is the non-syncytium-inducing, rather than the syncytium-inducing isolates of HIV-1 that are preferentially transmitted during primary infection, the T cell-tropic env gene of the LTR/tat/nef mutant was also substituted with a macrophage-tropic env (HIVADA). A schematic diagram of these HIV-1 mutants is shown in FIG. 3. These infectious molecular clones are further modified and attenuated by mutating other accessory genes including vpr, vif and vpu, as well as the U3 transcriptional regulatory elements NF-AT, NRT-1, USF and TCF-1a. A safe HIV-1 vector construct is developed from these attenuated HIV-1 LTR/tat/nef mutant constructs.

Additional packaging and transducing vectors derived from mutant HIV-1 LTR, tat and nef constructs established during the development of the present invention were generated and tested for vector function. Based on the results of experiments with the HIV-1 vectors, HIV-2 and SIV vectors were constructed using two molecular clones, HIV-2ROD and SIVmac. Continued experiments established an inducible packaging cell line using the tetracycline (TET-OFF) inducible system.

G. Replication-Competent HIV-1 Vectors Carrying Heterologous Foreign Genes

Earlier reports of HIV-1 vector systems demonstrated difficulties in generating high vector titers. This was likely due to multiple modifications in the viral genome during vector construction and the lack of a full understanding of the packaging mechanisms of HIV-1. In addition, vector titers are often construct-dependent. To analyze the ability of HIV-1 vectors carrying heterologous genes, several "replication-competent" HIV-1 vectors containing different foreign genes which were inserted in the nef open reading frame (ORF) in the 3' end of the viral genome were constructed.

The nef gene has been shown to play an important role in viral pathogenesis (Z. Du et al., Cell 82:665–674 [1995]; B. D. Jamieson et al., J. Virol., 68:3478–3485[1994]). Thus, it was considered to be more safe to delete the nef allele from the lentiviral vector system to produce useful vectors. Since the nef gene of HIV is dispensable for viral replication in tissue culture, and since the nef ORF does not overlap with other genes, a foreign gene can be inserted into the nef ORF without inactivating the virus.

Figure 4:
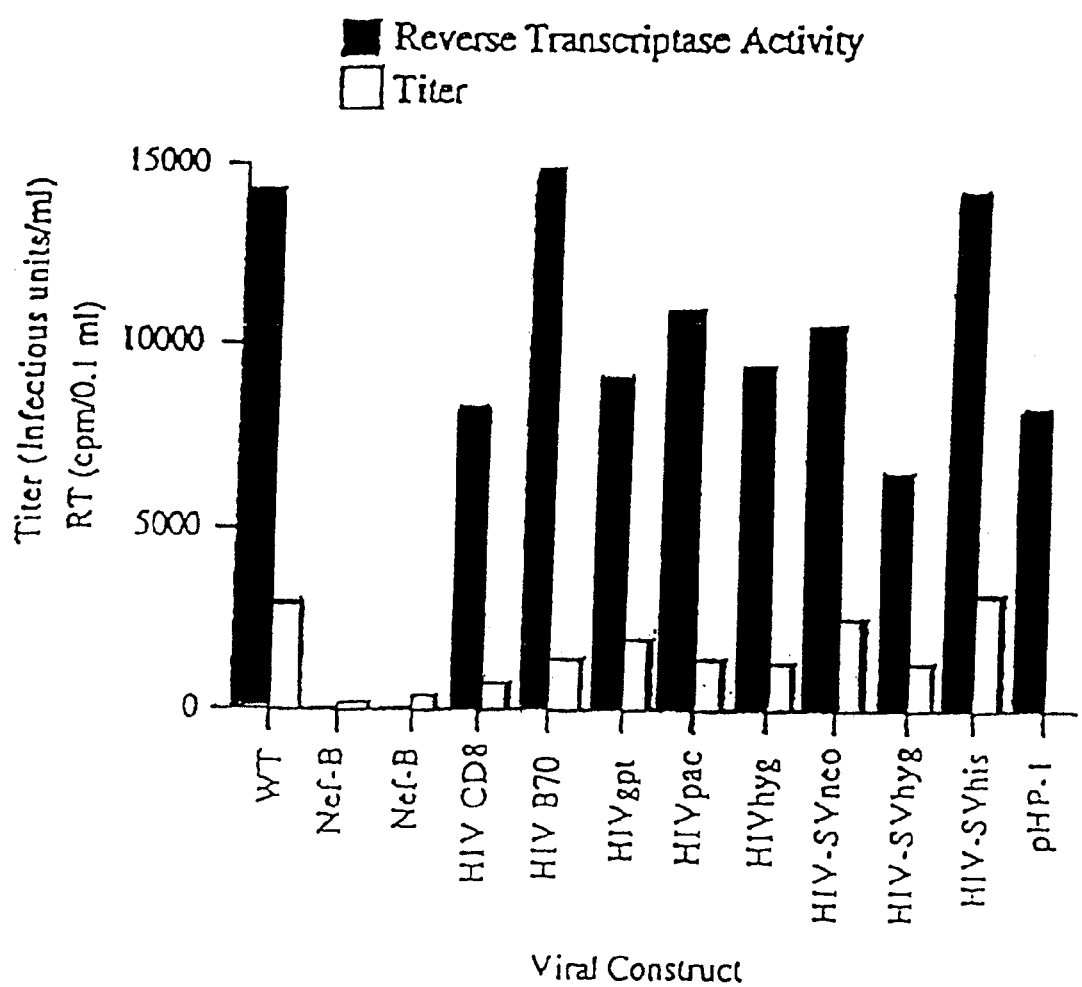
FIG. 4 shows replication efficiencies of several HIV-1 recombinants carrying heterologous genes.

FIG. 4 shows a comparison of the replication efficiencies of recombinant HIV-1 constructs carrying heterologous foreign genes. In these experiments, TE671 cells were transfected with plasmid DNA; 48 hours later, culture supernatants were used for the in vitro RT (reverse transcriptase) assay. Virus titer (i.e., transduction efficiency) was determined by infecting CD4 HeLa MAGI cells, and blue cell foci were counted under an inverted microscope after X-gal staining. The MAGI cells carry an integrated LTR-lacZ gene which can be transactivated by transduced HIV-1 Tat (J. Kimpton and M. Emernan, J Virol., 66:2232–2239.30 [1992]). The two scales in this Figure are numerically identical.

In addition, reporter genes including human T cell receptor CD8, T cell costimulator B7-2 (B70), the bacterial hygromycin-B-phosphotransferase (hyg), neomycin-phosphotransferase (neo), xanthine-guanine phosphoribosyltransferase (gpt), puromycin-resistant gene, and histidinol dehydrogenase (hisD) with or without an internal promoter (SV40) were inserted into the nef ORF at the new HindIII site or a downstream XhoI site in the nef-A mutant. These heterologous HIV-1 vector constructs were assessed by transfecting human TE671 cells, and quantitatively measuring viral RT expression and transduction efficiencies on a human CD4 cell line. Transduction efficiency was determined by counting the blue nucleated cell foci after X-gal staining. Two independent transfections were done. Representative results are shown in FIG. 4 (the standard deviation is not shown). An insertion of up to 1.5 kb of nucleotide sequences, such as B70 and SV-his, seemed to have no effect on RT production. Furthermore, the infectivity of HIV-SVhis is as high as wild-type HIV-1.

However, it was surprising to find that the nef-B mutation appeared to have an adverse effect on RT production (See, nef-B tested in duplicate, FIG. 4). The cause of this adverse effect is unclear (i.e., it may have been caused by interference with packaging or reverse transcription of the RNA genome), although an understanding of this mechanism is not required in order to use the present invention. Several vectors derived from the nef-B mutant construct showed the same deficiency and thus were reconstructed. A good correlation between RT activity and virus titer was observed in this study, except for pHP-1, which is a packaging vector construct lacking the HIV-1 packaging signals (see below).

These early experiments led to some embodiments of the methods of the present invention for manipulation of the HIV-1 genome for gene expression. For example, it appeared that HIV-1 can sustain extensive changes in the enhancer and promoter region but changes in the TATA box are less tolerable. Partial substitution of the intron region for the regulatory genes (tat and rev) in the env ORF with foreign sequences can affect the splicing efficiency of the singly-spliced messages, although the nearest splice acceptor site is almost 1 kb away (See e.g., B. A. Amendt et al., Mol. Cell. Biol., 14:3960–3970 [1994]). Sequences downstream of the gag AUG may also affect splicing efficiency from the major splice donor site 50 nt upstream of the gag AUG. These results suggested that: 1) a modified LTR with reduced homology to wild-type HIV-1 could be used in the vector design; and 2) deletion of the env sequence might interfere with expression of the tat and rev regulatory genes. In HIV-1 vector system, the env gene function may be deleted and replaced by the VSV-G envelope gene. As indicated herein, in some cases, it may be necessary to provide additional tat and rev functions for efficient Gag-Pol synthesis. Although an understanding of the mechanism(s) involved is not necessary in order to use the present invention, the study of heterologous replication competent HIV-1 constructs indicated that insertion of foreign sequences in the nef ORF is well tolerated and has minimal effects on viral replication. These advantages led to the development of various embodiments of the lentiviral vector systems of the present invention.

H. HIV-1 Packaging Constructs

Figure 5:
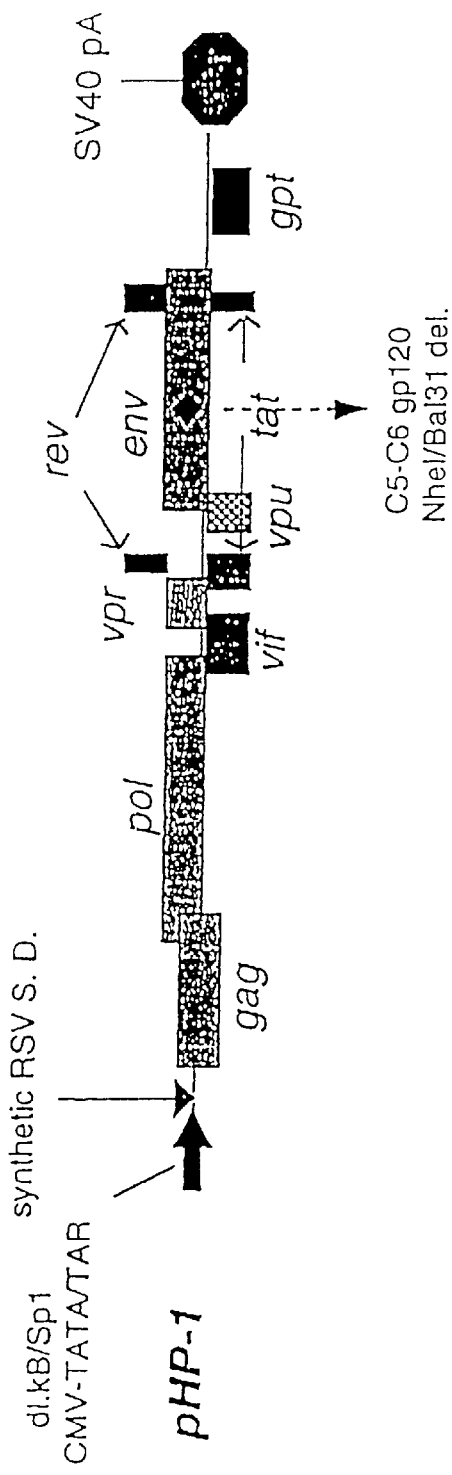
FIG. 5 shows an HIV-1 transducing vector diagram for the HIV packaging construct 1-del.env (pHP-1dl).

For the construction and testing of replication-defective lentiviral vectors, the attenuated HIV-1 constructs were modified. In one embodiment, the expression vector can synthesize all viral structural proteins but lacks the packaging signal function ("pHP"), includes a strong promoter (yet preferably not a native HIV-1 LTR), the gag-pol gene, the RRE element and the rev gene. The RRE-Rev interaction is critical to the synthesis of the Gag-Pol protein. Various approaches were explored in designing ideal vectors, including dissection of the wild-type genome, while carefully monitoring vector titers following each modification step; and starting with an over-simplified, inefficient vector construct and building back to restore wild-type function gradually. The goal was to achieve the best efficiency in vector production, yet have the vector remain replication-defective to minimize the chance of generating a replication-competent recombinant HIV-1 (RC-HIV). To this end, an expression construct (pHP-1) which contained a modified 5' HIV-1 LTR, a novel major splice donor site based on RSV splice sequences, the entire gag-pol-env, vif, vpr, vpu, tat, and rev genes, a selectable gpt marker gene, and an SV40 polyadenylation signal as shown in FIG. 5, was cloned.

pHP-1 lacks PBS, PPT, 3' LTR and most of the untranslated 5' leader sequences including the conventional retroviral packaging signal (ψ) and the major HIV-1 splice donor (SD) site. To further mutate pHP-1 for safety reasons (as discussed below), the env gene was deleted by Bal3 1 excision. To accomplish this, the unique NheI site was digested and treated with Bal31 to generate pHP-1dl2 and pHP-1dl28, DNA sequences. FIG. 5 is a schematic of the pHp-1-del.env (pHP-1dl.) packaging construct.

To determine whether a replication competent (RC) HIV recombinant could be generated, the transfected human TE671 cells were co-cultured with the human lymphoma cell line MT4. MT4 cells are an HTLV-1 transformed human CD4+ lymphoma cell line, which are very sensitive to HIV-1 infection. Uninfected MT4 cells were added into the co-culture every week during these experiments. To detect the recombinant HIV-1 RCR, a sensitive immunohistochemical staining method was used together with p24 ELISA and HIV RT assays. No infectious HIV-1 was detected after a two month coculture when either pHP1-dl2 (i.e., a two nucleotide deletion) or pHP-1dl28 (i.e., a 28 nucleotide deletion) was used (See, Table 4). However, infectious RC-HIV was detected when pHP-1 was used. Results of the Western blot analyses of the cell lysates showed that the level of viral proteins synthesized by pHP-1 was similar to that of the wild-type pNL4-3 (lanes 3 and 4, respectively, in FIG. 6). Analysis of reverse transcriptase (RT) activity in the transfected culture supernatants indicated that the level of active RT production was reduced 40% for pHP-1 compared with the wild-type construct. The expression of Gag-Pol function indicated that tat and rev were both functional. Thus, the artificially engineered splice donor (SD) site from Rous sarcoma virus (RSV) in the pHP-1 construct, a site that is unrelated to HIV sequences, was found to work like the wild-type SD site (i.e., allowing partition of spliced tat and rev, and unspliced gag-pol mRNAs into the cytoplasm). This is a critical factor in some embodiments of the present invention (i.e., the replacement of the HIV SD site with the RSV SD site), as the native leader sequences and the major splice donor site must both be deleted from the HP constructs to decrease the probability of homologous recombination with the transducing vectors (TV).

Five additional HP constructs were also made ("pHP-VSVG," lipHP-CMV," "pHP-EF," "pHP-CMVdel.TAR/SD," and "pHP-CMV-EF1α-intron"), each with additional changes (See, FIG. 7). pHP-VSVG was derived from pHP-1, with the HIV-1 env gene being replaced by the VSV-G gene and containing either wild-type (pHP-NVSV-G) or mutated (pHP-VSV-G) vpr and tat genes. pHP-CMV was derived from pHP-1, with the promoter being replaced by the cytomegalovirus immediate early promoter (CMV-IE) and the tat, rev, env, vpr and vpu genes deleted. pHP-CMVdel.TAR/SD was derived from pHP-CMV, with the TAR and RSV RD deleted. pHP-CMV-EF1α-intron was derived from pHP-CMVdel.TAR/SD, with an insertion of the EF1α-intron between the promoter and the Gag AUG. pHP-EF was derived from pHP-CMV, by replacing the CMV-IE promoter and the synthetic SD site with the human elongation factor 1α (EF1α) enhancer plus intron. The TAR sequence was also deleted. pHP-EF also contains an internal ribosomal entry site (IRES) and the vpr gene. The expression of Vpr may increase the vector transduction efficiency in nondividing culture. In other experiments, the intron-containing EF1α was shown to be a stronger promoter than the CMV-IE promoter.

Figure 6:
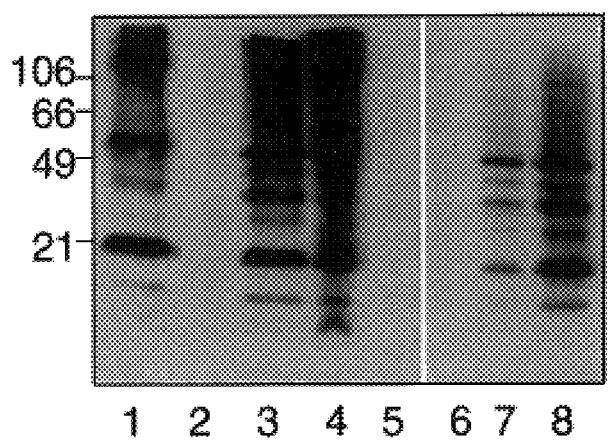
FIG. 6 shows a Western analysis of HIV-1 proteins in HeLa cells.

These constructs were tested as described in the Examples. pHP-VSVG did not express HIV-1 proteins unless the Tat transactivating protein was also present (i.e., compare lanes 6 and 7, in FIG. 6). These results indicated that although expression of VSV-G and Gag may be cytotoxic, an inducible packaging cell line can be established using pHP-VSVG without a tat plasmid. In addition, overexpression of Gag-Pol may not increase the vector titer because other experiments indicated that overexpression of Gag-Pol induces protease activation and prevents virus assembly and budding. The present invention provides vectors that produce measurable amounts of Gag-Pol (e.g., pHP-1, pHP-1del, and pHP-VSVG), as well as vectors that do not express detectable amounts of Gag-Pol (e.g., pHP-CMV and its derivatives).

I. HIV-1 Transducing Vector (TV) Constructs For the construction of a transducing vector, it was considered important to locate the packaging signals in the viral genome. The packaging signal in the 5' leader region (spanning the SD site and the gag AUG) of HIV-1 is not equivalent to the conventional ψ site of the MLV vectors, in that the latter alone allows efficient MLV vector packaging. Nevertheless, this region must be included in a retroviral vector because it overlaps with the dimer linkage sequence (DLS) which is also essential for genome packaging (See, J. L. Clever et al., J. Virol., 70:5902–5908[1996]; J. -C. Paillart et al., J. Virol., 70:8348–8354 [1996]; and J. -C. Paillart et al., Proc. Natl. Acad. Sci. USA. 93:5572–5577 [1996]). Several studies have shown that sequences in HIV-1, including LTR, TAR, RRE, and in the 5' gag ORF, are all necessary for efficient genome packaging, pointing to the complex nature of HIV-1 packaging signals (See e.g., A. Aldovini and R. A. Young, J. Virol., 64:1920–1926 [1990]; J. F. Kaye et al., J. Virol., 69:6593–6599 [1995]; A. Lever et al., J. Virol., 63:4085–4087[1989]; J. Richardson et al., J. Virol., 67:3997–4005 [1993]).

FIG. 8 provides a diagram of six HIV-1 transducing vectors, in which the vector backbone is derived from pNL4-3 and different LTRs. The IRES element shown in this Figure was derived from poliovirus, which could allow bicistronic gene expression.

To engineer a packaging signal for the construction of HIV-1 transducing vectors (TV), an artificial HIV-1ψ sequence using four synthetic oligonucleotides was synthesized, which comprised sequences between the PBS and the gag AUG (referred to as "ψ100") and sequences extending into the gag ORF (referred to as "ψ140"). These synthetic HIV-1ψ sequences contained a mutated SD site and a mutated gag AUG to avoid possible adverse effects in gene expression. The synthetic ψ signals were cloned into the pTVψ vector as shown in FIG. 8, which is comprised of two recombinant LTRs ("dl.kB-CMV/HIV-TAR"), the PBS and 5' leader sequences, an SV40-driven neo resistance gene, and the 3' PPT.

The packaging efficiencies of pTVψ100 and pTVψ140 (FIG. 8, constructs 1 and 2) were tested in a co-transfection experiment. HeLa cells were transfected with pHP-1 and pTVψ100 or pTVψ140 and 48 hours later, the culture supernatants were harvested and used to transduce CD4 HeLa cells (not VSV-G pseudotyped). G418 resistant colonies were counted 10 days later. As a control, HeLa cells were transfected with wild-type HIV-1 DNA; 48 hours later, the culture supernatant was used to infect CD4 HeLa cells. The titer of the wild-type HIV-1 was determined by a sensitive immunohistochemical staining method using anti-Gag p24 mAb as described by Chang and Zhang (L. -J. Chang and C. Zhang, Virol., 211:157–169 [1995]). Results of this study showed that both pTVψ100 and pTVψ140 were packaged at a very low efficiency (approximately 3 logs of magnitude less than the wild-type HIV-1).

This result indicated that additional HIV-1 sequences are needed to improve the packaging function of pTVψ100 and pTVψ140. Therefore, more HIV-1 sequences, including an additional gag sequence and an RRE element, were cloned into pTVψ140. One such example is shown in FIG. 9A (pTVψ+CMV-nlacZ-hyg). Again, the pTVψ+ was not packaged efficiently, indicating the splice donor site and Gag AUG mutations in pTVψ100 and pTVψ140 are detrimental to HIV packaging. While pTVψs cannot be used as efficient transducing vectors, pTVAs can be efficiently packaged and transduced, as shown below.

Thus, site-specific mutagenesis was performed to change 1–2 nucleotides in the splice donor site, and the Gag AUG in pTVAs using primers: 5'-GCGGCGACTGGGGAGGACGCCAA-3' (SEQ ID NO:7) and 5'-GAAGGAGAGAGTTGGGTGCGAG-3' (SEQ ID NO:8), to generate pTVΔSM vectors.

However, it is critical to avoid sequence homology between the packaging construct and the transducing vector construct so as to reduce the probability of recombination. Cotransfection with additional accessory genes such as vpr, nef and vpu may also help to increase the vector titer and the transduction efficiency. The homology between the modified pHP and pTV constructs are minimal. In order to generate a replication-competent HIV-1, the major SD site, the gag AUG and the env sequences must be restored, because they are deleted from the modified pHP and pTV constructs.

In an alternative approach for the construction of an efficient transducing vector the wild-type genome was gradually deleted (pTVΔ). In this embodiment, the two replication-competent HIV-1 vectors, "HIV-1-SVneo" and "HIV-1-SVhyg" (See, FIG. 4) were used as a starting point. These two constructs are nef-minus, and exhibited up to 50–70% of the wild-type HIV-1 replication efficiency. A deletion was made starting from the middle of the gag ORF to the middle of the env ORF. This did not delete the RRE element. The two deletion vectors, "pTVΔSVneo" and "pTVΔSVhyg," (See, FIG. 8, constructs 3 and 4) were examined for their transduction efficiencies in cotransfection experiments as described above.

In this experiment, VSV-G pseudotyped vectors were produced and the target cells were CD4-minus human cell lines. pHP-VSVG was co-transfected with a pTVA plasmid and a tat plasmid (pCEP4tat) into TE671 cells. Culture supernatant was harvested 48 hours later. Tat was included to transactivate both pHP-VSVG and pTVA. The production of virus was confirmed by RT assay, and expression of HIV-1 p24 and VSV-G was confirmed by immunohistochemical staining. Virus produced from the transfected cells were harvested without further concentration, and used to infect TE671 cells. After selection with either G418 or hygromycin for 7–10 days, cell colonies were counted under an inverted microscope. The VSV-G pseudotyped pTVΔSVneo and pTVΔSVhyg both produced transducing titers up to $10^3$/ml without further concentration. This titer was increased to $10^5$/ml without concentration, when pHP-dl.2 or pHP-dl.28 were co-transfected with pHEP-VSV-G. This result indicated that pHP-VSVG does not function efficiently.

Three additional pTVA vectors were also constructed, each containing a different reporter gene: CMV-GFP (green fluorescent protein, pTVΔCMV-GFP), CMV-nlacZ (pTVΔCMV-nlacZ) and CMV-nlacZ-hyg (pTVΔCMV-nlacZ-hyg), as illustrated in FIG. 8 (See, FIG. 8, constructs 5 and 6, as well as FIG. 9B). The production of VSV-G pseudotyped vector was tested with pTVΔCMV-nlacZ. TE671 cells transduced with the VSV-G pseudotyped pTVΔCMV-nlacZ vector stained strongly by X-gal and exhibited nuclear β-galactosidase activity. The pTVΔCMV-nlacz-hyg and pTVΔCMV-GFP did not express the reporter genes efficiently, whereas pTVΔCMV-nlacZ did. These transducing vectors were further characterized using dividing and nondividing tissue culture models and a small animal model.

J. Tissue Culture Assay for the Detection of Replication-Competent HIV-1 (RC-HIV)

Several sensitive assays are available for the detection of RCV in the present lentiviral vector systems. These include: (1) co-cultivation with a sensitive cell line such as MT4, AA2 or PBLs; (2) the CD4 HeLa MAGI cell assay which relies on Tat transactivation of an integrated LTR-lacZ gene; and (3) a sensitive immunohistochemical staining method for the detection of HIV antigen expression at the individual cell level. As described in the Examples below, the latter method was modified and developed for the characterization of "Tat-minus" HIV-1 infection, although all three methods are suitable for the routine titration of infectious HIV-1. Preliminary studies did not detect any replication-competent RCV from the above modified HIV-1 vector system, possibly due to the use of attenuated HIV-1 backbones and modified ψ signals with a mutated splice donor site and gag AUG used in the HIV-1 vectors described above. In addition, the env gene was deleted or replaced by the VSV-G gene in most of the pHP derivatives. However, the probability of generating an RC-HIV containing a recombined splice donor site, a restored gag AUG, and a novel endogenous human retroviral env gene was recognized as not being absolutely zero, necessitating rigorous examination in an artificial tissue culture recombination system.

K. Study of Cell-Mediated Immunity (CMI) using a Humanized SCID/beige Mouse Model Using a modified hu-PBL-SCID mouse reconstitution protocol, an in vivo model for evaluating CMI against HIV-1 in humans has been developed. SCID/beige mice lacking T, B and natural killer (NK) cell functions are severely immunodeficient. This strain of mice can be successfully reconstituted with fresh human peripheral blood lymphocytes (PBLs), and exhibits functional human naive, memory and activated T cell markers for more than 2–3 months (See e.g., copending U.S. patent application Ser. Nos. 08/848,760, and 08/838,702, both of which are herein incorporated by reference). In these experiments, spleen and peripheral blood lymphocytes were harvested 38 days after reconstitution from reconstituted SCID/beige mice, and red blood cells were lysed prior to incubation with anti-mouse 2Kd, anti-human CD45, anti-human CD3, anti-human CD4 and anti-human CD8 labeled antibodies. Reconstituted human lymphoid cell populations in the spleen and in the peripheral blood of the SCID/beige mice can reach up to 50–80% and 5–12%, respectively.

Finally, upon activation, the Th1 lineage of T cells produce interferon gamma (IFN-g) and the measurement of IFN-g production has been shown to be a reliable assay for CMI. Thus, to determine CMI against HIV-1 using the in vivo humanized SCID/beige mouse model, a sensitive ELISPOT assay for the detection of IFN-g producing cells was developed. With the computer assisted imaging system integrated into this protocol, the ELISPOT method was shown to be very convenient and more sensitive than the conventional limiting dilution assay for the determination of the effector T cell precursor frequency. This in vivo model and the ELISPOT assay system were developed for the evaluation of in vivo CMI after lentiviral gene transfer.

As some of the obstacles faced by the current gene therapy vectors lie in the poor expression level and the lack of long-term performance, it is contemplated that the vectors of the present invention be used in therapeutic gene therapy. Long-term gene transduction and high efficiencies of transduction of human cells by the HIV vectors of the present invention were compared with the conventional MLV vector (See, Table 5).

Experimental

The following examples serve to illustrate certain preferred embodiments and aspects of the present invention and are not to be construed as limiting the scope thereof.

In the experimental disclosure which follows, the following abbreviations apply: RCR (replication-competent retrovirus); RCV (replication-competent virus); WT (wild-type); PBL (peripheral blood lymphocyte); M (molar); mM (millimolar); µM (micromolar); mol (moles); mmol (millimoles); µmol (micromoles); nmol (nanomoles); g (gravity); gm (grams); mg (milligrams); µg (micrograms); pg (picograms); L (liters); ml (milliliters); µl (microliters); cm (centimeters); mm (millimeters); µm (micrometers); nm (nanometers); hr (hour); min (minute); msec (millisecond); ° C. (degrees Centigrade); AMP (adenosine 5'-monophosphate); cDNA (copy or complimentary DNA); DTT (dithiothreitol); ddH$_2$O (double distilled water); dNTP (deoxyribonucleotide triphosphate); rNTP (ribonucleotide triphosphate); ddNTP (dideoxyribonucleotide triphosphate); bp (base pair); kb (kilo base pair); TEM (transmission electron microscope); SEM (scanning electron microscope); TLC (thin layer chromatography); tRNA (transfer RNA); nt (nucleotide); VRC (vanadyl ribonucleoside complex); RNase (ribonuclease); DNase (deoxyribonuclease); poly A (polyriboadenylic acid); PBS (phosphate buffered saline); OD (optical density); HEPES (N-[2-Hydroxyethyl] piperazine-N-[2-ethanesulfonic acid]); HBS (HEPES buffered saline); SDS (sodium dodecyl sulfate); Tris-HCl (tris [Hydroxymethyl]aminomethane-hydrochloride); rpm (revolutions per minute); ligation buffer (50 mM Tris-HCl, 10 mM MgCl$_2$, 10 mM dithiothreitol, 25 µg/ml bovine serum albumin, and 26 µM NAD+, and pH 7.8); EGTA (ethylene glycol-bis(P-aminoethyl ether) N, N, N', N'-tetraacetic acid); EDTA (ethylenediaminetetracetic acid); ELISA (enzyme linked immunosorbant assay); LB (Luria-Bertani broth: 10 g tryptone, 5 g yeast extract, and 10 g NaCl per liter, pH adjusted to 7.5 with 1N NaOH); superbroth (12 g tryptone, 24 g yeast extract, 5 g glycerol, 3.8 g KH$_2$PO$_4$ and 12.5 g, K$_2$HPO$_4$ per liter); DMEM (Dulbecco's modified Eagle's medium); ABI (Applied Biosystems Inc., Foster City, Calif.); Amersham (Amersham Corporation, Arlington Heights, Ill.); ATCC (American Type Culture Collection, Rockville, MY); AIDS Research and Reference Reagent Program (AIDS Research and Reference Reagent Program of the National Institutes of Health, Bethesda, Md.); Beckman (Beckman Instruments Inc., Fullerton Calif.); BM (Boehringer Mannheim Biochemicals, Indianapolis, Ind.); Bio-101 (Bio-101, Vista, Calif.); BioRad (BioRad, Richmond, Calif.); Brinkmann (Brinkmann Instruments Inc. Wesbury, NY); BRL, Gibco BRL and Life Technologies (Bethesda Research Laboratories, Life Technologies Inc., Gaithersburg, Md.); CRI (Collaborative Research Inc. Bedford, Mass.); Eastman Kodak (Eastman Kodak Co., Rochester, N.Y.); Eppendorf (Eppendorf, Eppendorf North America, Inc., Madison, Wis.); Falcon (Becton Dickenson Labware, Lincoln Park, N.J.); IBI (International Biotechnologies, Inc., New Haven, Conn.); ICN (ICN Biomedicals, Inc., Costa Mesa, Calif.); Invitrogen (Invitrogen, San Diego, Calif.); New Brunswick (New Brunswick Scientific Co. Inc., Edison, N.J.); NEB (New England BioLabs Inc., Beverly, Mass.); NEN (Du Pont NEN Products, Boston, Mass.); Nichols Institute Diagnostics (Nichols Institute Diagnostics, San Juan Capistrano, Calif.); Pharmacia (Pharmacia LKB Gaithersburg, Md.); Promega (Promega Corporation, Madison, Wis.); Stratagene (Stratagene Cloning Systems, La Jolla, Calif.); UVP (UVP, Inc., San Gabreil, Calif.); USB (United States Biochemical Corp., Cleveland, Ohio.); Taconic (Taconic, Germantown, N.Y.); and Whatman (Whatman Lab. Products Inc, Clifton, N.J.).

Unless otherwise indicated, all restriction enzymes were obtained from New England Biolabs and used according to the manufacturers directions. Unless otherwise indicated, synthetic oligonucleotides were synthesized using an ABI DNA synthesizer, Model No. 391.

In the following Examples, non-attenuated HIV strains used include the NL4-3 strain, and HIV-1 primary isolates covering the different HIV clades (e.g., 92RW008, 92HT593, etc., are available from the AIDS Research and Reference Reagent Program.

EXAMPLE 1

Construction of HIV-1 Packaging and Transducing Vectors In this Example, HIV-1 packaging and transducing vectors were constructed. Two packaging plasmids, "pHP-1" and "pHP-VSVG," containing HIV-1 env and VSV-G envelope gene respectively, were constructed. FIG. 7 is a structural diagram of seven different pHP vector constructs, including pHP-1 and pHP-VSVG.

In this Example, attenuated HIV-1 constructs were modified to produce the "pHP-1" expression vector capable of synthesizing all viral structural proteins, but lacking the packaging signal function. This vector included a strong promoter (in preferred embodiments, it is preferably not a native HIV-1 LTR), the gag-pol gene, the RRE element, the tat, and the rev gene. The RRE-Rev interaction is critical to the synthesis of the Gag-Pol protein.

Two approaches to designing the vectors were considered, namely 1) dissecting down the wild-type genome while carefully monitoring vector titers following each modification step, and 2) starting with an over-simplified, inefficient vector construct and building back to restore wild-type function gradually. The goal was to achieve the best efficiency of vector production yet have the vector remain replication-defective to minimize the chance of generating a replication-competent recombinant HIV-1 (RC-HIV). To achieve this, the expression construct pHP-1, which contained a modified 5' HIV-1 LTR, a novel major splice donor site derived from RSV, the entire gag-pol-env,vif, vpr, vpu, tat, and rev genes, a selectable gpt marker gene, and an SV40 polyadenylation signal as shown in FIG. 5 was developed.

pHP-1 lacks the native HIV-1 TATA box, the primer binding site (PBS), polypurine tract (PPT), 3' LTR and most of the untranslated 5' leader sequences including the conventional retroviral packaging signal (Ψ) and the major HIV-1 splice donor (SD) site. pHP-1 contains all HIV structural and accessory genes except for the nef gene and thus is capable of expressing the vast majority of the viral proteins, and also contains the bacterial gpt gene. pHP-1 provides a provirus capable of mimicking HIV-1 infection in terms of the viral proteins expressed yet this virus cannot be packaged into viral particles. Further mutations introduced into the pHP-1 provirus, including deletion in the env and in the 5' LTR, vpr, vif and vpu, greatly reduce the possibility that wild-type HIV will be produced by recombination. Thus, pHP-1 provides an excellent HIV DNA vector. pHP-1 was constructed as follows. First, the Tat-responsive enhancer promoter CMV-TATA-TAR fragment (approximately 400 bp) was isolated from dl.kB/Sp1-CMV-TATA-TAR HIV (Chang et al., J. Virol. 67:743 [1993]) by BbrpI-HindIII digestion, and cloned into EcoRV-BamHI digested pSP72 (Promega) via a linker providing HindIII and BamHI cohesive sites which contains a modified gag AUG with Kozak translation initiation context and a major splice donor site of Rous sarcoma virus. This linker was formed by annealing the following oligonucleotides: 5'-AGCTTGGTCGCCCGGTGGATCAAGACCGGTAGC CGTCATAAAGGTGAT TTCGTCG-3' (SEQ ID NO:9) and 5'-GATCCGACGAAATCACCTTTATGACG GCTACCGGTCTTGATCCACCGGGCGACCA-3' (SEQ ID NO:10). This first subclone was called pSP-CMV-TAR-SD.

Secondly, the gag coding sequence was obtained by PCR from pNL4-3 (a full-length HIV-1 plasmid) using a 5' primer (5'-CGGGATCCACCATGGGTGCGAGAG CGTC-3' [SEQ ID NO:11]) and a 3' primer downstream of the SphI site in the gag gene (5'-ATCCTATTTGTTCCTGAAGG-3' [SEQ ID NO:12]). The PCR product was digested with BamHI-SphI (~660 bp) and this fragment was ligated with BamHI-SphI digested pSP-CMV-TAR-SD to obtain pSP-CMV-TAR-SD-dl.gag.

Next, the poly-A minus subclone pHP-dl.pA was constructed by ligating the following three fragments: a 1112 bp HpaI-SphI fragment isolated from pSP-CMV-TAR-SD-dl-.gag (contains the promoter-TAR-SD-dl.gag), a 7922 bp SphI-XhoI fragment (dl.gag-pol-env-gpt) of pNLgpt, and a plasmid vector backbone provided by EcoRV-XhoI digested pBS-KS(–) (Stratagene).

Lastly, pHP-1 was made by the following ligation: NotI-XhoI (9059 bp) of pHP-dl.pA containing dl.CMV-TATA-TAR-SD-gag-pol-env-gpt, a 422 bp poly-A site from XhoI-PstI digested pREP9 (Invitrogen), and NotI-PstI digested pBS-KS(–). The sequence of pHP-1 (12,494 kb) is provided in SEQ ID NO:13; this sequence begins at the promoter of the half-BbrPI site from pNL4-3 (an HIV clone available from the AIDS Research and Reference Reagent Program; the sequence of this recombinant clone is shown in Genbank Accession No. M19921). Additional mutations of pHP-1 to generate pHP-1dl2 and pHP1-dl.28 are described above (See also, FIG. 5).

To determine whether a replication-competent HIV (RC-HIV) recombinant could be generated, human TE671 cells (ATCC CRL 8805) were transfected with pHP-1 DNA plus the transducing vector pTVΔnlacZ or pTV.ψ.nlacZ (FIGS. 8 and 9), and the transfected cells were cocultured with the human lymphoma cell line MT4. MT4 cells (AIDS Research and Reference Reagent Program) are an HTLV-1 transformed human CD4+ lymphoma cell line, which are very sensitive to HIV-1 infection as described in Example 8. Infectious HIV-1 was detected in the pHP-pTV coculture indicating the generation of RC-HIV in cells containing pHP-pTV (See, Table 4). On the other hand, no pTV RC-HIV was detected with a very sensitive co-culture and immunostaining assay, even after 60 days of culture, when pHP-1.dl.28 or pHP-1.dl2 were used with pTVdl plasmids in the co-transfection experiments (See, Table 4). To detect the synthesis of HIV-1 proteins, cell lysates were prepared and analyzed by Western blotting in comparison with a wild-type HIV-1 construct, pNL4-3, as described in Example 2. The results showed that the level of viral proteins synthesized by pHP-1 was similar to that of the wild-type pNL4-3 (See, FIG. 6). Similar results were obtained when pHP.l.dl constructs were used.

Analysis of reverse transcriptase (RT) activity in the transfected culture supernatants indicated that the level of active RT production was reduced 40% for pHP-1 compared with the wild-type construct pNL4-3. The expression of Gag-Pol function indicates that tat and rev are functional. Thus, the artificially engineered splice donor (SD) site in the pHP-1 construct, which is unrelated to HIV sequences, works like the wild-type SD site (i.e., allowing partition of spliced and unspliced mRNAs into the cytoplasm).

As described in more detail below, five other HP constructs were made, pHP-VSVG, three pHP-CMV derivatives, and pHP-EF, each with additional changes (See, FIG. 7). pHP-VSVG was derived from pHP-1, with the HIV-1 env gene being replaced by the VSV-G gene, and with wild-type vpr and tat, or the vpr and tat genes mutated by site-specific mutagenesis. pHP-CMV was derived from pHP-1 with the promoter being replaced by the cytomegalovirus immediate early promoter (CMV-IE) and the tat, rev, env, vpr and vpu deleted. pHP-CMVdel.TAR/SD was derived from pHP-CMV, with the TAR and RSV RD deleted. pHP-CMV-EF1α-intron was derived from pHP-CMVdel.TAR/SD, with an insertion of the EF1α-intron between the promoter and the Gag AUG. pHP-EF was derived from pHP-CMV by replacing the CMV-IE promoter and the synthetic SD site with the human elongation factor 1α (EF1α) enhancer plus intron. It also contains an internal ribosomal entry site (IRES) and the vpr gene. The expression of Vpr may increase the vector transduction efficiency in non-dividing cultures. The intron-containing EF1a has been shown to be a stronger promoter than the CMV-IE promoter. These constructs were tested for their expression of HIV-1 proteins. pHP-VSVG did not express HIV-1 proteins unless the Tat transactivating protein is also present (See, FIG. 6, lane 6 vs. 7). Thus, although expression of VSV-G and Gag may be cytotoxic, an inducible packaging cell line could be established using pHP-VSVG without a tat plasmid. It should also be noted that overexpression of Gag-Pol may not increase the vector titer because earlier studies have shown that overexpression of Gag-Pol induces protease activation and prevents virus assembly and budding (V. Karacostas et al., Virol., 193:661–671 [1993]; J. Park and C. D. Morrow, J. Virol., 65:5111–5117 [1991]).

Both packaging constructs (i.e., pHP-1 and pHP-VSVG) used a recombinant CMV/HIV-LTR as promoter and a synthetic major splice donor site. No sequence homology was observed with the HIV-1 genome between TAR (in the 5' end of the RNA) and the gag AUG in these two constructs. A BamHI site was generated near the gag AUG for the purpose of inserting recombinant HIV-2 and SIV gag-pol sequences in subsequent experiments.

The pHP-VSVG construct with vpr and tat mutations lacks vpr and tat genes, and the VSV-G gene is substituted for the env gene exactly at the env AUG by PCR mutagenesis. These two constructs were the first two packaging plasmids tested. Analyses of RNA expression and packaging function were subsequently performed in order to compare these vectors directly with the wild-type HIV-1.

These experiments showed that pHP-CMV and pHP-EF do not express Gag-Pol protiens at high efficiencies, indicating that the pHP-1-derived vectors have important viral sequences that are necessary for efficient vector production.

pHP-VSVG.

This clone was made to delete the HIV-1 env gene and replace it with the VSV-G gene, as well as delete the HIV-1 vpr and tat genes. It was constructed by combining the following four pieces of DNA fragments: 1) the recombinant LTR (dl.kB/Sp1-CMV-TATA-HIV-TAR) gag-pol from NotI to EcoRI fragment of pHP-1; 2) a fragment from HIV-1 with deletion in the C-terminal of Vpr and the N-terminal of Tat by PCR using the following two primers 5'-TAA GAA TTC TAG TAG GTT GCT TTC ATT GCC-3' (SEQ ID NO:14), and 3'-CTT CTC CTT CAC TCT CGA GTG ATC ACT GTC TTC TGC TCT TTC-3' (SEQ ID NO:15), with the second sequence encompassing the env AUG with a new XhoI and a BclI site); 3) the VSV-G gene fragment cut by SalI-XbaI from pBS-VSV-G (obtained from Tom Hobman of the University of Alberta); and 4) a deleted env-gpt-SVpA and plasmid vector backbone from NheI-NotI digested pHP-1.

pHP-CMV.

This clone was derived from pHP-1, with the 5' recombinant LTR replaced by a CMV-IE enhancer-promoter and the entire env, tat, vpu, rev, vpr, nef deleted, but with the vif gene remaining intact. This clone was constructed by ligation of the following 3 pieces of DNA: 1) the vector pcDNA3.1Zeo(+) from Invitrogen cut with NheI-XhoI; 2) the TAR/SD-gag-pol from pHP-1 digested with XbaI-EcoRI; and 3) the RRE element from pBS-RRE digested with EcoRI-XhoI. pBS-RRE was constructed by ligating BglII (nt. 7611) to HindIII (nt. 8131) of pNL4-3 of HIV-1 with BglII-HindIII digested pBS-EF. pBS-EF was from the PCRed EF1a enhancer promoter cloned into pBS(−).

pHP-CMV-del.TAR/SD:

This clone is the same as pHP-CMV except that the 5' TAR and splice donor site are deleted. This construction was made by ligating the following two fragments: 1) a 702 bp fragment of MluI-BamHI digested pcDNA3.1Zeo(+) containing the CMV enhancer; and 2) the vector containing MluI-BamHI digested pHP-CMV which has deleted TAR and contains the RSV splice donor site.

pHP-CMV-EF1α-intron.

This clone is similar to pHP-CMV-del.TAR/SD but with an intron from human EF-1a gene inserted between the CMV promoter and the gag AUG. It was made by ligating the following three DNA fragments: 1) pHP-1 BamHI-EcoRI fragment containing gag-pol and vif; 2) the MluI-EcoRI of pcDNAZeonlacZ-RRE containing the vector backbone of pcDNA3.1Zeo(+), HIV-1 RRE and part of the CMV promoter; and 3) the rest of the CMV enhancer promoter was obtained from BamHI-MluI digested pcDNAZeoHGHP2EF, a pcDNAZeo3.1(+) vector containing EF1α intron and the human growth hormone gene. The hGH cloned sequence is available from GenBank. See co-pending U.S. patent application Ser. No. 08/848,760 (incorporated by reference) for additional information regarding this construct.

EXAMPLE 2

Western Blotting of HIV-1 Proteins in HeLa Cells

In this Example, Western analyses of HIV-1 proteins in HeLa cells transfected with various vector constructs were tested. In this Example, cell lysates were prepared and analyzed by Western blotting and compared with a wild-type HIV-1 construct (pNL4-3), in order to determine the level of viral proteins synthesized by pHP-1 and pHP-VSVG (with and without Tat), in comparison with wild-type HIV-1. In this Example, the Western blots were performed using serum obtained from an HIV-infected individual, and methods known in the art (See e.g., Ausubel et al. (eds.) *Short Protocols in Molecular Biology*, 2d ed., John Wiley & Sons, New York, N.Y. [1992], pp. 10.33–10.35).

FIG. 6 shows the results of the Western analyses. In this Figure, lane 1 contains cell lysate from MT4 cells infected with HIV-1; lane 2 contains control HeLa cell lysate; lane 3 contains lysate from HeLa cells with pHP-1; lane 4 contains wild-type HIV-1 pNL4-3 cell lysates; lanes 5 and 6 contain pHP-VSVG-transfected cell lysates; lane 7 contains pHP-VSVG+Tat cell lysate; and lane 8 contains pHP-VSVG+Vpr cell lysate. As indicated in FIG. 3, the results showed that the level of viral proteins synthesized by pHP-1 was similar to that of the wild-type pNL4-3 (See, lanes 3 and 4, respectively, in FIG. 6).

These results indicated that in the absence of Tat, the recombinant LTR of pHP-VSVG is inactive. Thus, it is likely that the TAR element in the LTR down-regulates transcriptional elongation. These results led to the generation of an inducible packaging cell line using the pHP-VSVG construct as described in Example 3.

EXAMPLE 3

Generation of an Inducible Packaging Cell Line

In this Example, an inducible packaging cell line was generated using the pHP-VSVG, and its derivative construct. First, pHP-VSVG was linearized and transfected into human TE671 cells by electroporation, together with a selective marker. After selection, individual cell clones were tested for Gag-Pol expression by direct extracellular RT assay in the presence or absence of a transfected tat plasmid. The expression of VSV-G protein was detected by immunohistochemical staining.

Briefly, the pHP-VSVG linearized by digestion with NotI, and transfected into the TE671 cells along with pSV2-neo (i.e., with G-418 as the selectable marker). Transfection was accomplished by electroporation, using methods known in the art. Transfected cells were grown in 1 mg/ml of G418 culture in DMEM containing 10% FBS. The induced gag-pol Gag-Pol expression was then determined by direct extracellular RT assays with and without transfected tat plasmid. HIV-1 Gag and RT expression were detected by p24 antigen ELISA or RT (See, co-pending U.S. patent application Ser. Nos. 08/791,994 and 08/838,702; See also, L. J. Chang and C. Zhang, Virol., 211:157–169 [1995]; and L. J. Chang et al., J Virol., 67:743–752 [1993]).

The expression of Gag-Pol in this inducible cell line still requires Tat function. To make a user-friendly packaging cell line, vpr and tat genes can also be expressed by an inducible promoter. The vpr gene is included because of its function in promoting transduction of nondividing cells. A tetracycline-inducible expression vector (a TET-OFF system, suppression of expression in the presence of tetracycline or doxycycline) has been chosen for this purpose. An inducible tat-vpr expression vector has been constructed into the pcDNA3.1/Zeo plasmid with genes arranged in the following order: -tetOP-tat-IRES-vpr-IRES-tetR.VP 16-SVpA-(inverted tk-zeo-pA). Preliminary studies of this construct showed co-expression of Tat and Vpr in the absence of tetracycline or doxycycline, indicating that the two internal ribosomal entry site (IRES) are functional. However, even in the presence of tetracycline or doxycycline, this inducible construct still expresses Tat function, indicating a leaky expression of the tetR.VP16. As a result, this construct was only used for coexpression of Tat and Vpr in the co-transfection experiments.

A second construct, -tetOP-tat-P2-vpr-SVpA-(inverted tk-zeo-pA), which is up-regulated by a separate tetR.VP16 expression plasmid, has been constructed and used to generate an inducible cell line.

tetOP-tat-P2-vpr-P2-tetR-VP16-SVpA-(inverted tk-zeo-pA) is a clone that expresses HIV-1 Tat and Vpr and the tet tTA operon inducer tetR-VP16 which was made by ligation of the following fragments: tetOP, HIV-1 Tat, internal ribosomal entry site (IRES) P2, HIV-1 Vpr, IRES P2, tetR-VP16, and the vector pREP9 with EBNA1 gene sequence deleted. The two tTA plasmids were obtainable from Display Systems Biotechnology, Inc. (now distributed by Clontech). This clone is auto-inducible by the removal of tetracycline or doxycycline (2–10 microgram/ml) from the culture media (a Tet-OFF system)(See, M. Gossen and H. Bujard, Proc. Natl. Acad. Sci. USA. 89:5547–5551 [1992]).

As these plasmids use different selective markers (neo, zeo, and hyg) it was possible to co-select them in the same cell. However, a large number of cell clones had to be screened before a stable inducible packaging cell line could be established.

EXAMPLE 4

Additional Packaging Vectors

Four additional packaging vectors, pHP-CMV derivatives, and pHP-EF, were constructed as shown in FIG. 7. The heterologous enhancer/promoters in these vectors may express high levels of viral structural proteins and exhibit improved vector titers. Expression of extracellular RT and particles were analyzed by in vitro RT assay and Western analysis after the particles are concentrated on a sucrose gradient. In parallel to the construction of packaging vectors, several transducing vectors have also been made (See, FIG. 8). These constructs express selective markers such as neo and hyg and/or reporter genes GFP or nlacZ. A few modifications such as the insertion of RRE sequence and restoring the native 3' LTR have been included to increase the packaging efficiency of these vectors. These different constructs were examined in transient transfection experiments. By transfection, the vector titer was directly compared to wild-type HIV-1 which can be titrated on CD4 HeLa cells (FIG. 4). As different reporter genes or therapeutic genes have different effects on vector packaging and stability, further modifications are contemplated, as needed. For example, it was noticed that the expression level of GFP is much improved when an intron sequence was inserted in front of the GFP gene. All of the pHP-CMV derivatives were tested, and found to be inefficient in synthesizing HIV proteins, indicating that the pHP-1 and pHP-VSVG derivatives are the preferred embodiments of the efficient HIV vector system of the present invention.

EXAMPLE 5

Construction of HIV-2 and SIV Vectors

Based upon the experiments conducted during development of the HIV-1 vector system, HIV-2 and SIV vector systems are developed (pH2P and pSIVP). To establish a lentiviral vector based on HIV-2 or SIV, the 5' LTR and the untranslated leader sequences of HIV-2ROD and SIV-mac239 are replaced with the recombinant HP-1 enhancer/promoter and a synthetic leader sequence with or without a splice donor site, both obtainable from the pHP vectors. The 3' LTR is replaced by the SV40 polyadenylation signal. The nef and env genes are both deleted from the vector. The expression of vpx is included in the HIV-2/SIV packaging cells because it has been shown that the HIV-2/SIV vpx (or SIVagm vpr) is necessary and sufficient for nuclear import function and does not inhibit cell cycle progression as does vpr. The VSV-G envelope gene is expressed from a separate expression vector.

Previous studies suggested that SIV or HIV-2 genomes can be assembled into the HIV-1 particles, indicating that the packaging signals of SIV or HIV-2 can be recognized by HIV-1 nucleocapsids. To construct a lentiviral 'transducing vector' based on HIV-2 or SIV, a construct similar to the pTVA vector is made which contains the SIV or HIV-2 packaging signals (from 3' of the PBS to the extended gag sequences). These HIV-2 and SIV transducing vectors (pTV2 and pTVS) are first tested in co-transfection experiments using pH2P or pSIVP. The transduction efficiency is compared to the HIV-1 vector constructs carrying the reporter gene lacZ.

The transducing vectors of HIV-2 (pTV2) and SIV (PTVS) using their native genome sequences are constructed in a manner similar to that of the HIV-1 pTV vectors. However, instead of using modified LTRs, a strong heterologous promoter is used and the transcription initiation site is placed at the beginning of the R-U5 sequence. Sequences in gag-pol and env genes are deleted and the major SD and the gag AUG are mutated. A CMV-driven reporter gene cassette such as the CMV-IE-nlacZ-IRES-hyg from the pTVA-nlacZ-hyg vector is inserted in the nef ORF of the HIV-2 and the SIV vectors. The 3' LTR resembles the native LTR but with a deletion in the NF-kB and the Sp1 binding sites.

The transduction efficiencies of VSV-G-pseudotyped HIV-2 or SIV vectors is then determined by cotransfection of TE671 or Cos7 cells with packaging vectors plus VSV-G and additional accessory genes as described below. The pseudotyped HIV-2 and SIV vectors are titrated on human TE671 cells, to provide data for further modifications of the vectors.

EXAMPLE 6

Internal CMV-IE in pTVΔCMVnlacZ Promoter Exhibits Higher Promoter Activity Than Native CMV-IE In this Example, the expression of the reporter lacZ gene from the pTV-ΔCMVnlacZ was compared with pcDNAn-lacZ (i.e., CMV-IE promoter-driven), 48 hours after transfection of TE671 cells. TE671 cells were transfected with 5 μg of pcDNA3-nlacZ or pTVΔCMVnlacZ, as described above. Following transfection and growth, cells were fixed and stained for β-galactosidase actvity, as described below.

The beta-galactosidase activity was detected by the following protocol as published by Kimpton and Emerman (J. Kimpton and M. Emerman, J Virol., 66:2232–2239 [1992]). Briefly, cells were fixed in culture plate at room temperature, with 1% formaldehyde (1.33 ml of 37.6% for final 50 ml) and –0.2% glutaraldehyde (0.4 ml of 25% for final 50 ml) in PBS for 5 minutes. The cells were then washed three times with PBS, and incubated with 500 μl ddH$_2$O containing 4 mM potassium ferrocyanide (100 μl of 0.4 M for final 10 ml), 4 mM potassium ferricyanide (100 μl of 0.4 M), 2 mM MgCl$_2$ (20 μl of 1 M), 0.4 mg/ml X-Gal (200 μl of 20mg/ml) at 37° C. for 50 minutes to several hours. The blue-staining (i.e., β-galactosidase positive) cells were counted under an inverted microscope. These results indicated greater expression by the pTVΔCMVnlacZ vector, as compared with the pcDNA3-nlacZ. Table 2 shows the results, with more " indicating the presence of a relatively greater number of blue-staining cells.

TABLE 2

| Plasmid | β-Galactosidase Activity Cells Stained (Blue) |
|---|---|
| Mock | − |
| pcDNAnlacZ | ++ |
| pTVΔCMVnlacZ | +++ |

EXAMPLE 7

Production and Concentration of VSV-G Pseudotyped Vectors In this Example, TE671 cells were transfected with pHP-1, pTV and pHEF-VSV-G. Various pTV vectors were tested in early experiments to identify which worked. It was found that while some of the pTVΔ vectors, none of the pTVψ or other pTVA vectors worked as transducing vectors.

First, pTVΔSVneo was created by digesting pNL-SV with NheI (with a site located in the middle of the env gene), and SpeI (with a site in the middle of the gag gene), and then self-ligated to delete the gag-pol-env, and vif vpu, vpr, tat, and rev genes. pNLSV was created by inserting SVneo in between the nef AUG and the XhoI site in the N-terminus of nef. pTVΔCMVnlacZ was made by digesting pTVΔSVneo with XhoI-KpnI as the vector, which deleted SVneo and part of the nef sequences near the 5' end of the PPT of HIV-1, the product was then ligated with a SalI-KpnI fragment containing CMV-nlacZ sequence from pcDNAzeo-nlacZ. pcDNAzeo-nlacZ was generated by inserting nlacZ of pSP72nlacZ into pcDNA3.1zeo(+).

Culture supernatants were harvested 24 hours after removal of transfection solution. HIV RT activity was detected by an in vitro RT assay and vector titers were determined by transduction and beta-galactosidase assay of TE671 cells 48 hours later.

TE671 cells were also transfected (as described above) with the packaging vector pHP-1 or an env-deletion mutant pHP-1dl.2, and compared to the wild-type HIV-1 molecular clone pNL4-3 for their packaging efficiencies. Culture supernatants were collected for RT assay and for vector titering after 48 hours. The vectors were pseudotyped with the VSV-G envelope and titered on TE671 cells. X-gal stained blue cells were counted after 48 hours.

TABLE 3

Production of High-Titer HIV-1 Derived Vectors

| Packaging Construct | Pseudotyped Envelope | Transducing Vector | Additional Genes | RT (cpm/μl) | Titer (cfu/ml) |
|---|---|---|---|---|---|
| pNL4-3 | pHEF-VSVG | pTVΔCMVnlacZ | | $1.1 \times 10^5$ | $7.9 \times 10^4$ |
| pNL-4-3 | pHEF-VSVG | pTVψCMV-nlacZ-hyg-dl.SmaI | | $7.9 \times 10^4$ | 24 |
| pHP-1 | pHEF-VSVG | pTVΔCMVnlacZ | pCEP-tat | $3.7 \times 10^4$ | $2.5 \times 10^5$ |
| pHP-1 | pHEF-VSVG | pTVψCMV-nlacZ-hyg-dl.SmaI | pCEP-tat | $3.1 \times 10^4$ | 100 |
| pHP-2dl.2 | pHEF-VSVG | pTVΔCMVnlacZ | pCEP-tat | $3.9 \times 10^4$ | $1.7 \times 10^5$ |
| pHP-1dl.2 | pHEF-VSVG | pTVψCMV-nlacZ-hyg-dl.SmaI | pCEP-tat | $3.6 \times 10^4$ | 90 |

These results indicated that pHP-1 or pHP-1dl.2 could produce HIV proteins at near the wild-type levels. In addition, both pHP constructs produced higher vector titers than did the wild-type $HIV_{NL4-3}$, suggesting that the wild-type HIV-1 genome might have interfered with the transducing vector genome for packaging. Also, the presence of additional Tat appears to enhance the vector production. This experiment also showed that the pTVψ vector was poorly packaged and need further modifications.

EXAMPLE 8

Production of RC-HIV

In order to determine whether an RC-HIV recombinant could be generated, the transfected human TE671 cells were co-cultured with the human lymphoma cell line MT4. MT4 cells are an HTLV-1 transformed human CD4+ lymphoma cell line, that are very sensitive to HIV-1 infection. These cells are available from the National Institutes of Health AIDS Reagents and Reference Program.

In this Example, it was found that the pHP1 packaging construct, but not the env-deleted constructs pHP-1dl.2 (2 nt deletion) and pHP-1dl.28 28 nt deletion), produced replication-competent HIV-1 (RCV) after co-transfection with pTV plasmid. Infectious virus was detected from pHP+pTVΔCMVnlacZ MT4 co-culture in 8 days. In addition, no infectious virus was detected from pHP.dl.2 or pHP.dl.28+pTVΔCMVnlacZ MT4 co-culture in 60 days (See, Table 4, below).

To generate HIV-1 env deletion, pHP-1 was digested at the unique restriction enzyme site NheI in the env gene, and treated with Bal31 exonuclease for 1, 2 or 5 minutes. The digested product was self-ligated after T4 DNA polymerase treatment. The self-ligated plasmid DNA was then transformed into competent E. coli DH5α and the plasmid clones containing env deletion were selected. More than six env-deleted pHP-1 clones of different lengths were selected and sequenced, as known in the art.

pHP-1dl.2 and pHP-1dl.28 have 2 and 28 nucleotide deletion in the env gene respectively (See, FIG. 5). TE671 cells were co-transfected with pHP+pTV+pHEF-VSV-G as shown in the Table below (Table 4), and the culture supernatants were harvested 48 hours after DNA removal for RT assay and vector titer was determined as described before. To detect RCV, the transfected cells were co-cultured with the human MT-4 lymphoblastoid cell line, which is very sensitive to HIV-1 infection, for up to 2 months. The culture supernatants were harvested at different time points after co-culture. To detect replication-competent HIV-1 (RCV), the supernatant from the co-culture was assayed for HIV-1 RT activity and for infectious RCV by passage onto CD4+ HeLa cells or uninfected MT4 culture. Infection of CD4+ HeLa cells was examined by anti-p24 immunohistochemical staining using pooled AIDS patients' sera, and infection of MT4 cells by cytopathic effects of RCV and the RT production. A very sensitive assay which would detect cell-cell transmission of poor replicative virus was also used. After four months of co-culture, the MT4 cells were removed and added to fresh MT4 cells and further cultured for 4 days. The co-cultured MT4 cells were fixed and immunostained with HIV patients' sera. The results showed that both pHP-1dl.2 and pHP-1dl.28 were incapable of producing RC-HIV. In sum, these results indicated that pHP-1 transfected cultures produced replication-competent HIV-1 after 8 days of co-culture. However, no RCV was detected after a 60-day co-culture for either pHP-1dl.2 or pHP-1dl.28 cotransfection. The vector titers produced by pHP-1dl.2 and pHP-1dl.28 were as high as that produced by pHP-1. The 28 nt deletion vector pHP-1dl.28 was shown to be as efficient as pHP-1, and did not produce RCV, based on the sensitive HIV infection assay. Thus, the deletion does not affect vector production efficiency and the env-deleted pHP constructs are safe for vector production without generating RCV.

FIG. 12 illustrates the possible cross-over between pHP-dl.28 and pTV-dl.CMVnlacZ, to generate RCV during co-transfection. These results clearly indicate that the recombinants are not infectious, due to the deletion in env and the LTR mutation, and requires two homologous recombination event.

TABLE 4

Detection of Replication-Competent HIV (RCV)

| Packaging Construct | Pseudotyped Envelope | Transducing Vector | Additional Genes | Days After Co-Culture | | |
|---|---|---|---|---|---|---|
| | | | | 8 | 28 | 60# |
| pNL4-3 (Control) | pHEF-VSVG | pTVΔCMV-nlacZ | | ++++ | +* | +++ |
| pHP-1 | pHEF-VSVG | pTVΔCMV-nlacZ | pCEP-tat | ++ | +++ | +++ |
| pHP-1dl.2 | pHEF-VSVG | pTVΔCMV-nlacZ | pCEP-tat | − | − | − |
| pHP-1dl.28 | pHEF-VSVG | pTVΔCMV-nlacZ | pCEP-tat | − | − | − |

*Results of rapid cell death and loss of MT4 cells.
'+ to ++++', approximately 10 to 40% of the reporter CD4-HeLa cells were HIV-positive after infection using 1 ml of supernatant.
The MT4 cells in the TE671/MT4 co-culture were transferred into a fresh MT4 culture on day 46 after co-culture; 12 days later, the MT4 cells were directly immunostained with HIV patients' sera.
'−', no infectious virus was detected.

EXAMPLE 9

Efficient Transduction of Mitomycin-C-Treated Human Cells by HP-TV Vector

In this Example, two cell cultures were transduced with HP-TV and observed for its transduction efficiency. TE671 or HeLa cells were treated with the DNA synthesis inhibitor, mitomycin C, at 10 μg/ml for 4 hours, trypsinized and plated into a 6-well culture plate. The cells were transduced with HP-TV HIV vector carrying a nlacZ marker gene in the presence of 4–8 μg/ml polybrene in a total volume of 0.5 ml for 2-3 hours and fed with growth media (DMEM containing 10% FBS). After 48 hours, the expression of the transduced lacZ gene was detected by X-gal staining as described above. The results indicated that the HP-TV vector was capable of efficiently transducing mitomycin-C-treated, non-dividing human cells.

EXAMPLE 10

Efficient Transduction of Primary Neuronal Cells by HP-TV

In this Example, rat neuronal cells were isolated from the brains of Fisher rats according to the method of Ure et al. (Ure et al., Develop. Biol., 154:388–395 [1992]). The cells were grown in culture medim containing L15CO$_2$ (GIBCO, Grand Island, N.Y.), containing 200 ng/ml 2.5 S nerve growth factor (NGF), 2.55 rat serum, 1 mg/ml ascorbic acid, and 10 μM cytosine arabinose (Sigma), to inhibit divisions of non-neuronal cells.

In addition to rat neuronal cells, human neurons and astrocytes were obtained from differentiated embryonal neural stem cells provided by Neurospheres, Ltd (Calgary, Alberta, Canada). These cells were infected with the HP-TV vectors carrying the nlacZ reporter gene as described above. Briefly, cells were incubated in culture media containing the HP-TV vector. After two hours of incubation, conditioned media (i.e., supernatant medium harvested from cultured neuronal cells after 24 hours of culture) were added, and the culture continued to incubate for five days. The cells were then fixed with formaldehyde and glutaraldehyde, and incubated with X-gal substrate as described in the β-galactosidase assay described above. The results indicated that the HP-TV vector efficiently transduces primary neuronal cells obtained from rat brains, and human neuronal stem cells (neurons and astrocytes).

EXAMPLE 11

Efficient In Vivo Transduction of Muscle Cells

In this Example, the HP-TV HIV vector was used to transduce muscle cell in vivo. The hind-legs of mice CB-17 SCID/beige mice (Taconic) were intramuscularly injected with 50–100 μl of vectors carrying the nlacZ reporter gene as unconcentrated ($10^5$/ml) or microcentrifuge concentrated (30×$10^5$/ml) stocks in the presence of 4 μg/ml of polybrene. The mice were sacrificed two days later and the injected tissue was prepared for frozen section and for β-galactosidase analysis. The results showed that HP-TV vector transduced muscle cells efficiently in vivo. In particular, tissues exposed to the concentrated vector stock were transduced at near 100% efficiency at the site of injection. It was also noticed that microcentrifuge concentration increased the infectious virus titer, but not in proportion to the fold of concentration.

EXAMPLE 12

Requirement for HIV-1 Tat for Efficient Gal-Pol Protein Processing

In this Example, the requirement of Tat for Gag-Pol processing was demonstrated. The following experiments demonstrated that HIV-1 Tat is necessary for efficient Gag-Pol protein processing and is required for efficient HIV-1 vector production.

1. Western Analysis of Tat$^+$ and Tat$^-$ HIV-1 Particles and Infected Cells

Virus pellets ("P") and cell lysates ("L") were prepared from Tat$^+$ (tat WT) and Tat$^-$ (tat-B and tat-C) virus-infected cells, and the protein contents were separated by a 10% SDS protein gel, and detected in Western analysis using AIDS patient's serum. The signals were amplified using the Amersham ECL chemiluminescence kit.

In FIG. 11, the first three lanes (1–3) indicate the results for mock-infected cells (lane 1), and virus pellets harvested from MT4 cells (lanes 2 and 3 contain viral pellet from cells chronically infected with tatC), and AA2 cells (i.e., CD4+ hybridoma human T and B cells, available from the AIDS Research and Reference Reagent Program) lane 4 contains viral pellet harvested from AA2 cells acutely infected with tatB. Cell lysates and pelleted particles of Tat$^+$ viruses grown in PBL and Molt3 cells, are shown for comparison on lanes 5 and 6 of FIG. 11. In this Figure, protein markers are shown on the left and representative structure proteins of HIV-1 are indicated on the right.

2. Gag Processing Deficiency of Tat-minus HIV-1 Demonstrated by Metabolic Labeling of Chronically Infected Cells WT or tat-minus HIV-1 chronically infected cultures were metabolically labeled with $^3$H-leucine overnight, immunoprecipitated with pooled HIV patient sera, and analyzed by SDA-PAGE (10%). The relative ratio of Gag p55:p24 is shown at the bottom. Processing of the envelope gp160 to gp120 was not significantly different between different samples. The $^3$H-labeled protein bands were quantified using a phosphoimager (BAS1000). The results are shown in FIG. 14: Lane 1, control MT4; lane 2 &3, MT4 chronically infected with dl.Sp1 CMV tat-C; lane 4, MT4 acutely infected with WT HIV-1; lane 5, C8166 chronically infected with WT HIV-1; lane 6, MT4 chronically infected with dl.Sp1 CMV tat-B; lane 7, AA2 chronically infected with dl.Sp1 CMV tat-C.

3. Cells Chronically Infected with Tat-minus HIV-1 are Deficient in Gag Protein Processing Demonstrated by Pulse-Chase Metabolic Labeling The same number of viable cells ($3 \times 10^6$) was used in each lane of a 10% SDS-PAGE gel system. Cells were labeled with medium containing bands for HIV-1 Env gp12O, and Gag p55 and p24. A Fuji phosphoimager was used for quantitation of Gag p55 and p24 of WT-infected MT4 and tat-C chronic high producer. In FIG. 10, the resultant decrease of p55 and increase of p24 (p55, p24/pulse-labeled p55) with time (P, 2, 4, 6, 8 hours) were shown and plotted. In FIG. 10, the solid curves demonstrate efficient processing of p55 of $HIV_{NL}$4-3 with steady increase of p24 and decrease of p55; the dashed curves demonstrate that the amounts of p55 and p24 are not significantly changed with time in the tat-C high producer cells, indicating a deficiency in Gag processing.

4. Tat Enhances Gag Processing in HeLa cells

HeLa cells were transfected with plasmid DNA encoding HIV-1 Gag, Rev, Tat, HTLV Tax/Rex, SIV Tat, or HIV Tat exon 1 as indicated in FIG. 16. The results shown in FIG. 16, clearly demonstrate that Tat enhances p55 to p24 Gag processing. The effect of Tat on Gag processing is TAR-independent as GagTAR-construct which has TAR deletion is also sensitive to this Tat effect. This function of Tat resides in the exon 1 which can be partially restored by SIVTat and HTLV Tax/Rex.

5. Tat Enhances Gag Processing From the pHP-VSV-G Packaging Construct

TE671 cells were transfected with plasmids as described above. Cell lysates were harvested 24 hours after DNA removal and analyzed by SDS-PAGE and Western blotting as described using anti-p24 MAb. The result indicated that Gag processing is enhanced by the presence of Tat (See, lane 2 vs. lane 3, and lane 5 vs. lane 6 in FIG. 16).

EXAMPLE 13

HIV Vectors are More Efficent than MLV Vectors

In this Example, HIV vectors were compared with the standard MLV vectors commonly in use. The results obtained in these experiments indicated that HIV vector is more efficient than the MLV vector. In this example, a MLV-derived vector (MFGnlacZ, obtainable from Dr. Richard Mulligan) and the HIV-1 derived pHP-1dl.28+ pTVΔCMVnlacZ vectors were involved in a long term transduction and gene expression study. Three different human cells lines (TE671, 293, and HepG2) were used in these experiments. The cells were transduced as described, three times in three days using virus stocks prepared from vector producing cells (transfection of PA317 for MFGnlacZ, approximately $10^5$ cfu/ml and transfection of 293 for HIV-1 vector, approximate $10^5$cfu/ml). The cells were transduced three times and propagated once before staining for beta-galactosidase expression.

Briefly, the transduced cells were grown for 3 days and trypsinized, the number of cells was determined, the cells were then plated into 6-well culture plates and one day later, the cells were stained for beta-galactosidase activity. The number of blue cells were counted and the percentages of blue cell in the wells were determined under an inverted microscope. The results suggest that the HIV-1 derived vectors can transduce all three cell types at higher efficiencies than the MLV vector, at ranges from 3 to 10 folds. These cells were also passaged for 48 days, and stained for β-galactosidase activity again. The results showed that in the long term culture, the HP+TV HIV vectors exhibited gene expression stability.

Table 5 below, shows a direct comparison of the transduction efficiencies observed at 48 hours and 48 days. As previously mentioned, TE671 are rhabdomyosarcoma cells, 293 are kidney cells, and HepG2 are hepatoma cells. In this table, the numbers indicate the percent of cells transduced after one passage or multiple passages (for the 48 hour samples, the cells were transduced three times and propagated once, before staining for β-galactosidase activity as previously described in Example 6.

TABLE 5

Comparison of Long-Term Transduction Efficiencies

| Cell Lines | Transduction Efficiencies of MLV vs. HIV nlacZ Vectors | | | |
|---|---|---|---|---|
| | 48 Hours | | 48 Days | |
| | MLV | HIV | MLV | HIV |
| HepG2 | 3 ± 2 | 29 ± 7 | 15 ± 0.2 | 27 ± 4 |
| TE671 | 20 ± 4 | 60 ± 2 | 12 ± 2 | 45 ± 2 |
| 293T | 7 ± 0.1 | 46 ± 2 | 1.2 ± 0.2 | 13 ± 3 |

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A packaging vector comprising a nucleotide sequence encoding Gag and Pol proteins of a reference lentivirus, said packaging vector differing from said reference lentivirus at least in that
    (a) it lacks a functional major splice donor site, or its manor splice donor site, while functional, differs in sequence from that of said reference lentivirus, and
    (b) it lacks a functional major packaging signal, which vector, after introduction into a suitable host cell, is capable of causing such cell, either through expression from said vector alone, or through co-expression from said vector and a second vector providing for expression of a compatible envelope protein, to produce packaging vector particles comprising functional Gag and Pol proteins and having a normal or a pseudotyped envelope, where said particles are free of the RNA form of said packaging vector as a result of (b) above,
    where said cell, as a result of said expression or co-expression, produces particles encapsulating the RNA form of a transducing vector possessing a compatible and functional packaging signal if said transducing vector is introduced into said cell,
    where said reference lentivirus is a human or simian immunodeficiency virus.

2. The packaging vector of claim 1 in which the reference lentivirus is HIV-1.

3. The packaging vector of claim 1 in which the reference lentivirus is HIV-2.

4. The packaging vector of claim 1 in which the reference lentivirus is SIV.

5. The packaging vector of claim 1 which encodes one or more envelope proteins.

6. The packaging vector of claim 1 which does not encode a functional envelope protein.

7. The packaging vector of claim 1 wherein the major splice donor site of said vector differs in sequence from that of any lentivirus major splice donor site sufficiently so that said major splice donor site is not a potential site for homologous recombination between said packaging vector and any HIV or SIV.

8. The packaging vector of claim 1 which comprises a sequence encoding a lentivirus Env proteins.

9. The packaging vector of claim 1 which comprises a sequence encoding the VSV-G envelope protein.

10. The packaging vector of claim 1 which further differs from said reference lentivirus in that at least portions of at least one gene selected from the group consisting of the env, vpr, vif, and vpu genes of said reference lentivirus is or are deleted.

11. The packaging vector of claim 1 which lacks the native primer binding site of said reference lentivirus.

12. The packaging vector of claim 1 which lacks the native polypurine tract of said reference lentivirus.

13. The packaging vector of claim 1 which lacks a functional nef gene.

14. The packaging vector of claim 1 which further differs from said lentivirus in that the 5' LTR has been modified.

15. The packaging vector of claim 1 in which the 5'LTR is a chimera of a lentivirus LTR and a CMV enhancer/promoter.

16. The packaging vector of claim 1 comprises a tat gene and a TAR sequence.

17. The packaging vector of claim 1 which comprises a rev gene and an RRE element.

18. The packaging vector of claim 1 which further differs from the reference lentivirus in that at least a portion of the tat gene and the TAR sequence are deleted.

19. The packaging vector of claim 1 which further differs from the reference lentivirus in that at least a portion of the env gene and the RRE element are deleted.

20. A packaging cell which comprises the packaging vector of claim 1 and is suitable for production of packaging or transducing vector particles.

21. A method of a producing a transducing vector comprising a remedial gene, in the form of an infectious particle, which comprises
    (a) transfecting a cell with a packaging vector according to claim 1, and, if said packaging vector does not itself provide for expression of a compatible envelope protein, a pseudotyping vector which does provide expression, so said cell is capable of producing packaging vector particles,
    (b) transfecting said cell with a transducing vector comprising said remedial gene, and a functional packaging signal, but which by itself is incapable of causing a cell to produce transducing vector particles, and
    (c) causing the cell to produce infectious transducing vector particles comprising said transducing vector in RNA form, said Gag and Pol proteins, and said envelope protein.

22. A kit comprising a packaging vector according to claim 1 and a transducing vector comprising a functional and compatible packaging signal, said transducing vector being incapable by itself of causing a cell transfected by said tranducing vector to encapsulate the RNA form of said transducing vector into a transducing vector particle.

23. The packaging vector of claim 1 in which the major splice donor site is a modified RSV major splice donor site corresponding to the splice donor site included in SEQ ID NO:9 and SEQ ID NO:10.

24. The packaging vector of claim 1 where said major splice donor site is functional but differs in sequence from that of all HIV and SIV lentivirus splice donor sites.

25. The packaging vector of claim 1 which lacks a functional major splice donor site.

26. The packaging vector of claim 1 where its major splice donor site, while functional, differs in sequence from that of said reference lentivirus sufficiently so that homologous recombination between said packaging vector and said reference lentivirus at said splice donor site is not detectable.

27. The vector of claim 1, wherein at least a portion of the env gene of said reference lentivirus is deleted.

28. The packaging vector of claim 7 wherein the major splice donor site of said vector is substantially identical to the RSV splice donor site.

29. The cell of claim 20, which further comprises a pseudotyping vector.

30. The cell of claim 20 which further comprises a transducing vector which by itself is incapable of coding for expression of infectious transducing vector particles, but which cell, as a result of the expression of genes of said packaging vector, packages the RNA form of said transducing vector into infectious transducing vector particles.

31. The cell of claim 20 where said transducing vector further comprises a remedial gene.

32. The cell of claim 20 wherein packaging is inducible.

33. The kit of claim 22, said packaging vector comprising a gene encoding a compatible envelope protein.

34. The kit of claim 22, further comprising a pseudotyping vector comprising a gene encoding a non-lentiviral envelope protein incorporatable into said particles.

35. The packaging vector of claim 26 in which the absence of detectable homologous recombination is demonstrated by failure to detect replication-competent virus transfecting human TE671 cells with the packaging vector, co-culturing the TE671 cells with the human hymphoma cell line MT4 for two months, and determining, by immunohistochemical methods, whether the MT4 cells are producing HIV-1 proteins.

36. The vector of claim 27 in which the deletion is a frame shift mutation.

37. The vector of claim 27 in which two nucleotides of the env gene are deleted.

38. The vector of claim 27 in which 28 nucleotides of the env gene are deleted.

39. The vector of claim 27 in which the deletion is one achievable by Bal31 digestion at the unique NheI site in the env gene of wild-type HIV strain pNL4-3 or at the corresponding position in another reference lentivirus.

40. The vector of claim 35 where the presence of replication-competent virus is detected by determining by immunohistochemical methods whether the MT4 cells are producing HIV-1 proteins.

\* \* \* \* \*

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
      (A) LENGTH: 6145 base pairs
      (B) TYPE: nucleic acid
      (C) STRANDEDNESS: double
      (D) TOPOLOGY: linear (ii) MOLECULE TYPE: DNA (genomic)

(xi) SEQUENCE DESCRIPTION: SEQ ID NO:1:

```
GAATTCATAC CAGATCACCG AAAACTGTCC TCCAAATGTG TCCCCCTCAC ACTCCCAAAT      60
TCGCGGGCTT CTGCCTCTTA GACCACTCTA CCCTATTCCC CACACTCACC GGAGCCAAAG     120
CCGCGGCCCT TCCGTTTCTT TGCTTTTGAA AGACCCCACC CGTAGGTGGC AAGCTAGCTT     180
AAGTAACGCC ACTTTGCAAG GCATGGAAAA ATACATAACT GAGAATAGAA AAGTTCAGAT     240
CAAGGTCAGG AACAAAGAAA CAGCTGAATA CCAAACAGGA TATCTGTGGT AAGCGGTTCC     300
TGCCCCGGCT CAGGGCCAAG AACAGATGAG ACAGCTGAGT GATGGGCCAA ACAGGATATC     360
TGTGGTAAGC AGTTCCTGCC CCGGCTCGGG GCCAAGAACA GATGGTCCCC AGATGCGGTC     420
CAGCCCTCAG CAGTTTCTAG TGAATCATCA GATGTTTCCA GGGTGCCCCA AGGACCTGAA     480
AATGACCCTG TACCTTATTT GAACTAACCA ATCAGTTCGC TTCTCGCTTC TGTTCGCGCG     540
CTTCCGCTCT CCGAGCTCAA TAAAAGAGCC CACAACCCCT CACTCGGCGC GCCAGTCTTC     600
CGATAGACTG CGTCGCCCGG GTACCCGTAT TCCCAATAAA GCCTCTTGCT GTTTGCATCC     660
GAATCGTGGT CTCGCTGTTC CTTGGGAGGG TCTCCTCTGA GTGATTGACT ACCCACGACG     720
GGGGTCTTTC ATTTGGGGGC TCGTCCGGGA TTTGGAGACC CCTGCCCAGG GACCACCGAC     780
CCACCACCGG GAGGTAAGCT GGCCAGCAAC TTATCTGTGT CTGTCCGATT GTCTAGTGTC     840
TATGTTTGAT GTTATGCGCC TGCGTCTGTA CTAGTTAGCT AACTAGCTCT GTATCTGGCG     900
GACCCGTGGT GGAACTGACG AGTTCTGAAC ACCCGGCCGC AACCCTGGGA GACGTCCCAG     960
GGACTTTGGG GGCCGTTTTT GTGGCCCGAC CTGAGGAAGG GAGTCGATGT GGAATCCGAC    1020
CCCGTCAGGA TATGTGGTTC TGGTAGGAGA CGAGAACCTA AAACAGTTCC CGCCTCCGTC    1080
TGAATTTTTG CTTTCGGTTT GGAACCGAAG CCGCGCGTCT TGTCTGCTGC AGCGCTGCAG    1140
CATCGTTCTG TGTTGTCTCT GTCTGACTGT GTTTCTGTAT TTGTCTGAAA ATTAGGGCCA    1200
GACTGTTACC ACTCCCTTAA GTTTGACCTT AGGTCACTGG AAAGATGTCG AGCGGATCGC    1260
TCACAACCAG TCGGTAGATG TCAAGAAGAG ACGTTGGGTT ACCTTCTGCT CTGCAGAATG    1320
GCCAACCTTT AACGTCGGAT GGCCGCGAGA CGGCACCTTT AACCGAGACC TCATCACCCA    1380
GGTTAAGATC AAGGTCTTTT CACCTGGCCC GCATGGACAC CCAGACCAGG TCCCCTACAT    1440
CGTGACCTGG GAAGCCTTGG CTTTTGACCC CCCTCCCTGG GTCAAGCCCT TTGTACACCC    1500
TAAGCCTCCG CCTCCTCTTC CTCCATCCGC CCCGTCTCTC CCCCTTGAAC CTCCTCGTTC    1560
GACCCCGCCT CGATCCTCCC TTTATCCAGC CCTCACTCCT TCTCTAGGCG CCGGAATTCC    1620
GATCTGATCA AGAGACAGGA TGAGGATCGT TTCGCATGAT TGAACAAGAT GGATTGCACG    1680
CAGGTTCTCC GGCCGCTTGG GTGGAGAGGC TATTCGGCTA TGACTGGGCA CAACAGACAA    1740
TCGGCTGCTC TGATGCCGCC GTGTTCCGGC TGTCAGCGCA GGGGCGCCCG GTTCTTTTTG    1800
```

-continued

| | |
|---|---|
| TCAAGACCGA CCTGTCCGGT GCCCTGAATG AACTGCAGGA CGAGGCAGCG CGGCTATCGT | 1860 |
| GGCTGGCCAC GACGGGCGTT CCTTGCGCAG CTGTGCTCGA CGTTGTCACT GAAGCGGGAA | 1920 |
| GGGACTGGCT GCTATTGGGC GAAGTGCCGG GGCAGGATCT CCTGTCATCT CACCTTGCTC | 1980 |
| CTGCCGAGAA AGTATCCATC ATGGCTGATG CAATGCGGCG GCTGCATACG CTTGATCCGG | 2040 |
| CTACCTGCCC ATTCGACCAC CAAGCGAAAC ATCGCATCGA GCGAGCACGT ACTCGGATGG | 2100 |
| AAGCCGGTCT TGTCGATCAG GATGATCTGG ACGAAGAGCA TCAGGGGCTC GCGCCAGCCG | 2160 |
| AACTGTTCGC CAGGCTCAAG GCGCGCATGC CCGACGGCGA GGATCTCGTC GTGACCCATG | 2220 |
| GCGATGCCTG CTTGCCGAAT ATCATGGTGG AAAATGGCCG CTTTTCTGGA TTCATCGACT | 2280 |
| GTGGCCGGCT GGGTGTGGCG GACCGCTATC AGGACATAGC GTTGGCTACC CGTGATATTG | 2340 |
| CTGAAGAGCT TGGCGGCGAA TGGGCTGACC GCTTCCTCGT GCTTTACGGT ATCGCCGCTC | 2400 |
| CCGATTCGCA GCGCATCGCC TTCTATCGCC TTCTTGACGA GTTCTTCTGA GCGGGACTCT | 2460 |
| GGGGTTCGAA ATGACCGACC AAGCGACGCC CAACCTGCCA TCACGAGATT TCGATTCCAC | 2520 |
| CGCCGCCTTC TATGAAAGGT TGGGCTTCGG AATCGTTTTC CGGGACGCCG GCTGGATGAT | 2580 |
| CCTCCAGCGC GGGGATCTCA TGCTGGAGTT CTTCGCCCAC CCCGGGCTCG ATCCCCTCGC | 2640 |
| GAGTTGGTTC AGCTGCTGCC TGAGGCTGGA CGACCTCGCG GAGTTCTACC GGCAGTGCAA | 2700 |
| ATCCGTCGGC ATCCAGGAAA CCAGCAGCGG CTATCCGCGC ATCCATGCCC CCGAACTGCA | 2760 |
| GGAGTGGGGA GGCACGATGG CCGCTTTGGT CGACCCGGAC GGGACGCTCC TGCGCCTGAT | 2820 |
| ACAGAACGAA TTGCTTGCAG GCATCTCATG AGTGTGTCTT CCCGTTTTCC GCCTGAGGTC | 2880 |
| ACTGCGTGGA TGGAGCGCTG GCGCCTGCTG CGCGACGGCG AGCTGCTCAC CACCCACTCG | 2940 |
| AGGGCGTGCA GCGCTGCAGA GGCCGAGTGC AGAACTGCTC CAAAGGGACC TCAAGGCTTT | 3000 |
| CCGAGGGACA CTAGGCTGAC TCCATCGAGC CAGTGTAGAG ATAAGCTTAT CGATTAGTCC | 3060 |
| AATTTGTTAA AGACAGGATA TCAGTGGTCC AGGCTCTAGT TTTGACTCAA CAATATCACC | 3120 |
| AGCTGAAGCC TATAGAGTAC GAGCCATAGA TAAAATAAAA GATTTTATTT AGTCTCCAGA | 3180 |
| AAAAGGGGGG AATGAAAGAC CCCACCTGTA GGTTTGGCAA GCTAGCTTAA GTAACGCCAT | 3240 |
| TTTGCAAGGC ATGGAAAAAT ACATAACTGA GAATAGAGAA GTTCAGATCA AGGTCAGGAA | 3300 |
| CAGATGGAAC AGCTGAATAT GGGCCAAACA GGATATCTGT GGTAAGCAGT TCCTGCCCCG | 3360 |
| GCTCAGGGCC AAGAACAGAT GGAACAGCTG AATATGGGCC AAACAGGATA TCTGTGGTAA | 3420 |
| GCAGTTCCTG CCCCGGCTCA GGGCCAAGAA CAGATGGTCC CCAGATGCGG TCCAGCCCTC | 3480 |
| AGCAGTTTCT AGAGAACCAT CAGATGTTTC CAGGGTGCCC CAAGGACCTG AAATGACCCT | 3540 |
| GTGCCTTATT TGAACTAACC AATCAGTTCG CTTCTCGCTT CTGTTCGCGC GCTTCTGCTC | 3600 |
| CCCGAGCTCA ATAAAAGAGC CCACAACCCC TCACTCGGGG CGCCAGTCCT CCGATTGACT | 3660 |
| GAGTCGCCCG GGTACCCGTG TATCCAATAA ACCCTCTTGC AGTTGCATCC GACTTGTGGT | 3720 |
| CTCGCTGTTC CTTGGGAGGG TCTCCTCTGA GTGATTGACT ACCCGTCAGC GGGGGTCTTT | 3780 |
| CATTTGGGGG CTCGTCCGGG ATCGGAGAC CCCTGCCCAG GACCACCGA CCCACCACCG | 3840 |
| GGAGGTAAGC TGGCTGCCTC GCGCGTTTCG GTGATGACGG TGAAAACCTC TGACACATGC | 3900 |
| AGCTCCCGGA GACGGTCACA GCTTGTCTGT AAGCGGATGC CGGGAGCAGA CAAGCCCGTC | 3960 |
| AGGGCGCGTC AGCGGGTGTT GGCGGGTGTC GGGGCGCAGC CATGACCCAG TCACGTAGCG | 4020 |
| ATAGCGGAGT GTATACTGGC TTAACTATGC GGCATCAGAG CAGATTGTAC TGAGAGTGCA | 4080 |
| CCATATGCGG TGTGAAATAC CGCACAGATG CGTAAGGAGA AAATACCGCA TCAGGCGCTC | 4140 |

-continued

```
TTCCGCTTCC TCGCTCACTG ACTCGCTGCG CTCGGTCGTT CGGCTGCGGC GAGCGGTATC    4200

AGCTCACTCA AAGGCGGTAA TACGGTTATC CACAGAATCA GGGGATAACG CAGGAAAGAA    4260

CATGTGAGCA AAAGGCCAGC AAAAGGCCAG GAACCGTAAA AAGGCCGCGT TGCTGGCGTT    4320

TTTCCATAGG CTCCGCCCCC CTGACGAGCA TCACAAAAAT CGACGCTCAA GTCAGAGGTG    4380

GCGAAACCCG ACAGGACTAT AAAGATACCA GGCGTTTCCC CCTGGAAGCT CCCTCGTGCG    4440

CTCTCCTGTT CCGACCCTGC CGCTTACCGG ATACCTGTCC GCCTTTCTCC CTTCGGGAAG    4500

CGTGGCGCTT TCTCATAGCT CACGCTGTAG GTATCTCAGT TCGGTGTAGG TCGTTCGCTC    4560

CAAGCTGGGC TGTGTGCACG AACCCCCCGT TCAGCCCGAC CGCTGCGCCT TATCCGGTAA    4620

CTATCGTCTT GAGTCCAACC CGGTAAGACA CGACTTATCG CCACTGGCAG CAGCCACTGG    4680

TAACAGGATT AGCAGAGCGA GGTATGTAGG CGGTGCTACA GAGTTCTTGA AGTGGTGGCC    4740

TAACTACGGC TACACTAGAA GGACAGTATT TGGTATCTGC GCTCTGCTGA AGCCAGTTAC    4800

CTTCGGAAAA AGAGTTGGTA GCTCTTGATC CGGCAAACAA ACCACCGCTG GTAGCGGTGG    4860

TTTTTTTGTT TGCAAGCAGC AGATTACGCG CAGAAAAAAA GGATCTCAAG AAGATCCTTT    4920

GATCTTTTCT ACGGGGTCTG ACGCTCAGTG GAACGAAAAC TCACGTTAAG GGATTTTGGT    4980

CATGAGATTA TCAAAAAGGA TCTTCACCTA GATCCTTTTA AATTAAAAAT GAAGTTTTAA    5040

ATCAATCTAA AGTATATATG AGTAAACTTG GTCTGACAGT TACCAATGCT TAATCAGTGA    5100

GGCACCTATC TCAGCGATCT GTCTATTTCG TTCATCCATA GTTGCCTGAC TCCCCGTCGT    5160

GTAGATAACT ACGATACGGG AGGGCTTACC ATCTGGCCCC AGTGCTGCAA TGATACCGCG    5220

AGACCCACGC TCACCGGCTC CAGATTTATC AGCAATAAAC CAGCCAGCCG GAAGGGCCGA    5280

GCGCAGAAGT GGTCCTGCAA CTTTATCCGC CTCCATCCAG TCTATTAATT GTTGCCGGGA    5340

AGCTAGAGTA AGTAGTTCGC CAGTTAATAG TTTGCGCAAC GTTGTTGCCA TTGCTGCAGG    5400

CATCGTGGTG TCACGCTCGT CGTTTGGTAT GGCTTCATTC AGCTCCGGTT CCCAACGATC    5460

AAGGCGAGTT ACATGATCCC CCATGTTGTG CAAAAAAGCG GTTAGCTCCT TCGGTCCTCC    5520

GATCGTTGTC AGAAGTAAGT TGGCCGCAGT GTTATCACTC ATGGTTATGG CAGCACTGCA    5580

TAATTCTCTT ACTGTCATGC CATCCGTAAG ATGCTTTTCT GTGACTGGTG AGTACTCAAC    5640

CAAGTCATTC TGAGAATAGT GTATGCGGCG ACCGAGTTGC TCTTGCCCGG CGTCAACACG    5700

GGATAATACC GCGCCACATA GCAGAACTTT AAAAGTGCTC ATCATTGGAA AACGTTCTTC    5760

GGGGCGAAAA CTCTCAAGGA TCTTACCGCT GTTGAGATCC AGTTCGATGT AACCCACTCG    5820

TGCACCCAAC TGATCTTCAG CATCTTTTAC TTTCACCAGC GTTTCTGGGT GAGCAAAAAC    5880

AGGAAGGCAA AATGCCGCAA AAAAGGGAAT AAGGGCGACA CGGAAATGTT GAATACTCAT    5940

ACTCTTCCTT TTTCAATATT ATTGAAGCAT TTATCAGGGT TATTGTCTCA TGAGCGGATA    6000

CATATTTGAA TGTATTTAGA AAAATAAACA ATAGGGGTT CCGCGCACAT TTCCCCGAAA    6060

AGTGCCACCT GACGTCTAAG AAACCATTAT TATCATGACA TTAACCTATA AAAATAGGCG    6120

TATCACGAGG CCCTTTCGTC TTCAA                                         6145
```

(2) INFORMATION FOR SEQ ID NO:2:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = ""DNA""

(xi) SEQUENCE DESCRIPTION: SEQ ID NO:2:

CTCAGGTACC TTTAAGACCA ATGACTTACA A                               31

(2) INFORMATION FOR SEQ ID NO:3:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = ""DNA""

(xi) SEQUENCE DESCRIPTION: SEQ ID NO:3:

CTCAGGTACC TTTAAGACTC TAGATCTAGA A                               31

(2) INFORMATION FOR SEQ ID NO:4:

(i) SEQUENCE CHARACTERISTICS:
        (A) LENGTH: 140 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = ""DNA""

(xi) SEQUENCE DESCRIPTION: SEQ ID NO:4:

AGGCGTTACT CGACAGAGGA GAGCAAGAAA TGGAGCCAGT AGATCCTAGA CTAGAGCCCT   60

GGAAGCATCC AGGAAGTCAG CCTAAAACTG CTTGTACCAA TTGCTATTGT AAAAAGTGTT  120

GCTTTCATTG CCAAGTTTGT                                             140

(2) INFORMATION FOR SEQ ID NO:5:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = ""DNA""

(xi) SEQUENCE DESCRIPTION: SEQ ID NO:5:

TATAAGATGG GTGGCAAGTG GTCAAAAAGT AGTGTGATTG GATGGCCTGC TGTAAGGGAA   60

AGAATGAGAC                                                         70

(2) INFORMATION FOR SEQ ID NO:6:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = ""DNA""

(xi) SEQUENCE DESCRIPTION: SEQ ID NO:6:

CTCAGGTACC TTTAAGACCA ATGACTTACA AGGCAGCTGT AGATCTTAGC CACTTTTTAA   60

AAGAAAAGGG                                                         70

(2) INFORMATION FOR SEQ ID NO:7:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = ""DNA""

(xi) SEQUENCE DESCRIPTION: SEQ ID NO:7:

GCGGCGACTG GGGAGGACGC CAA                                              23

(2) INFORMATION FOR SEQ ID NO:8:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = ""DNA""

(xi) SEQUENCE DESCRIPTION: SEQ ID NO:8:

GAAGGAGAGA GTTGGGTGCG AG                                               22

(2) INFORMATION FOR SEQ ID NO:9:

(i) SEQUENCE CHARACTERISTICS:
            (A) LENGTH: 55 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = ""DNA""

(xi) SEQUENCE DESCRIPTION: SEQ ID NO:9:

AGCTTGGTCG CCCGGTGGAT CAAGACCGGT AGCCGTCATA AAGGTGATTT CGTCG           55

(2) INFORMATION FOR SEQ ID NO:10:

(i) SEQUENCE CHARACTERISTICS:
            (A) LENGTH: 55 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = ""DNA""

(xi) SEQUENCE DESCRIPTION: SEQ ID NO:10:

GATCCGACGA AATCACCTTT ATGACGGCTA CCGGTCTTGA TCCACCGGGC GACCA           55

(2) INFORMATION FOR SEQ ID NO:11:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = ""DNA""

(xi) SEQUENCE DESCRIPTION: SEQ ID NO:11:

CGGGATCCAC CATGGGTGCG AGAGCGTC                                         28

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = ""DNA""

(xi) SEQUENCE DESCRIPTION: SEQ ID NO:12:

```
ATCCTATTTG TTCCTGAAGG                                          20
```

(2) INFORMATION FOR SEQ ID NO:13:

(i) SEQUENCE CHARACTERISTICS:
        (A) LENGTH: 12494 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = ""DNA""

(xi) SEQUENCE DESCRIPTION: SEQ ID NO:13:

```
CACGTGGCCC GAGAGCTGCA TCCGGAGTAT CTAGATGGAG TTCCGCGTTA CATAACTTAC     60
GGTAAATGGC CCGCCTGGCT GACCGCCCAA CGACCCCGC CCATTGACGT CAATAATGAC    120
TGATGTTCCC ATAGTAACGC CAATAGGGAC TTTCCATTGA CGCTAATGGG AGTTTGTTTT    180
GGCACCAAAA TCAACGGGAC TTTCCAAAAT GTCGTAATAA CCCCGCCCCG TTGACGCAAA    240
TGGGCGGTAG GCGTGTACTC TAGAAGGTCT ATATAAGCAG AGCTCGTTTA GTGAACCGTT    300
TATACTACTT ATCTGGTCTC TCTGGTTAGA CCAGATCTGA GCCTGGGAGC TCTCTGGCTA    360
ACTAGGGAAC CCACTGCTTA AGCCTCAATA AAGCTTTGGT CGCCCGGTGG ATCAAGACCG    420
GTAGCCGTCA TAAAGGTGAT TTCGTCGGAT CCACCGAGAG ATGGGTGCGA GAGCGTCGGT    480
ATTAAGCGGG GGAGAATTAG ATAAATGGGA AAAAATTCGG TTAAGGCCAG GGGGAAAGAA    540
ACAATATAAA CTAAAACATA TAGTATGGGC AAGCAGGGAG CTAGAACGAT TCGCAGTTAA    600
TCCTGGCCTT TTAGAGACAT CAGAAGGCTG TAGACAAATA CTGGGACAGC TACAACCATC    660
CCTTCAGACA GGATCAGAAG AACTTAGATC ATTATATAAT ACAATAGCAG TCCTCTATTG    720
TGTGCATCAA AGGATAGATG TAAAAGACAC CAAGGAAGCC TTAGATAAGA TAGAGGAAGA    780
GCAAAACAAA AGTAAGAAAA AGGCACAGCA AGCAGCAGCT GACACAGGAA ACAACAGCCA    840
GGTCAGCCAA AATTACCCTA TAGTGCAGAA CCTCCAGGGG CAAATGGTAC ATCAGGCCAT    900
ATCACCTAGA ACTTTAAATG CATGGGTAAA AGTAGTAGAA GAGAAGGCTT TCAGCCCAGA    960
AGTAATACCC ATGTTTTCAG CATTATCAGA AGGAGCCACC CCACAAGATT TAAATACCAT   1020
GCTAAACACA GTGGGGGGAC ATCAAGCAGC CATGCAAATG TTAAAAGAGA CCATCAATGA   1080
GGAAGCTGCA GAATGGGATA GATTGCATCC AGTGCATGCA GGGCCTATTG CACCAGGCCA   1140
GATGAGAGAA CCAAGGGGAA GTGACATAGC AGGAACTACT AGTACCCTTC AGGAACAAAT   1200
AGGATGGATG ACACATAATC CACCTATCCC AGTAGGAGAA ATCTATAAAA GATGGATAAT   1260
CCTGGGATTA AATAAAATAG TAAGAATGTA TAGCCCTACC AGCATTCTGG ACATAAGACA   1320
AGGACCAAAG GAACCCTTTA GAGACTATGT AGACCGATTC TATAAAACTC TAAGAGCCGA   1380
GCAAGCTTCA CAAGAGGTAA AAAATTGGAT GACAGAAACC TTGTTGGTCC AAAATGCGAA   1440
CCCAGATTGT AAGACTATTT TAAAAGCATT GGGACCAGGA GCGACACTAG AAGAAATGAT   1500
```

-continued

```
GACAGCATGT CAGGGAGTGG GGGGACCCGG CCATAAAGCA AGAGTTTTGG CTGAAGCAAT     1560

GAGCCAAGTA ACAAATCCAG CTACCATAAT GATACAGAAA GGCAATTTTA GGAACCAAAG     1620

AAAGACTGTT AAGTGTTTCA ATTGTGGCAA AGAAGGGCAC ATAGCCAAAA ATTGCAGGGC     1680

CCCTAGGAAA AAGGGCTGTT GGAAATGTGG AAAGGAAGGA CACCAAATGA AAGATTGTAC     1740

TGAGAGACAG GCTAATTTTT TAGGGAAGAT CTGGCCTTCC CACAAGGGAA GGCCAGGGAA     1800

TTTTCTTCAG AGCAGACCAG AGCCAACAGC CCCACCAGAA GAGAGCTTCA GGTTTGGGGA     1860

AGAGACAACA ACTCCCTCTC AGAAGCAGGA GCCGATAGAC AAGGAACTGT ATCCTTTAGC     1920

TTCCCTCAGA TCACTCTTTG GCAGCGACCC CTCGTCACAA TAAAGATAGG GGGCAATTA      1980

AAGGAAGCTC TATTAGATAC AGGAGCAGAT GATACAGTAT TAGAAGAAAT GAATTTGCCA     2040

GGAAGATGGA AACCAAAAAT GATAGGGGGA ATTGGAGGTT TTATCAAAGT AGGACAGTAT     2100

GATCAGATAC TCATAGAAAT CTGCGGACAT AAAGCTATAG GTACAGTATT AGTAGGACCT     2160

ACACCTGTCA ACATAATTGG AAGAAATCTG TTGACTCAGA TTGGCTGCAC TTTAAATTTT     2220

CCCATTAGTC CTATTGAGAC TGTACCAGTA AAATTAAAGC CAGGAATGGA TGGCCCAAAA     2280

GTTAAACAAT GGCCATTGAC AGAAGAAAAA ATAAAAGCAT TAGTAGAAAT TTGTACAGAA     2340

ATGGAAAAGG AAGGAAAAAT TTCAAAAATT GGGCCTGAAA ATCCATACAA TACTCCAGTA     2400

TTTGCCATAA AGAAAAAGA CAGTACTAAA TGGAGAAAAT TAGTAGATTT CAGAGAACTT      2460

AATAAGAGAA CTCAAGATTT CTGGGAAGTT CAATTAGGAA TACCACATCC TGCAGGGTTA     2520

AAACAGAAAA AATCAGTAAC AGTACTGGAT GTGGGCGATG CATATTTTTC AGTTCCCTTA     2580

GATAAAGACT TCAGGAAGTA TACTGCATTT ACCATACCTA GTATAAACAA TGAGACACCA     2640

GGGATTAGAT ATCAGTACAA TGTGCTTCCA CAGGGATGGA AAGGATCACC AGCAATATTC     2700

CAGTGTAGCA TGACAAAAAT CTTAGAGCCT TTTAGAAAAC AAAATCCAGA CATAGTCATC     2760

TATCAATACA TGGATGATTT GTATGTAGGA TCTGACTTAG AAATAGGGCA GCATAGAACA     2820

AAAATAGAGG AACTGAGACA ACATCTGTTG AGGTGGGGAT TTACCACACC AGACAAAAAA     2880

CATCAGAAAG AACCTCCATT CCTTTGGATG GGTTATGAAC TCCATCCTGA TAAATGGACA     2940

GTACAGCCTA TAGTGCTGCC AGAAAAGGAC AGCTGGACTG TCAATGACAT ACAGAAATTA     3000

GTGGGAAAAT TGAATTGGGC AAGTCAGATT TATGCAGGGA TTAAAGTAAG GCAATTATGT     3060

AAACTTCTTA GGGGAACCAA AGCACTAACA GAAGTAGTAC CACTAACAGA AGAAGCAGAG     3120

CTAGAACTGG CAGAAAACAG GGAGATTCTA AAAGAACCGG TACATGGAGT GTATTATGAC     3180

CCATCAAAAG ACTTAATAGC AGAAATACAG AAGCAGGGGC AAGGCCAATG GACATATCAA     3240

ATTTATCAAG AGCCATTTAA AAATCTGAAA ACAGGAAAAT ATGCAAGAAT GAAGGGTGCC     3300

CACACTAATG ATGTGAAACA ATTAACAGAG GCAGTACAAA AAATAGCCAC AGAAAGCATA     3360

GTAATATGGG GAAAGACTCC TAAATTTAAA TTACCCATAC AAAAGGAAAC ATGGGAAGCA     3420

TGGTGGACAG AGTATTGGCA AGCCACCTGG ATTCCTGAGT GGGAGTTTGT CAATACCCCT     3480

CCCTTAGTGA AGTTATGGTA CCAGTTAGAG AAAGAACCCA TAATAGGAGC AGAAACTTTC     3540

TATGTAGATG GGGCAGCCAA TAGGGAAACT AAATTAGGAA AAGCAGGATA TGTAACTGAC     3600

AGAGGAAGAC AAAAAGTTGT CCCCCTAACG GACACAACAA ATCAGAAGAC TGAGTTACAA     3660

GCAATTCATC TAGCTTTGCA GGATTCGGGA TTAGAAGTAA ACATAGTGAC AGACTCACAA     3720

TATGCATTGG GAATCATTCA AGCACAACCA GATAAGAGTG AATCAGAGTT AGTCAGTCAA     3780

ATAATAGAGC AGTTAATAAA AAAGGAAAAA GTCTACCTGG CATGGGTACC AGCACACAAA     3840

GGAATTGGAG GAAATGAACA AGTAGATGGG TTGGTCAGTG CTGGAATCAG GAAAGTACTA     3900
```

```
TTTTTAGATG GAATAGATAA GGCCCAAGAA GAACATGAGA AATATCACAG TAATTGGAGA    3960

GCAATGGCTA GTGATTTTAA CCTACCACCT GTAGTAGCAA AAGAAATAGT AGCCAGCTGT    4020

GATAAATGTC AGCTAAAAGG GGAAGCCATG CATGGACAAG TAGACTGTAG CCCAGGAATA    4080

TGGCAGCTAG ATTGTACACA TTTAGAAGGA AAAGTTATCT TGGTAGCAGT TCATGTAGCC    4140

AGTGGATATA TAGAAGCAGA AGTAATTCCA GCAGAGACAG GGCAAGAAAC AGCATACTTC    4200

CTCTTAAAAT TAGCAGGAAG ATGGCCAGTA AAAACAGTAC ATACAGACAA TGGCAGCAAT    4260

TTCACCAGTA CTACAGTTAA GGCCGCCTGT TGGTGGGCGG GGATCAAGCA GGAATTTGGC    4320

ATTCCCTACA ATCCCCAAAG TCAAGGAGTA ATAGAATCTA TGAATAAAGA ATTAAAGAAA    4380

ATTATAGGAC AGGTAAGAGA TCAGGCTGAA CATCTTAAGA CAGCAGTACA AATGGCAGTA    4440

TTCATCCACA ATTTTAAAAG AAAAGGGGGG ATTGGGGGGT ACAGTGCAGG GGAAAGAATA    4500

GTAGACATAA TAGCAACAGA CATACAAACT AAAGAATTAC AAAAACAAAT TACAAAAATT    4560

CAAAATTTTC GGGTTTATTA CAGGGACAGC AGAGATCCAG TTTGGAAAGG ACCAGCAAAG    4620

CTCCTCTGGA AAGGTGAAGG GGCAGTAGTA ATACAAGATA ATAGTGACAT AAAAGTAGTG    4680

CCAAGAAGAA AAGCAAAGAT CATCAGGGAT TATGGAAAAC AGATGGCAGG TGATGATTGT    4740

GTGGCAAGTA GACAGGATGA GGATTAACAC ATGGAAAAGA TTAGTAAAAC ACCATATGTA    4800

TATTTCAAGG AAAGCTAAGG ACTGGTTTTA TAGACATCAC TATGAAAGTA CTAATCCAAA    4860

AATAAGTTCA GAAGTACACA TCCCACTAGG GGATGCTAAA TTAGTAATAA CAACATATTG    4920

GGGTCTGCAT ACAGGAGAAA GAGACTGGCA TTTGGGTCAG GGAGTCTCCA TAGAATGGAG    4980

GAAAAAGAGA TATAGCACAC AAGTAGACCC TGACCTAGCA GACCAACTAA TTCATCTGCA    5040

CTATTTTGAT TGTTTTTCAG AATCTGCTAT AAGAAATACC ATATTAGGAC GTATAGTTAG    5100

TCCTAGGTGT GAATATCAAG CAGGACATAA CAAGGTAGGA TCTCTACAGT ACTTGGCACT    5160

AGCAGCATTA ATAAAACCAA AACAGATAAA GCCACCTTTG CCTAGTGTTA GGAAACTGAC    5220

AGAGGACAGA TGGAACAAGC CCCAGAAGAC CAAGGGCCAC AGAGGGAGCC ATACAATGAA    5280

TGGACACTAG AGCTTTTAGA GGAACTTAAG AGTGAAGCTG TTAGACATTT TCCTAGGATA    5340

TGGCTCCATA ACTTAGGACA ACATATCTAT GAAACTTACG GGGATACTTG GCAGGAGTG    5400

GAAGCCATAA TAAGAATTCT GCAACAACTG CTGTTTATCC ATTTCAGAAT TGGGTGTCGA    5460

CATAGCAGAA TAGGCGTTAC TCGACAGAGG AGAGCAAGAA ATGGAGCCAG TAGATCCTAG    5520

ACTAGAGCCC TGGAAGCATC CAGGAAGTCA GCCTAAAACT GCTTGTACCA ATTGCTATTG    5580

TAAAAAGTGT TGCTTTCATT GCCAAGTTTG TTTCATGACA AAAGCCTTAG GCATCTCCTA    5640

TGGCAGGAAG AAGCGGAGAC AGCGACGAAG AGCTCATCAG AACAGTCAGA CTCATCAAGC    5700

TTCTCTATCA AAGCAGTAAG TAGTACATGT AATGCAACCT ATAATAGTAG CAATAGTAGC    5760

ATTAGTAGTA GCAATAATAA TAGCAATAGT TGTGTGGTCC ATAGTAATCA TAGAATATAG    5820

GAAAATATTA AGACAAAGAA AAATAGACAG GTTAATTGAT AGACTAATAG AAAGAGCAGA    5880

AGACAGTGGC AATGAGAGTG AAGGAGAAGT ATCAGCACTT GTGGAGATGG GGGTGGAAAT    5940

GGGGCACCAT GCTCCTTGGG ATATTGATGA TCTGTAGTGC TACAGAAAAA TTGTGGGTCA    6000

CAGTCTATTA TGGGGTACCT GTGTGGAAGG AAGCAACCAC CACTCTATTT TGTGCATCAG    6060

ATGCTAAAGC ATATGATACA GAGGTACATA ATGTTTGGGC CACACATGCC TGTGTACCCA    6120

CAGACCCCAA CCCACAAGAA GTAGTATTGG TAAATGTGAC AGAAAATTTT AACATGTGGA    6180

AAAATGACAT GGTAGAACAG ATGCATGAGG ATATAATCAG TTTATGGGAT CAAAGCCTAA    6240
```

-continued

```
AGCCATGTGT AAAATTAACC CCACTCTGTG TTAGTTTAAA GTGCACTGAT TTGAAGAATG    6300
ATACTAATAC CAATAGTAGT AGCGGGAGAA TGATAATGGA GAAAGGAGAG ATAAAAAACT    6360
GCTCTTTCAA TATCAGCACA AGCATAAGAG ATAAGGTGCA GAAAGAATAT GCATTCTTTT    6420
ATAAACTTGA TATAGTACCA ATAGATAATA CCAGCTATAG GTTGATAAGT TGTAACACCT    6480
CAGTCATTAC ACAGGCCTGT CCAAAGGTAT CCTTTGAGCC AATTCCCATA CATTATTGTG    6540
CCCCGGCTGG TTTTGCGATT CTAAAATGTA ATAATAAGAC GTTCAATGGA ACAGGACCAT    6600
GTACAAATGT CAGCACAGTA CAATGTACAC ATGGAATCAG GCCAGTAGTA TCAACTCAAC    6660
TGCTGTTAAA TGGCAGTCTA GCAGAAGAAG ATGTAGTAAT TAGATCTGCC AATTTCACAG    6720
ACAATGCTAA AACCATAATA GTACAGCTGA ACACATCTGT AGAAATTAAT TGTACAAGAC    6780
CCAACAACAA TACAAGAAAA AGTATCCGTA TCCAGAGGGG ACCAGGGAGA GCATTTGTTA    6840
CAATAGGAAA AATAGGAAAT ATGAGACAAG CACATTGTAA CATTAGTAGA GCAAAATGGA    6900
ATGCCACTTT AAAACAGATA GCTAGCAAAT TAAGAGAACA ATTTGGAAAT AATAAAACAA    6960
TAATCTTTAA GCAATCCTCA GGAGGGGACC CAGAAATTGT AACGCACAGT TTTAATTGTG    7020
GAGGGGAATT TTTCTACTGT AATTCAACAC AACTGTTTAA TAGTACTTGG TTTAATAGTA    7080
CTTGGAGTAC TGAAGGGTCA AATAACACTG AAGGAAGTGA CACAATCACA CTCCCATGCA    7140
GAATAAAACA ATTTATAAAC ATGTGGCAGG AAGTAGGAAA AGCAATGTAT GCCCCTCCCA    7200
TCAGTGGACA AATTAGATGT TCATCAAATA TTACTGGGCT GCTATTAACA AGAGATGGTG    7260
GTAATAACAA CAATGGGTCC GAGATCTTCA GACCTGGAGG AGGCGATATG AGGGACAATT    7320
GGAGAAGTGA ATTATATAAA TATAAAGTAG TAAAAATTGA ACCATTAGGA GTAGCACCCA    7380
CCAAGGCAAA GAGAAGAGTG GTGCAGAGAG AAAAAAGAGC AGTGGGAATA GGAGCTTTGT    7440
TCCTTGGGTT CTTGGGAGCA GCAGGAAGCA CTATGGGCGC ACGGTCAATG ACGCTGACGG    7500
TACAGGCCAG ACAATTATTG TCTGATATAG TGCAGCAGCA GAACAATTTG CTGAGGGCTA    7560
TTGAGGCGCA ACAGCATCTG TTGCAACTCA CAGTCTGGGG CATCAAACAG CTCCAGGCAA    7620
GAATCCTGGC TGTGGAAAGA TACCTAAAGG ATCAACAGCT CCTGGGGATT TGGGGTTGCT    7680
CTGGAAAACT CATTTGCACC ACTGCTGTGC CTTGGAATGC TAGTTGGAGT AATAAATCTC    7740
TGGAACAGAT TTGGAATAAC ATGACCTGGA TGGAGTGGGA CAGAGAAATT AACAATTACA    7800
CAAGCTTAAT ACACTCCTTA ATTGAAGAAT CGCAAAACCA GCAAGAAAAG AATGAACAAG    7860
AATTATTGGA ATTAGATAAA TGGGCAAGTT TGTGGAATTG GTTTAACATA ACAAATTGGC    7920
TGTGGTATAT AAAATTATTC ATAATGATAG TAGGAGGCTT GGTAGGTTTA AGAATAGTTT    7980
TTGCTGTACT TTCTATAGTG AATAGAGTTA GGCAGGGATA TTCACCATTA TCGTTTCAGA    8040
CCCACCTCCC AATCCCGAGG GGACCCGACA GGCCCGAAGG AATAGAAGAA GAAGGTGGAG    8100
AGAGAGACAG AGACAGATCC ATTCGATTAG TGAACGGATC CTTAGCACTT ATCTGGGACG    8160
ATCTGCGGAG CCTGTGCCTC TTCAGCTACC ACCGCTTGAG AGACTTACTC TTGATTGTAA    8220
CGAGGATTGT GGAACTTCTG GGACGCAGGG GGTGGGAAGC CCTCAAATAT TGGTGGAATC    8280
TCCTACAGTA TTGGAGTCAG GAACTAAAGA ATAGTGCTGT TAACTTGCTC AATGCCACAG    8340
CCATAGCAGT AGCTGAGGGG ACAGATAGGG TTATAGAAGT ATTACAAGCA GCTTATAGAG    8400
CTATTCGCCA CATACCTAGA AGAATAAGAC AGGGCTTGGA AAGGATTTTG CTATAAGCTT    8460
TATATATAGT GTTATAGTGC GCCAGATCTC TATAATCTCG CGCAACCTAT TTTCCCCTCG    8520
AACACTTTTT AAGCCGTAGA TAAACAGGCT GGGACACTTC ACATGAGCGA AAATACATC     8580
GTCACCTGGG ACATGTTGCA GATCCATGCA CGTAAACTCG CAAGCCGACT GATGCCTTCT    8640
```

```
GAACAATGGA AAGGCATTAT TGCCGTAAGC CGTGGCGGTC TGGTACCGGG TGCGTTACTG   8700

GCGCGTGAAC TGGGTATTCG TCATGTCGAT ACCGTTTGTA TTTCCAGCTA CGATCACGAC   8760

AACCAGCGCG AGCTTAAAGT GCTGAAACGC GCAGAAGGCG ATGGCGAAGG CTTCATCGTT   8820

ATTGATGACC TGGTGGATAC CGGTGGTACT GCGGTTGCGA TTCGTGAAAT GTATCCAAAA   8880

GCGCACTTTG TCACCATCTT CGCAAAACCG GCTGGTCGTC CGCTGGTTGA TGACTATGTT   8940

GTTGATATCC CGCAAGATAC CTGGATTGAA CAGCCGTGGG ATATGGGCGT CGTATTCGTC   9000

CCGCCAATCT CCGGTCGCTA ACTCGAGACT CGAGGCCGGC AAGGCCGGAT CCAGACATGA   9060

TAAGATACAT TGATGAGTTT GGACAAACCA CAACTAGAAT GCAGTGAAAA AAATGCTTTA   9120

TTTGTGAAAT TTGTGATGCT ATTGCTTTAT TTGTAACCAT TATAAGCTGC AATAAACAAG   9180

TTAACAACAA CAATTGCATT CATTTTATGT TTCAGGTTCA GGGGGAGGTG GGGAGGTTTT   9240

TTAAAGCAAG TAAAACCTCT ACAAATGTGG TATGGCTGAT TATGATCCGG CTGCCTCGCG   9300

CGTTTCGGTG ATGACGGTGA AAACCTCTGA CACATGCAGC TCCCGGAGAC GGTCACAGCT   9360

TGTCTGTAAG CGGATGCCGG GAGCAGACAA GCCCGTCAGG GCGCGTCAGC GGGTGTTGGC   9420

GGGTGTCGGG GCGCAGCCAT GACCGGTCGA CTGCAGTCTC TGCAGGAATT CGATATCAAG   9480

CTTATCGATA CCGTCGACCT CGAGGGGGGG CCCGGTACCC AATTCGCCCT ATAGTGAGTC   9540

GTATTACAAT TCACTGGCCG TCGTTTTACA ACGTCGTGAC TGGGAAAACC CTGGCGTTAC   9600

CCAACTTAAT CGCCTTGCAG CACATCCCCC TTTCGCCAGC TGGCGTAATA GCGAAGAGGC   9660

CCGCACCGAT CGCCCTTCCC AACAGTTGCG CAGCCTGAAT GGCGAATGGA AATTGTAAGC   9720

GTTAATATTT TGTTAAAATT CGCGTTAAAT TTTTGTTAAA TCAGCTCATT TTTTAACCAA   9780

TAGGCCGAAA TCGGCAAAAT CCCTTATAAA TCAAAAGAAT AGACCGAGAT AGGGTTGAGT   9840

GTTGTTCCAG TTTGGAACAA GAGTCCACTA TTAAAGAACG TGGACTCCAA CGTCAAAGGG   9900

CGAAAAACCG TCTATCAGGG CGATGGCCCA CTACGTGAAC CATCACCCTA ATCAAGTTTT   9960

TTGGGGTCGA GGTGCCGTAA AGCACTAAAT CGGAACCCTA AAGGGAGCCC CCGATTTAGA  10020

GCTTGACGGG GAAAGCCGGC GAACGTGGCG AGAAAGGAAG GGAAGAAAGC GAAAGGAGCG  10080

GGCGCTAGGG CGCTGGCAAG TGTAGCGGTC ACGCTGCGCG TAACCACCAC ACCCGCCGCG  10140

CTTAATGCGC CGCTACAGGG CGCGTCAGGT GGCACTTTTC GGGGAAATGT GCGCGGAACC  10200

CCTATTTGTT TATTTTTCTA AATACATTCA AATATGTATC CGCTCATGAG ACAATAACCC  10260

TGATAAATGC TTCAATAATA TTGAAAAAGG AAGAGTATGA GTATTCAACA TTTCCGTGTC  10320

GCCCTTATTC CCTTTTTTGC GGCATTTTGC CTTCCTGTTT TTGCTCACCC AGAAACGCTG  10380

GTGAAAGTAA AAGATGCTGA AGATCAGTTG GGTGCACGAG TGGGTTACAT CGAACTGGAT  10440

CTCAACAGCG GTAAGATCCT TGAGAGTTTT CGCCCCGAAG AACGTTTTCC AATGATGAGC  10500

ACTTTTAAAG TTCTGCTATG TGGCGCGGTA TTATCCCGTA TTGACGCCGG GCAAGAGCAA  10560

CTCGGTCGCC GCATACACTA TTCTCAGAAT GACTTGGTTG AGTACTCACC AGTCACAGAA  10620

AAGCATCTTA CGGATGGCAT GACAGTAAGA GAATTATGCA GTGCTGCCAT AACCATGAGT  10680

GATAACACTG CGGCCAACTT ACTTCTGACA ACGATCGGAG GACCGAAGGA GCTAACCGCT  10740

TTTTTGCACA ACATGGGGGA TCATGTAACT CGCCTTGATC GTTGGGAACC GGAGCTGAAT  10800

GAAGCCATAC CAAACGACGA GCGTGACACC ACGATGCCTG TAGCAATGGC AACAACGTTG  10860

CGCAAACTAT TAACTGGCGA ACTACTTACT CTAGCTTCCC GGCAACAATT AATAGACTGG  10920

ATGGAGGCGG ATAAAGTTGC AGGACCACTT CTGCGCTCGG CCCTTCCGGC TGGCTGGTTT  10980
```

-continued

```
ATTGCTGATA AATCTGGAGC CGGTGAGCGT GGGTCTCGCG GTATCATTGC AGCACTGGGG     11040

CCAGATGGTA AGCCCTCCCG TATCGTAGTT ATCTACACGA CGGGGAGTCA GGCAACTATG     11100

GATGAACGAA ATAGACAGAT CGCTGAGATA GGTGCCTCAC TGATTAAGCA TTGGTAACTG     11160

TCAGACCAAG TTTACTCATA TATACTTTAG ATTGATTTAA AACTTCATTT TTAATTTAAA     11220

AGGATCTAGG TGAAGATCCT TTTTGATAAT CTCATGACCA AAATCCCTTA ACGTGAGTTT     11280

TCGTTCCACT GAGCGTCAGA CCCCGTAGAA AAGATCAAAG GATCTTCTTG AGATCCTTTT     11340

TTTCTGCGCG TAATCTGCTG CTTGCAAACA AAAAACCAC CGCTACCAGC GGTGGTTTGT      11400

TTGCCGGATC AAGAGCTACC AACTCTTTTT CCGAAGGTAA CTGGCTTCAG CAGAGCGCAG     11460

ATACCAAATA CTGTCCTTCT AGTGTAGCCG TAGTTAGGCC ACCACTTCAA GAACTCTGTA     11520

GCACCGCCTA CATACCTCGC TCTGCTAATC CTGTTACCAG TGGCTGCTGC CAGTGGCGAT     11580

AAGTCGTGTC TTACCGGGTT GGACTCAAGA CGATAGTTAC CGGATAAGGC GCAGCGGTCG     11640

GGCTGAACGG GGGGTTCGTG CACACAGCCC AGCTTGGAGC GAACGACCTA CACCGAACTG     11700

AGATACCTAC AGCGTGAGCT ATGAGAAAGC GCCACGCTTC CCGAAGGGAG AAAGGCGGAC     11760

AGGTATCCGG TAAGCGGCAG GGTCGGAACA GGAGAGCGCA CGAGGGAGCT TCCAGGGGGA     11820

AACGCCTGGT ATCTTTATAG TCCTGTCGGG TTTCGCCACC TCTGACTTGA GCGTCGATTT     11880

TTGTGATGCT CGTCAGGGGG GCGGAGCCTA TGGAAAAACG CCAGCAACGC GGCCTTTTTA     11940

CGGTTCCTGG CCTTTTGCTG GCCTTTTGCT CACATGTTCT TTCCTGCGTT ATCCCCTGAT     12000

TCTGTGGATA ACCGTATTAC CGCCTTTGAG TGAGCTGATA CCGCTCGCCG CAGCCGAACG     12060

ACCGAGCGCA GCGAGTCAGT GAGCGAGGAA GCGGAAGAGC GCCCAATACG CAAACCGCCT     12120

CTCCCCGCGC GTTGGCCGAT TCATTAATGC AGCTGGCACG ACAGGTTTCC CGACTGGAAA     12180

GCGGGCAGTG AGCGCAACGC AATTAATGTG AGTTAGCTCA CTCATTAGGC ACCCCAGGCT     12240

TTACACTTTA TGCTTCCGGC TCGTATGTTG TGTGGAATTG TGAGCGGATA ACAATTTCAC     12300

ACAGGAAACA GCTATGACCA TGATTACGCC AAGCTCGAAA TTAACCCTCA CTAAAGGGAA     12360

CAAAAGCTGG AGCTCCACCG CGGTGGCGGC CGTCTCTAGA ACTAGTGGAT CCCCCGGGCT     12420

GCAGGAATTC GATAACACAC TGGCTTATCG AAATTAATAC GACTCACTAT AGGGAGACCG     12480

GCAGATCTGA TATC                                                      12494
```

(2) INFORMATION FOR SEQ ID NO:14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = ""DNA""

(xi) SEQUENCE DESCRIPTION: SEQ ID NO:14:

```
TAAGAATTCT AGTAGGTTGC TTTCATTGCC                                       30
```

(2) INFORMATION FOR SEQ ID NO:15:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = ""DNA""

(xi) SEQUENCE DESCRIPTION: SEQ ID NO:15:

CTTCTCCTTC ACTCTCGAGT GATCACTGTC TTCTGCTCTT TC                42

(2) INFORMATION FOR SEQ ID NO:16:

(i) SEQUENCE CHARACTERISTICS:
        (A) LENGTH: 140 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = ""DNA""

(xi) SEQUENCE DESCRIPTION: SEQ ID NO:16:

AGGCGTTACT CGACAGAGGA GAGCAAGAAA TGGAGCCAGT AGATCCTAGA CTATAGGCCT    60

GGAAGCATCC AGGAAGTCAG CCTAAAACTG CTTGTACCAA TTGCTATTGT AAAAAGTGTT   120

GCTTTCATTG CCAAGTTTGT                                               140

(2) INFORMATION FOR SEQ ID NO:17:

(i) SEQUENCE CHARACTERISTICS:
        (A) LENGTH: 118 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = ""DNA""

(xi) SEQUENCE DESCRIPTION: SEQ ID NO:17:

AGGCGTTACT CGACAGAGGA GAGCAAGAAA CGGCGCCTCG CGTAGCTAGC GGCCGCCCGG    60

GATCGATACG CGTACCAATT GCTATTGTAA AAAGTGTTGC TTTCATTGCC AAGTTTGT    118

(2) INFORMATION FOR SEQ ID NO:18:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = ""DNA""

(xi) SEQUENCE DESCRIPTION: SEQ ID NO:18:

TATAAGCTTG GTGGCAAGTG GTCAAAAAGT AGTGTGATTG GATGGCCTGC TGTAAGGGAA    60

AGAATGAGAC                                                          70

(2) INFORMATION FOR SEQ ID NO:19:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = ""DNA""

(xi) SEQUENCE DESCRIPTION: SEQ ID NO:19:

CTCAGGTACC TTTAAGACTC TAGATCTAGA AGGCAGCTGT AGATCTTAGC CACTTTTTAA    60

AAGAAAAGGG                                                          70

(2) INFORMATION FOR SEQ ID NO:20:

(i) SEQUENCE CHARACTERISTICS:
        (A) LENGTH: 140 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = ""DNA""

(xi) SEQUENCE DESCRIPTION: SEQ ID NO:20:

```
AGGCGTTACT CGACAGAGGA GAGCAAGAAA TGGAGCCAGT AGATCCTAGA CTATAGGCCT      60

GGAAGCATCC AGGAAGTTAG CCTTAAACTG CTTGTACCAA TTGCTATTGT AAAAAGTGTT     120

GCTTTCATTG CCAAGTTTGT                                                  140
```